(12) United States Patent
He et al.

(10) Patent No.: US 10,647,710 B2
(45) Date of Patent: May 12, 2020

(54) THIAZOLE DERIVATIVE AND APPLICATIONS THEREOF

(71) Applicant: Medshine Discovery Inc., Nanjing, Jiangsu (CN)

(72) Inventors: Haiying He, Shanghai (CN); Zhigan Jiang, Shanghai (CN); Weihua Shi, Shanghai (CN); Jianhua Xia, Shanghai (CN); Jian Li, Shanghai (CN); Shuhui Chen, Shanghai (CN)

(73) Assignee: Medshine Discovery Inc., Nanjing, Jiangsu (CN)

( * ) Notice: Subject to any disclaimer, the term of this patent is extended or adjusted under 35 U.S.C. 154(b) by 0 days.

(21) Appl. No.: 16/476,797

(22) PCT Filed: Jan. 9, 2018

(86) PCT No.: PCT/CN2018/071964
§ 371 (c)(1),
(2) Date: Jul. 9, 2019

(87) PCT Pub. No.: WO2018/127207
PCT Pub. Date: Jul. 12, 2018

(65) Prior Publication Data
US 2019/0375744 A1    Dec. 12, 2019

(30) Foreign Application Priority Data
Jan. 9, 2017 (CN) .......................... 2017 1 0014893

(51) Int. Cl.
| | |
|---|---|
| *C07D 417/12* | (2006.01) |
| *C07D 417/14* | (2006.01) |
| *C07D 277/54* | (2006.01) |
| *A61P 31/22* | (2006.01) |

(52) U.S. Cl.
CPC ............ *C07D 417/12* (2013.01); *A61P 31/22* (2018.01); *C07D 277/54* (2013.01); *C07D 417/14* (2013.01)

(58) Field of Classification Search
CPC .. C07D 417/12; C07D 277/54; C07D 417/14; A61P 31/22
USPC ...................................................... 546/269.7
See application file for complete search history.

(56) References Cited

U.S. PATENT DOCUMENTS 7,223,782 B2 * 5/2007 Atkinson ............. C07D 231/14
514/406

* cited by examiner

Primary Examiner — Niloofar Rahmani
(74) Attorney, Agent, or Firm — Polsinelli P.C.

(57) ABSTRACT

Disclosed in the present invention are a new thiazole compound, particularly a compound represented by formula (I), a pharmaceutical composition thereof and applications thereof in the preparation of drugs for the treatment of diseases related to herpes simplex viruses.

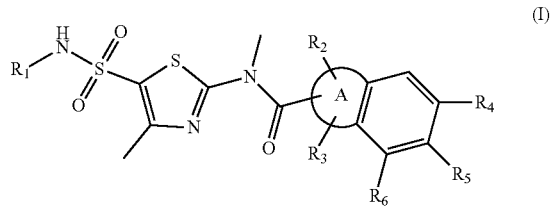

21 Claims, No Drawings

THIAZOLE DERIVATIVE AND APPLICATIONS THEREOF

CROSS-REFERENCE TO RELATED APPLICATIONS

The present application is a national stage filing under 35 U.S.C. § 371 of PCT International Application No. PCT/CN2018/071964, filed Jan. 9, 2018, which claims the benefit of the Chinese Patent Application No. CN201710014893.9, filed on Jan. 9, 2017, the entire contents of each of which is are incorporated by reference herein in their entirety.

TECHNICAL FIELD

The present disclosure relates to a novel thiazole compound, especially a compound of formula (I), or a pharmaceutical composition thereof, and use of the same in the manufacture of a medicament for treating a disease associated with herpes simplex viruses.

BACKGROUND

There is a great need for new treatments for viral diseases. Although great progress has been made in the development of treatments for various bacterial infections, there are only few feasible treatments for viruses. Among important drugs for treating human immunodeficiency virus, Zidovudine is well recognized. Ganciclovir, acyclovir and foscarnet are currently used to treat herpes virus infection. However, these treatments have considerable side effects because they impair the replication of host cell DNA or only have effect for a limited number of viral infections. In addition, it is known that viruses can develop resistance to these treatments, and thus reducing the therapeutic effect.

Herpesviridae is a family of DNA viruses, including herpes simplex virus type 1 (HSV-1), herpes simplex virus type 2 (HSV-2), cytomegalovirus (CMV), varicella-zoster virus (VZV), Epstein-Barr virus, human herpesvirus-6 (HHV6), human herpesvirus-7 (HHV7), human herpesvirus-8 (HHV8), pseudorabies virus, rhinotracheitis virus, and the like.

SUMMARY

Disclosed herein is a compound represented by formula (I), or an isomer or a pharmaceutically acceptable salt thereof,

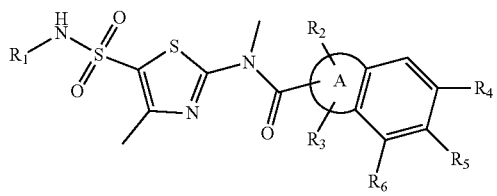

(I)

wherein
$R_1$ is selected from H, $C_{1-4}$ alkyl or $C_{3-6}$ cycloalkyl;
$R_2$ and $R_3$ are independently selected from H, or are independently selected from $C_{1-3}$ alkyl optionally substituted by 1, 2 or 3 R;
$R_4$, $R_5$, and $R_6$ are independently selected from H, F, Cl, Br, or I, or are independently selected from the group consisting of phenyl, 5- to 6-membered heteroaryl, and 5- to 6-membered heteroaryl-O—, each of which is optionally substituted by 1, 2 or 3 R;
ring A is selected from $C_{5-7}$ cycloalkyl or 5- to 8-membered heterocycloalkyl;
R is selected from F, Cl, OH, $NH_2$, —COOH, $C_{1-3}$ alkyl, $C_{1-3}$ alkoxy, alkyl)amino, or $C_{1-3}$ alkyl-C(=O)O—;
the heteroatom or heteroatom group in the 5- to 6-membered heteroaryl and the 5- to 8-membered heterocycloalkyl is independently selected from —S—, —O—, —NH—, or N; and
in any of the above cases, the number of the heteroatom or heteroatom group is independently selected from 1, 2 or 3.

In some embodiments of the disclosure, the above mentioned R is selected from F, Cl, OH, $NH_2$, —COOH, $CH_3$,

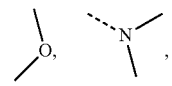

or $CH_3$—C(=O)O—.

In some embodiments of the disclosure, the above mentioned $R_1$ is selected from H or

In some embodiments of the disclosure, the above mentioned $R_2$ and $R_3$ are independently selected from H, or are independently selected from the group consisting of $CH_3$ and —$CH_2$—$CH_3$, each of which is optionally substituted by 1, 2 or 3 R.

In some embodiments of the disclosure, the above mentioned $R_2$ and $R_3$ are independently selected from H, $CH_3$, —$CH_2$—OH, or —$CH_2$—OAc.

In some embodiments of the disclosure, the above mentioned $R_2$ is selected from: H, $CH_3$, —$CH_2$—OH, or —$CH_2$—OAc.

In some embodiments of the disclosure, the above mentioned $R_3$ is selected from: H or $CH_3$.

In some embodiments of the disclosure, the above mentioned $R_4$, $R_5$ and $R_6$ are independently selected from H, F, Cl, Br or I, or are independently selected from the group consisting of pyridyl, thiazolyl, and pyridyl-O—, each of which is optionally substituted by 1, 2 or 3 R.

In some embodiments of the disclosure, the above mentioned $R_4$, $R_5$ and $R_6$ are independently selected from H, F, Cl, Br or I, or are independently selected from the group consisting of

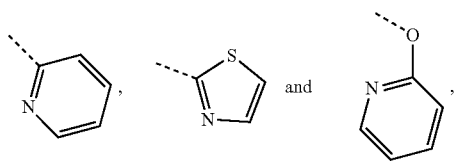

each of which is optionally substituted by 1, 2 or 3 R.

In some embodiments of the disclosure, the above mentioned $R_4$, $R_5$, and $R_6$ are independently selected from H, F, Cl,

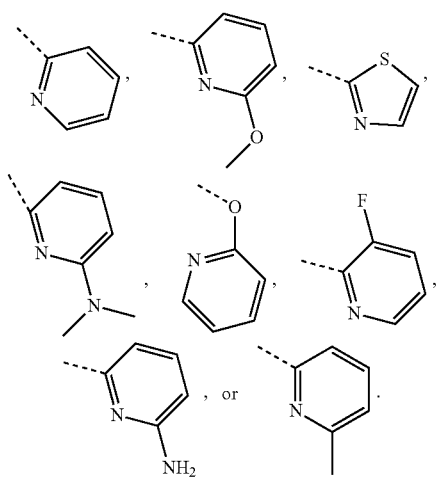

In some embodiments of the disclosure, the above mentioned $R_4$ is selected from H, F, Cl, or

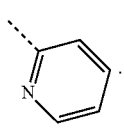

In some embodiments of the disclosure, the above mentioned $R_5$ is selected from H,

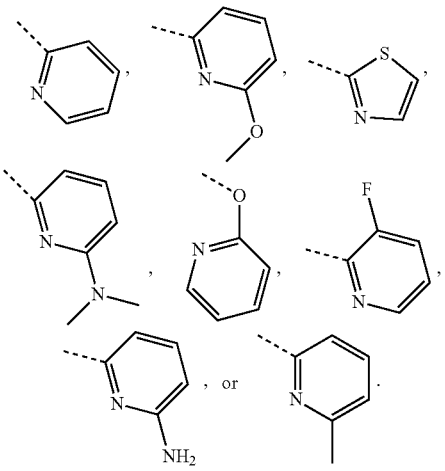

In some embodiments of the disclosure, the above mentioned $R_6$ is selected from H, F, Cl, or

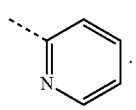

In some embodiments of the disclosure, the above mentioned ring A is selected from: piperidyl, pyrrolidinyl, tetrahydrofuryl, tetrahydropyranyl, oxepanyl, cyclopentyl, or cyclohexyl.

In some embodiments of the disclosure, the above mentioned moiety

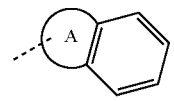

is selected from

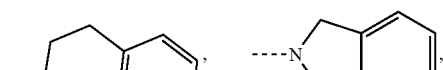

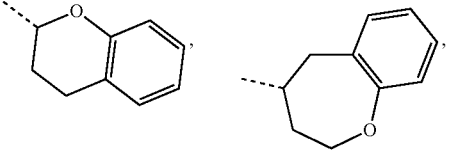

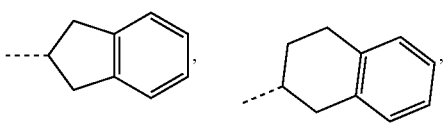

In some embodiments of the disclosure, the above mentioned moiety

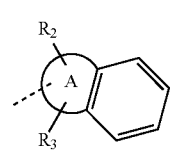

is selected from

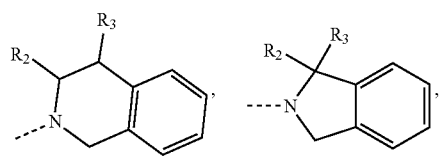

-continued

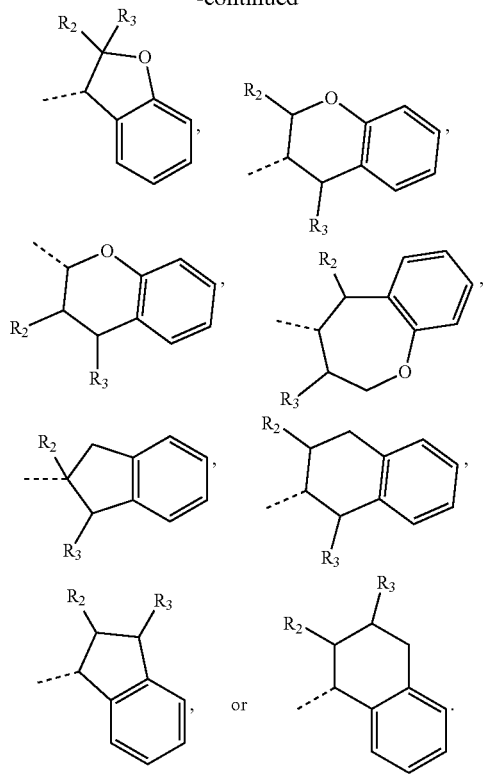

In some embodiments of the disclosure, the above mentioned moiety

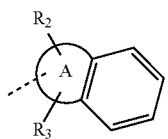

is selected from

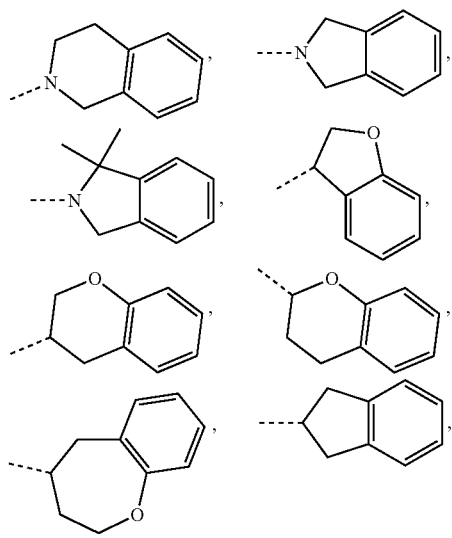

-continued

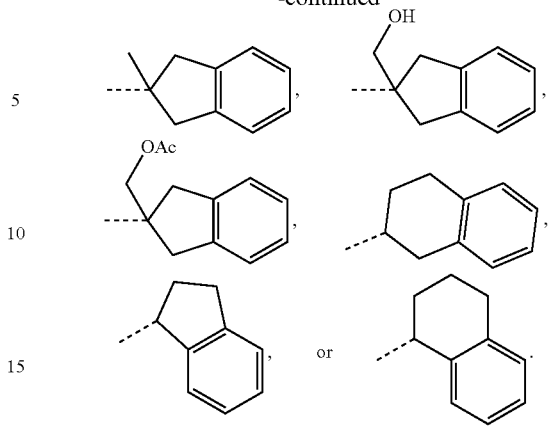

In some embodiments of the disclosure, the above mentioned R is selected from F, Cl, OH, NH$_2$, —COOH, CH$_3$,

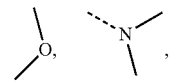

or CH$_3$—C(=O)O—, and the other variables are defined as above.

In some embodiments of the disclosure, the above mentioned R$_1$ is selected from: H or

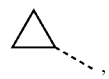

and the other variables are defined as above.

In some embodiments of the disclosure, the above mentioned R$_2$ and R$_3$ are independently selected from H, or are independently selected from the group consisting of CH$_3$ and —CH$_2$—CH$_3$, each of which is optionally substituted by 1, 2 or 3 R, and the other variables are defined as above.

In some embodiments of the disclosure, the above mentioned R$_2$ and R$_3$ are independently selected from H, CH$_3$, —CH$_2$—OH, or —CH$_2$—OAc, and the other variables are defined as above.

In some embodiments of the disclosure, the above mentioned R$_2$ is selected from: H, CH$_3$, —CH$_2$—OH, or —CH$_2$—OAc, and the other variables are defined as above.

In some embodiments of the disclosure, the above mentioned R$_3$ is selected from: H or CH$_3$, and the other variables are defined as above.

In some embodiments of the disclosure, the above mentioned R$_4$, R$_5$, and R$_6$ are independently selected from H, F, Cl, Br, or I, or are independently selected from the group consisting of pyridyl, thiazolyl, and pyridyl-O—, each of which is optionally substituted by 1, 2 or 3 R, and the other variables are defined as above.

In some embodiments of the disclosure, the above mentioned R$_4$, R$_5$, and R$_6$ are independently selected from H, F, Cl, Br or I, or are independently selected from the group consisting of

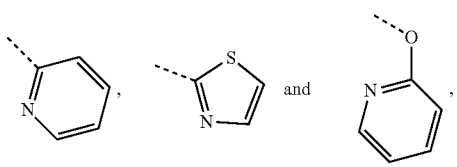 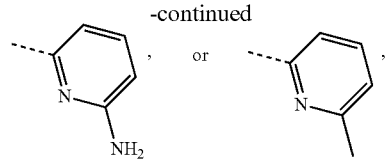

each of which is optionally substituted by 1, 2 or 3 R, and the other variables are defined as above.

In some embodiments of the disclosure, the above mentioned $R_4$, $R_5$, and $R_6$ are independently selected from H, F, Cl,

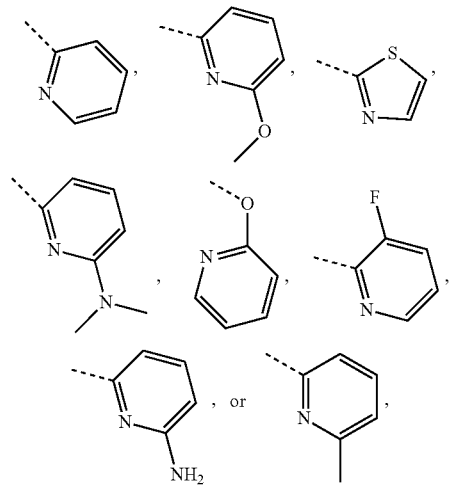

and the other variables are defined as above.

In some embodiments of the disclosure, the above mentioned $R_4$ is selected from H, F, Cl, or

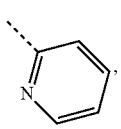

and the other variables are defined as above.

In some embodiments of the disclosure, the above mentioned $R_5$ is selected from H,

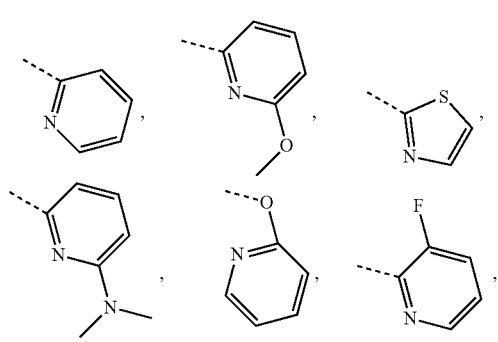

and the other variables are defined as above.

In some embodiments of the disclosure, the above mentioned $R_6$ is selected from H, F, Cl, or

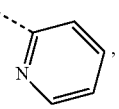

and the other variables are defined as above.

In some embodiments of the disclosure, the above mentioned ring A is selected from piperidyl, pyrrolidinyl, tetrahydrofuryl, tetrahydropyranyl, oxepanyl, cyclopentyl, or cyclohexyl, and the other variables are defined as above.

In some embodiments of the disclosure, the above mentioned moiety

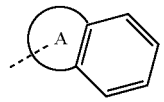

is selected from

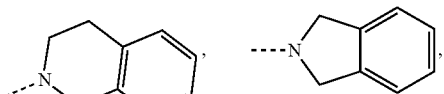
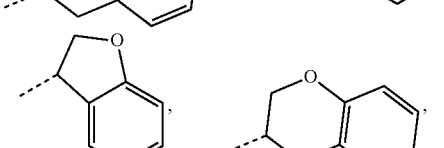
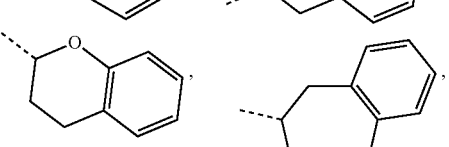
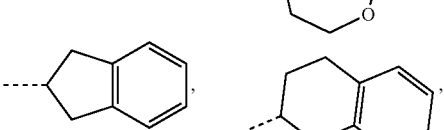
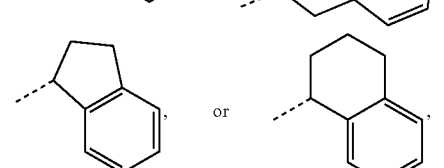

and the other variables are defined as above.

In some embodiments of the disclosure, the above mentioned moiety

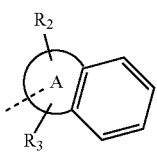

is selected from

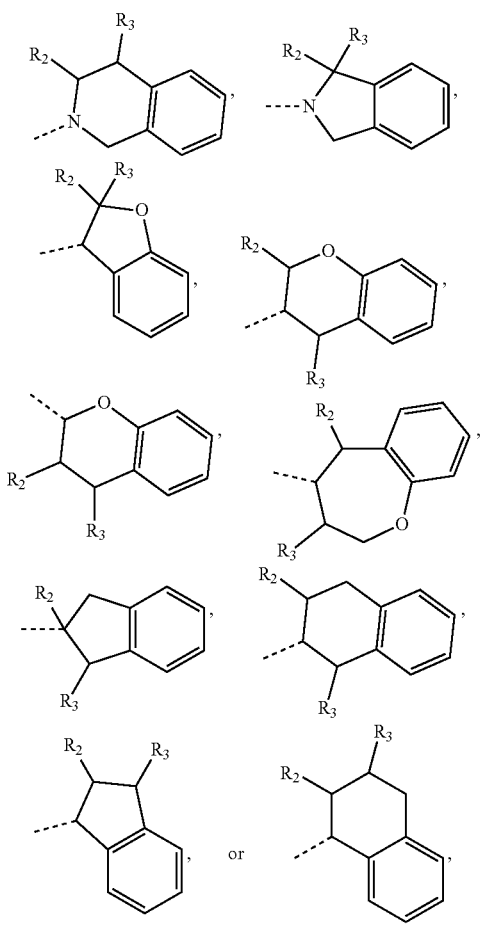

and the other variables are defined as above.

In some embodiments of the disclosure, the above mentioned moiety

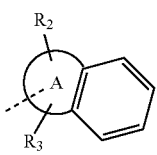

is selected from

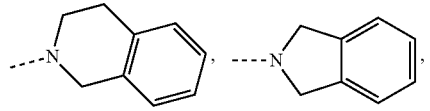

-continued

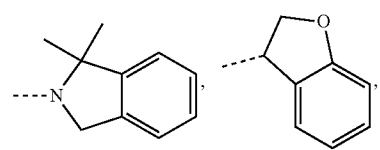
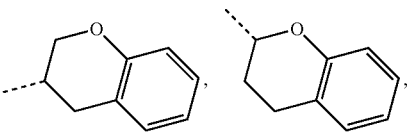
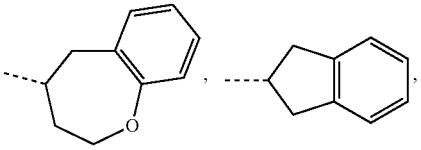
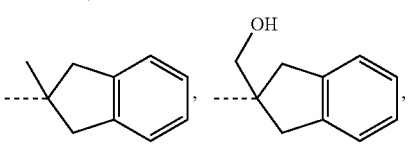
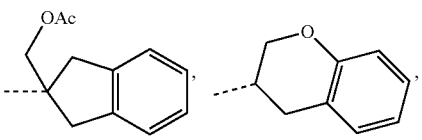
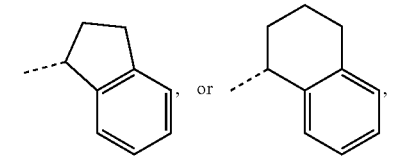

and the other variables are defined as above.

The present disclosure also includes some embodiments that are obtained by combination of any above definitions for the above variables.

In some embodiments of the disclosure, the compound, or the isomer or the pharmaceutically acceptable salt thereof mentioned above is selected from:

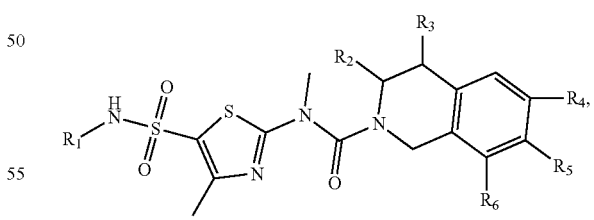
(I-1)

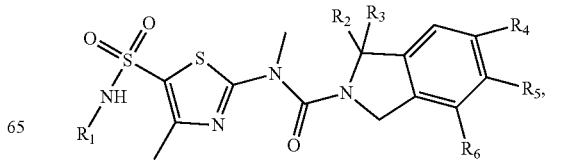
(I-2)

(I-3)
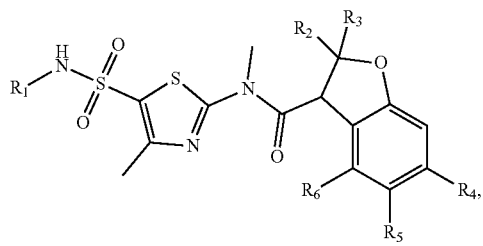
(I-4)
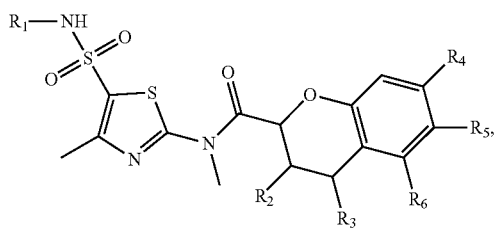
(I-5)
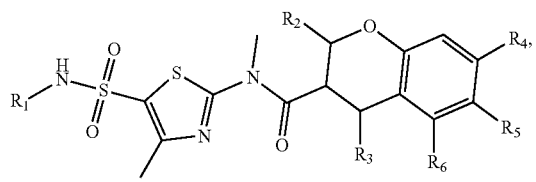
(I-6)
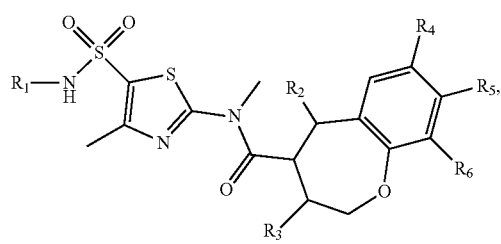
(I-7)
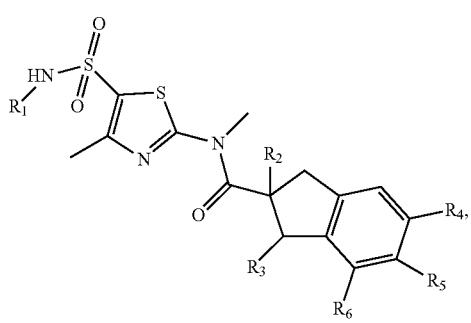
(I-8)
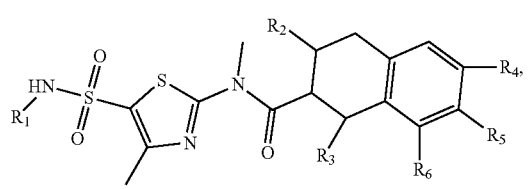
(I-9)
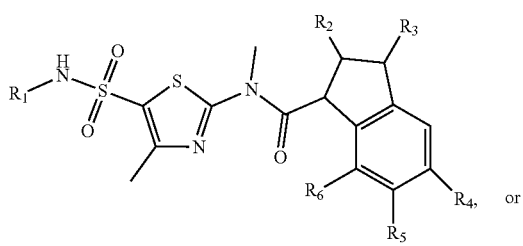
or
(I-10)
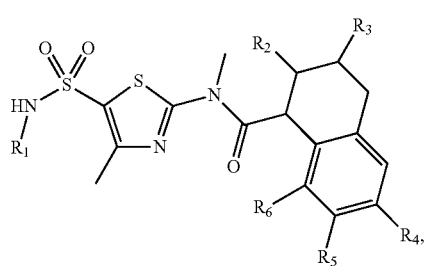
wherein $R_1$, $R_2$, $R_3$, $R_4$, $R_5$ and $R_6$ are defined as above.
The present disclosure provides the following compound, or an isomer or a pharmaceutically acceptable salt thereof:
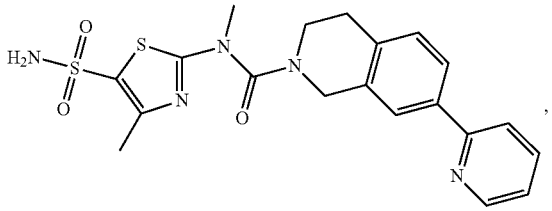,
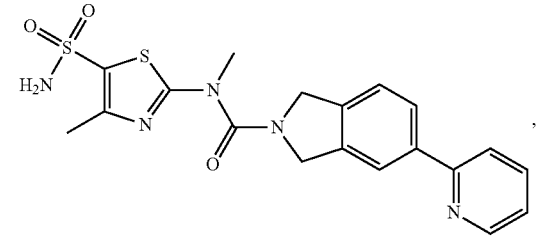,
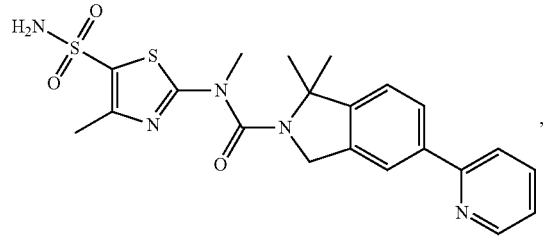,
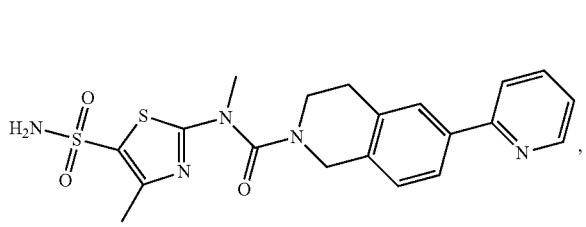,

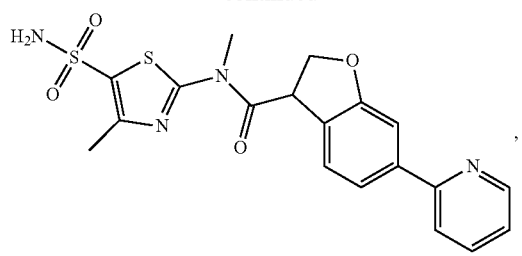
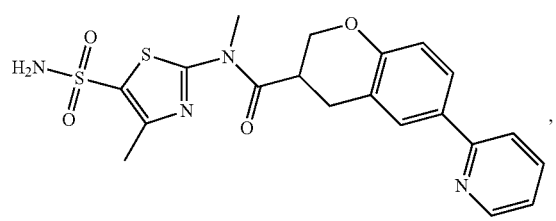
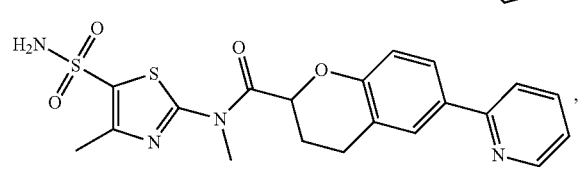
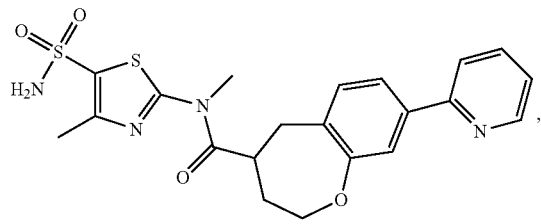
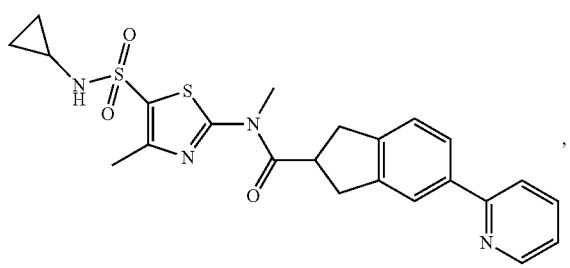
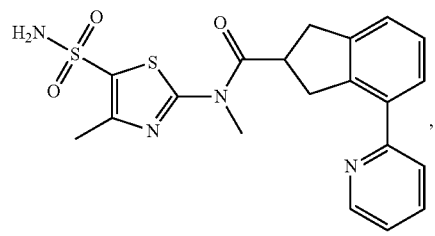
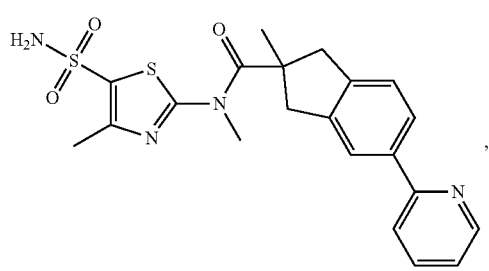
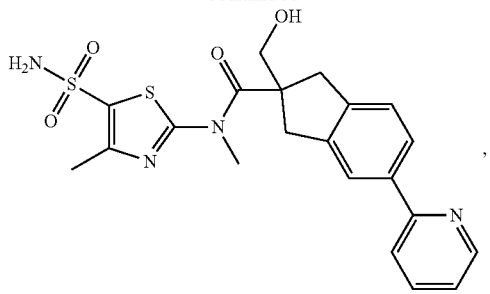
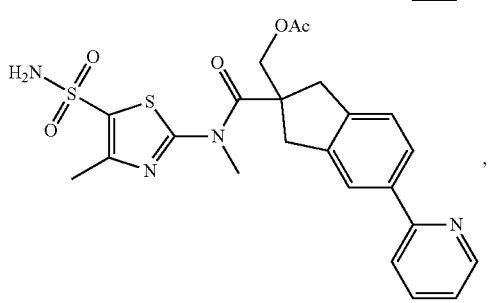
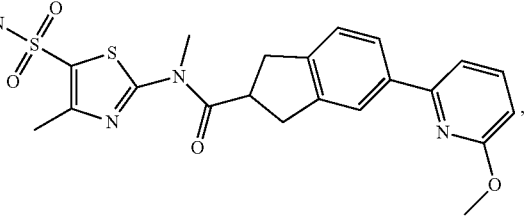
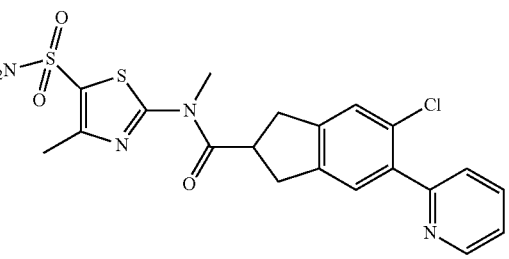
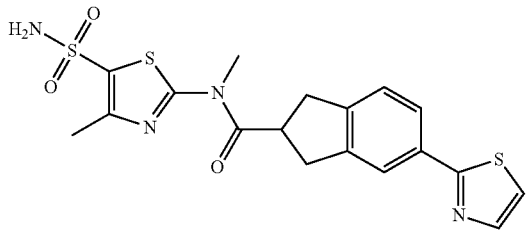
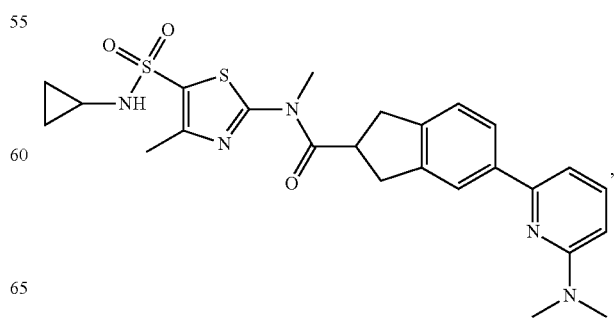

-continued
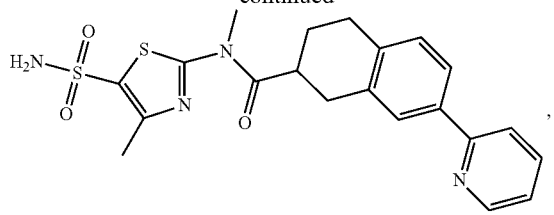
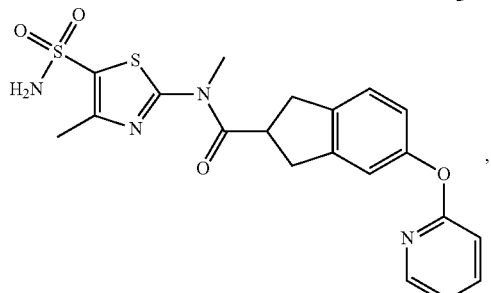
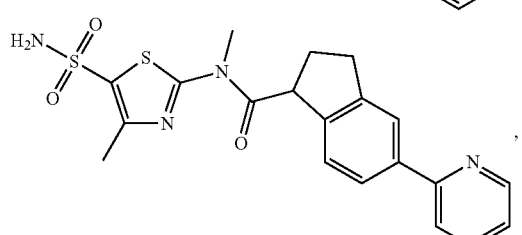
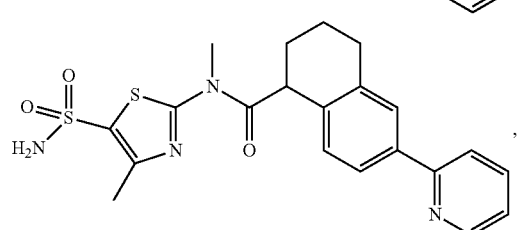
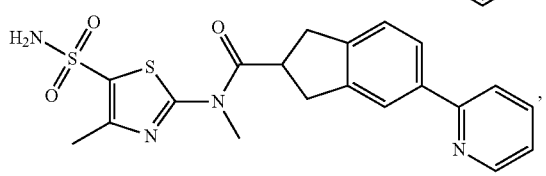
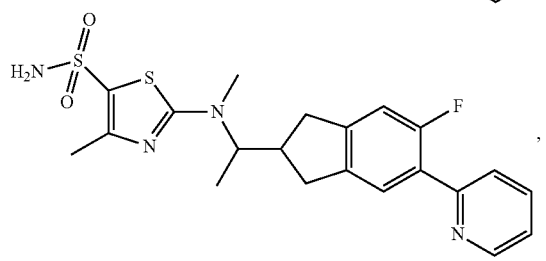
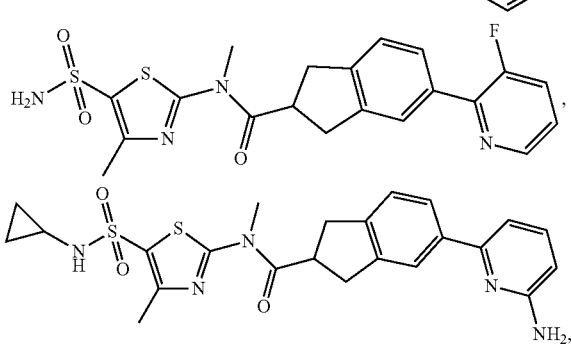
-continued
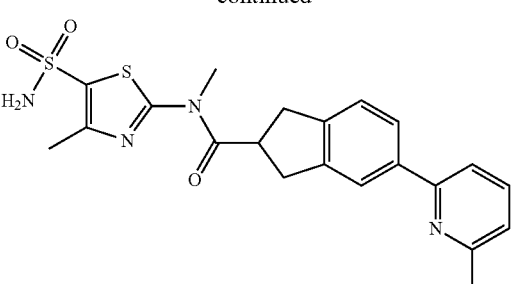
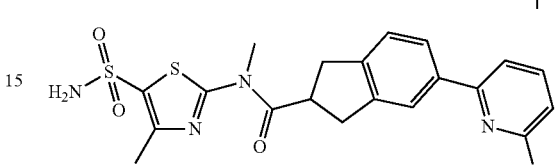
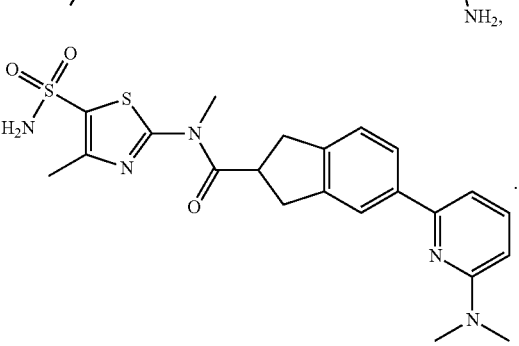
In some embodiments of the disclosure, the compound, or the isomer or the pharmaceutically acceptable salt thereof mentioned above is selected from:
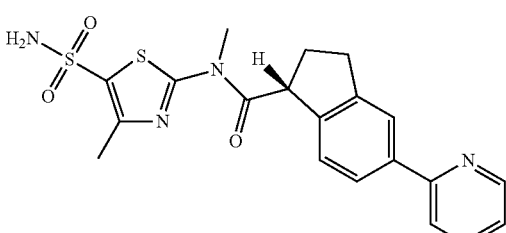
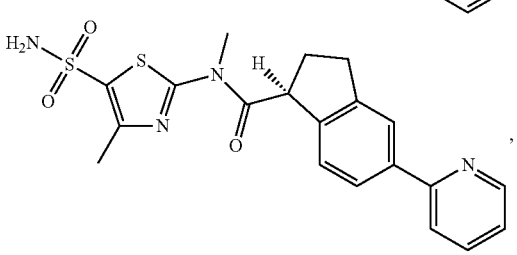
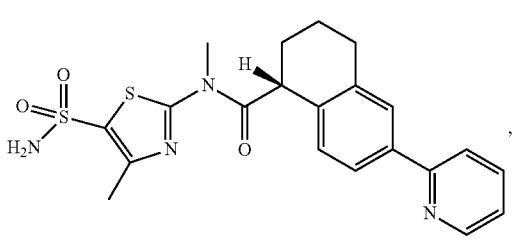

-continued

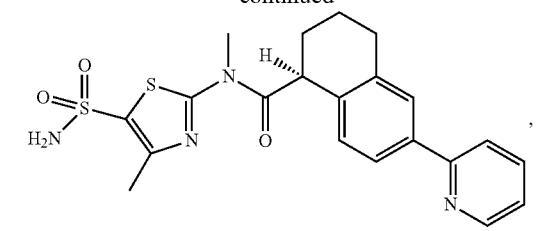

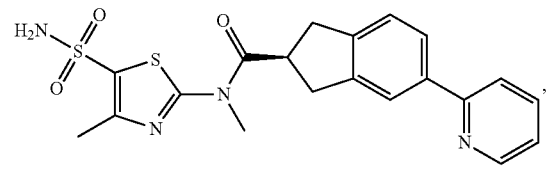

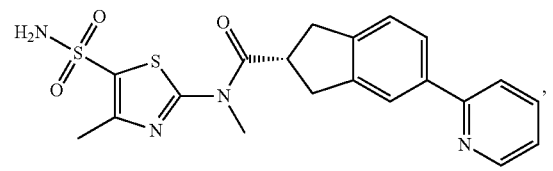

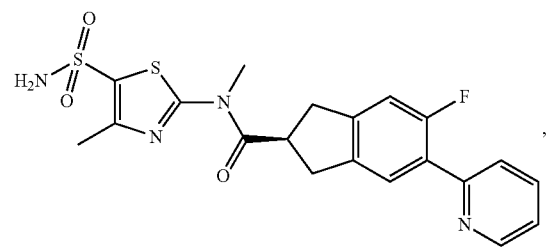

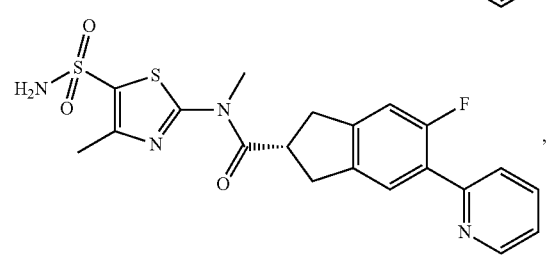

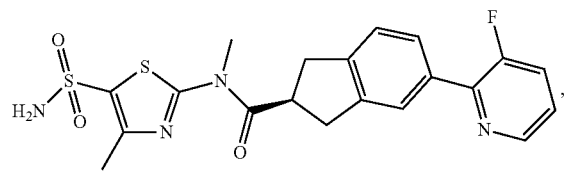

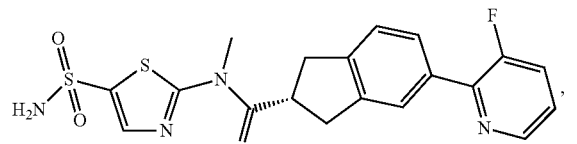

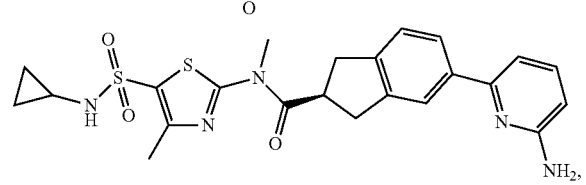

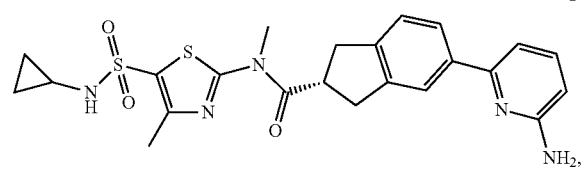

-continued

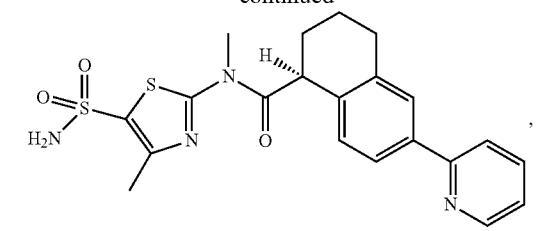

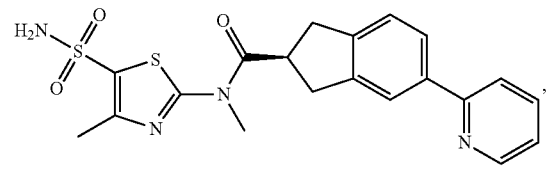

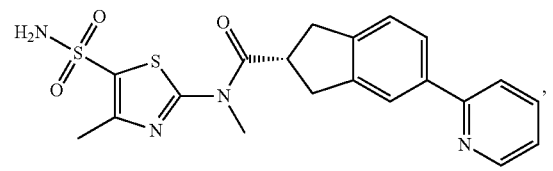

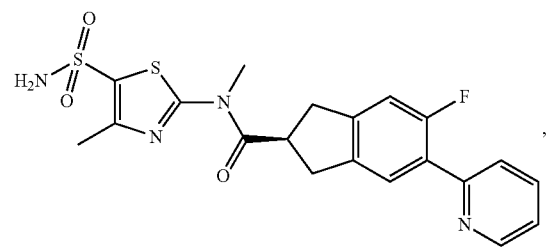

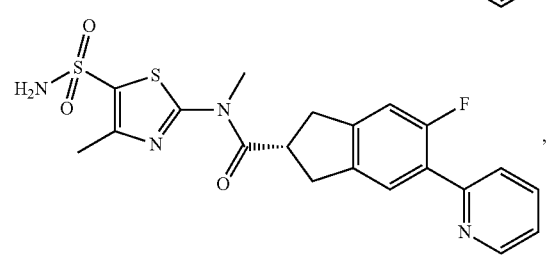, or

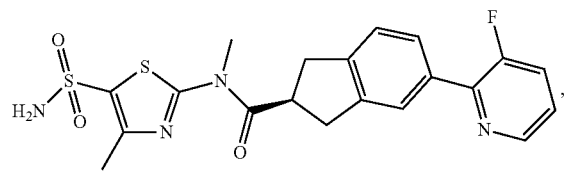.

The present disclosure also provides a pharmaceutical composition, comprising a therapeutically effective amount of the above compound or a pharmaceutically acceptable salt thereof, and a pharmaceutically acceptable carrier.

The present disclosure also provides a use of the above compound or a pharmaceutically acceptable salt thereof in the manufacture of a medicament for treating a disease associated with herpes simplex viruses.

The present disclosure also provides a use of the above pharmaceutical composition in the manufacture of a medicament for treating a disease associated with herpes simplex viruses.

Technical Effects

As a novel thiazole compound, the compound disclosed herein has superior anti-viral activity against herpes simplex virus (HSV); in in vivo pharmacokinetic studies, the compound disclosed herein has lower plasma exposure for the same effective dose, and thus exhibiting better safety.

Definitions and Terms

Unless otherwise indicated, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound disclosed herein that is prepared by reacting the compound having a specific substituent disclosed herein with a relatively non-toxic acid or base. When the compound disclosed herein contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound disclosed herein contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "Pharmaceutical Salts", Journal of Pharmaceutical Science 66: 1-19 (1977)). Certain specific compounds disclosed herein contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound disclosed herein, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided herein also exists in prodrug form. The prodrug of the compound described herein is the compound that readily undergoes chemical change under physiological condition to be converted into the compound disclosed herein. Additionally, the prodrug can be converted to the compound disclosed herein by a chemical or biochemical method in vivo environment.

Certain compounds disclosed herein can exist in an unsolvated form or a solvated form, including a hydrated form. Generally, the solvated form is equivalent to the unsolvated form, and both are encompassed within the scope disclosed herein.

Certain compounds disclosed herein can have an asymmetric carbon atom (optical center) or a double bond. The racemate, diastereomer, geometric isomer and individual isomer are all encompassed within the scope disclosed herein.

Unless otherwise stated, a wedged bond and a dashed bond ( ⫽ ⋯ ) are used to indicate the absolute configuration of a stereocenter, and the wavy line ⌇ is used to indicate the wedged bond and the dashed bond ( ⫽ or ⋯ ). ⫽ and ⋯ are used to indicate the relative configuration of a stereogenic center. When the compound described herein contains an olefinic double bond or other geometric asymmetric centers, E and Z geometric isomers are included unless otherwise specified. Likewise, all tautomeric forms are encompassed within the scope disclosed herein.

The compound disclosed herein may be present in a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope disclosed herein. The substituent such as alkyl may have an additional asymmetric carbon atom. All these isomers and mixtures thereof are encompassed within the scope disclosed herein.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound disclosed herein may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound disclosed herein, whether radioactive or not, are encompassed within the scope disclosed herein.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)0—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to two atoms on a ring, such substituent can be bonded to any atom on the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the moiety

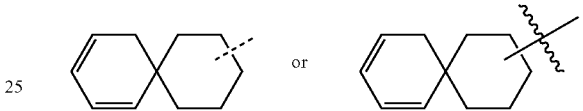

means that it can be substituted at any position on cyclohexyl or cyclohexadiene.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidyl; on the other hand, the term "5-7 membered heterocycloalkyl ring" includes pyridyl and piperidyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)$_p$, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and $S(O)_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuryl, benzomercaptofuryl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H, 6H-1,5,2-dithiazinyl, dihydrofuro[2,3-b]tetrahydrofuryl, furyl, furazanyl, imidazolidinyl, imidazolinyl, imidazolyl, 1H-indazolyl, indolenyl, indolinyl, indolizinyl, indolyl, 3H-indolyl, isobenzofuryl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Fused-ring compounds and spiro compounds are also included.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or hyponyms thereof (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclohydrocarbyl include 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuran-3-yl, tetrahydrothiophen-2-yl, tetrahydrothiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2F$) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom thereof is saturated. Cycloalkyl can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon double bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and s-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridyl, pyrimidinyl, benzothiazolyl, purinyl, benzimidazolyl, indolyl, isoquinolyl, quinoxalinyl, quinolinyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituents described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxymethyl, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound disclosed herein can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment disclosed herein.

All of the solvents used in the present invention are commercially available. The present disclosure employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; r.t. represents room temperature; 0/N represents overnight; THF represents tetrahydrofuran; Boc$_2$O represents di-tert-butyl-dicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; DMAP represents 4-dimethylaminopyridine; Pd(dppf)Cl$_2$ represents [1,1'-bis(diphenylphosphino)ferrocene]palladium dichloride; EDCI represents 1-(3-dimethylaminopropyl)-3-ethylcarbodiimide hydrochloride; HOBt represents 1-hydroxybenzotriazole; NBS represents N-bromosuccinimide; TMSCN represents trimethylsilyl cyanide; HBF$_4$.Et$_2$O represents tetrafluoroboric acid diethyl ether; IPA represents isopropanol.

Compounds are named manually or by ChemDraw® software, the commercially available compounds use their vendor directory names.

DETAILED DESCRIPTION

The present disclosure is illustrated below by the examples, but the present invention is not limited thereto. The present disclosure has been described in detail herein, including the embodiments disclosed herein, and various modifications and changes made to the embodiments disclosed herein, without departing from the spirit and scope of the invention, are obvious to the person skilled in the art.

Reference Example 1: Moiety BB-1

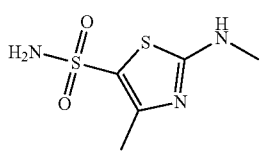

Synthetic route:

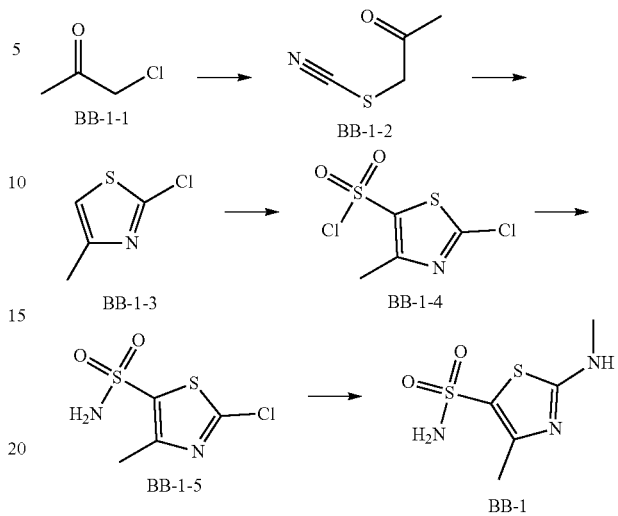

Step 1: Synthesis of Compound BB-1-2

To a solution of chloroacetone (320 g, 3.46 mmol) in 3.5 L of ethanol, sodium thiocyanate (336.31 g, 4.15 mol) was added, and stirred at room temperature for 48 hours. The reaction mixture was filtered, and the filtrate was concentrated under reduced pressure, to afford a crude product. To the crude product 2 L methyl tert-butyl ether was added. After filtration, the filtrate was concentrated under reduced pressure, to afford another crude product, to which 1.5 L methyl tert-butyl ether was added. After filtration, the filtrate was concentrated under reduced pressure, to afford Compound BB-1-2 (390 g, dark brown oil). The product was used in the next reaction directly without purification. $^1$H NMR (400 MHz, CDCl$_3$) δ 4.04 (s, 2H), 2.35 (s, 3H).

Step 2: Synthesis of Compound BB-1-3

BB-1-2 (200 g, 1.74 mol) was dissolved in 3.5 L of dichloromethane, and hydrogen chloride gas was bubbled at 0° C. for 30 minutes. The mixture was stirred at room temperature for 12 hours. The mixture was adjusted to neutral with addition of saturated sodium bicarbonate solution, and extracted with dichloromethane (800 mL×3). The organic phases were combined, and washed sequentially with water (1000 mL×2), and saturated sodium chloride solution (1000 mL×2), and dried over anhydrous sodium sulfate. After filtration, the filtrate was concentrated under reduced pressure, and the residue was purified by silica gel column chromatography using eluent system A, to afford the product BB-1-3 (159 g, yellow oil), yield: 64.9%. $^1$H NMR (400 MHz, CDCl$_3$) δ 6.77 (s, 1H), 2.39 (s, 3H).

Step 3: Synthesis of Compound BB-1-4

Chlorosulfonic acid (249 mL, 3.74 mol) was dissolved in 217 mL thionyl chloride, 2-chloro-4-methylthiazole (100 g, 748.50 mmol) was added, and stirred at 130° C. for 16 hours. The reaction solution was poured into 2 L of ice water, and extracted with methyl tert-butyl ether (500 mL×3). The organic phases were combined, and washed sequentially with water (800 mL×2), saturated sodium chloride solution (800 mL×2), dried over anhydrous sodium sulfate, and filtered, and the filtrate was concentrated under reduced pressure, to afford the product BB-1-4 (170 g, dark brown liquid). The product was used in the next reaction directly without purification. ¹H NMR (400 MHz, CDCl₃) δ 2.77 (s, 3H).

Step 4: Synthesis of Compound BB-1-5

BB-1-4 (110.00 g, 473.91 mmol) was dissolved in 500 mL tetrahydrofuran, aqueous ammonia (140 mL, 947.82 mmol) was added dropwise at 0° C., and stirred at room temperature for 1 hour. The reaction mixture was extracted with ethyl acetate (200 mL×3). The organic phases were combined, washed sequentially with water (50 mL×2), saturated sodium chloride solution (50 mL×2), dried over anhydrous sodium sulfate, and filtered, and the filtrate was concentrated under reduced pressure. The residue was purified by silica gel column chromatography using eluent system A, to afford the product BB-1-5 (72 g, yellow solid), yield: 71.43%. ¹H NMR (400 MHz, DMSO-d6) δ 8.03 (s, 2H), 2.29 (d, J=1.2 Hz, 3H).

Step 5: Synthesis of Compound BB-1

BB-1-5 (20 g, 94.04 mmol) and 28% aqueous methylamine solution (41.73 g, 37.16 mmol) were added to 100 mL tetrahydrofuran, heated to 50° C. to react for 4 hours, until the reaction was complete. The reaction mixture was concentrated to dry, and the residue was purified by silica gel column chromatography using eluent system A, to afford the product BB-1 (18 g, yellow solid), yield: 92.35%. ¹H NMR (400 MHz, DMSO-d6) δ 2.79 (d, J=4.8 Hz, 3H), 2.29 (s, 3H).

Reference Example 2: Moiety BB-2

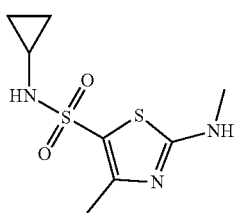

Synthetic Route:

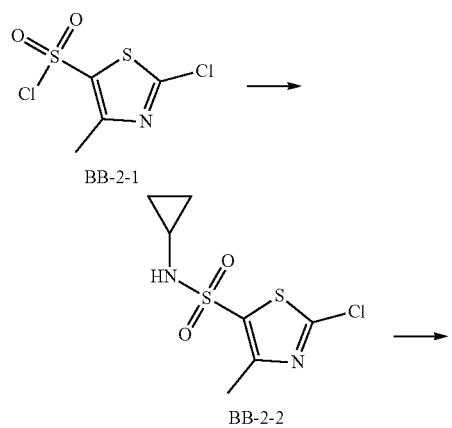

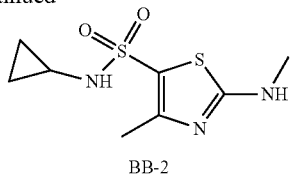

BB-2

Step 1: Synthesis of Compound BB-2-2

At 0° C., to a solution of 2-chloro-4-methylthiazol-5-sulfonyl chloride (50.00 g, 215.42 mmol) in dichloromethane (800.00 mL) triethylamine (43.60 g, 430.84 mmol) and cyclopropylamine (18.45 g, 323.13 mmol) were added, and the system was stirred at 20° C. for 10 mins After the reaction was complete, 200 mL water was added to the system. The organic layer was washed separately with 3 M aqueous sodium hydrogen sulfate solution (300 mL×2) and brine (300 mL), dried over anhydrous sodium sulfate, filtered and concentrated under reduced pressure to afford the product BB-2-2 (33.00 g, crude product), dark grey solid, which was used in the next reaction directly. ¹H NMR (400 MHz, CDCl₃) δ 5.23-5.32 (m, 1H), 2.64, (s, 3H), 2.35-2.48 (m, 1H), 0.68-0.75 (m, 4H).

Step 2: Synthesis of Compound BB-2

At 20° C., to a solution of BB-2-2 (13.00 g, 51.44 mmol) in tetrahydrofuran (100.00 mL) was added aqueous methylamine solution (61.45 g, 514.36 mmol, 26% purity), and the system was stirred at 80° C. for 16 hours. After the reaction was complete, the system was concentrated under reduced pressure. The residue was added to 500 mL petroleum ether and 60 mL ethyl acetate, stirred for 10 mins, and the solid was filtered. The filter cake was dried to afford the product BB-2 (11.00 g, 86.45% yield), dark brown solid. ¹H NMR (400 MHz, DMSO-d6) δ 8.14 (d, J=4.77 Hz, 1H), 7.81 (d, J=2.51 Hz, 1H), 2.80 (d, J=4.77 Hz, 3H), 2.30 (s, 3H), 2.15-2.22 (m, 1H), 0.51 (s, 2H), 0.41 (d, J=3.26 Hz, 2H).

Example 1: WX042

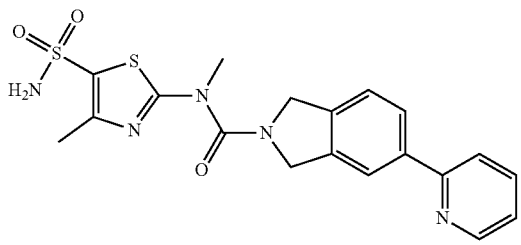 [SMILES: Cc1nc(N(C)C(=O)N2Cc3ccc(-c4ccccn4)cc3C2)sc1S(N)(=O)=O]

Synthetic Route:

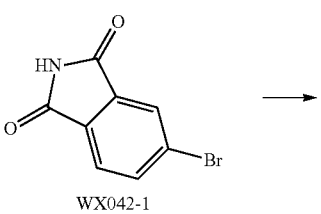

WX042-1

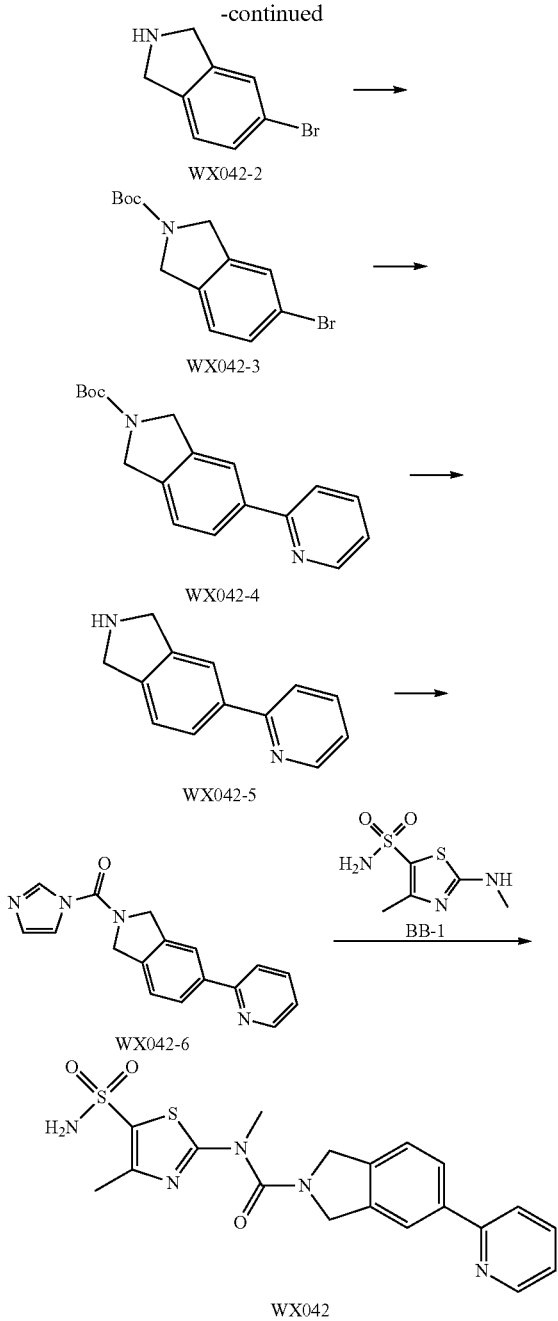

Step 1: Synthesis of Compound WX042-2

Under a nitrogen atmosphere, at 0° C., to a solution of WX042-1 (5.00 g, 22.12 mmol) in tetrahydrofuran (50.00 mL) was added borane dimethyl sulfide (10 M, 11.06 mL) dropwise, and the system was stirred at 70° C. for 16 hours. After the reaction was complete, at 0° C. to the system was added 100 mL methanol to quench the reaction system. After concentration under reduced pressure, the residue was purified by column chromatography (dichloromethane:methanol=20:1) to afford Compound WX042-2 (1.00 g, 22.16% yield, 97.1% purity), white solid. $^1$H NMR (400 MHz, DMSO-d6) δ 7.43 (s, 1H), 7.40-7.34 (m, 2H), 7.11 (d, J=8.5 Hz, 1H), 4.48 (d, J=16.6 Hz, 4H).

Step 2: Synthesis of Compound WX042-3

At 20° C., to a system of WX042-2 (5.00 g, 22.12 mmol) and Boc$_2$O (1.21 g, 5.56 mmol) in N, N-dimethylformamide (10.00 mL) was added DMAP (61.70 mg, 505.00 μmol), and the system was stirred at 20° C. for 12 hours. After the reaction was complete, the system was extracted with ethyl acetate (15 mL×3). The organic layer was washed separately with water (10 mL×3) and brine (10 mL×2), dried over anhydrous sodium sulfate, and concentrated under reduced pressure. The residue was purified by column chromatography (petroleum ether:ethyl acetate=5:1) to afford Compound WX042-3 (900.00 mg, 59.80% yield), white solid. $^1$H NMR (400 MHz, CDCl$_3$) δ 7.42-7.36 (m, 2H), 7.17-7.08 (m, 1H), 4.67-4.59 (m, 4H), 1.51 (s, 9H).

Step 3: Synthesis of Compound WX042-4

Under a nitrogen atmosphere, the system of WX042-3 (800.00 mg, 2.68 mmol), tri-tert-butyl(2-pyridyl)stannane (1.18 g, 3.22 mmol) and tetrakis(triphenylphosphine)palladium (154.85 mg, 134.00 μmol) in toluene (10.00 mL) was stirred at 110° C. for 4 hours. After the reaction was complete, it was concentrated under reduced pressure. The residue was purified by column chromatography (petroleum ether:ethyl acetate=10: 1-3:1) to afford Compound WX042-4 (580.00 mg, 73.03% yield), white solid. $^1$H NMR (400 MHz, CDCl$_3$) δ 8.69 (d, J=4.8 Hz, 1H), 7.95-7.85 (m, 2H), 7.79-7.68 (m, 2H), 7.35 (dd, J=7.9, 19.7 Hz, 1H), 7.26-7.21 (m, 1H), 4.80-4.66 (m, 4H), 1.53 (s, 9H).

Step 4: Synthesis of Compound WX042-5

At 0° C., to a system of WX042-4 (580.00 mg, 1.96 mmol) in dichloromethane (8.00 mL) was added trifluoroacetic acid (1.12 g, 9.80 mmol) dropwise, and the system was stirred at 20° C. for 1 hour. After the reaction was complete, it was concentrated under reduced pressure. The residue was dissolved in 10 mL dichloromethane, and the system was adjusted to neutral with sodium carbonate. The system was concentrated under reduced pressure. The residue was purified by column chromatography (dichloromethane:methanol=5:1) to afford Compound WX042-5 (300.00 mg, 78.06% yield), white solid. $^1$H NMR (400 MHz, CD$_3$OD) δ 8.64 (d, J=4.8 Hz, 1H), 8.03-7.87 (m, 4H), 7.55 (d, J=8.0 Hz, 1H), 7.40-7.43 (m, 1H), 4.68 (d, J=8.3 Hz, 4H).

Step 5: Synthesis of Compound WX042-6

Under a nitrogen atmosphere, at 0° C., to a solution of CDI (99.15 mg, 611.46 μmol) in tetrahydrofuran (3.00 mL) was added WX042-5 (100.00 mg, 509.55 μmol) and triethylamine (51.56 mg, 509.55 μmol), and the system was stirred at 20° C. for 2 hours, until the reaction was complete. It was concentrated under reduced pressure. The residue was purified by column chromatography (dichloromethane:methanol=20:1) to afford Compound WX042-6 (120.00 mg, crude product), white solid. $^1$H NMR (400 MHz, CD$_3$OD) δ 8.66-8.60 (m, 1H), 8.33 (s, 1H), 8.17 (s, 1H), 7.96-7.92 (m, 2H), 7.91-7.86 (m, 1H), 7.74 (t, J=1.4 Hz, 1H), 7.54-7.44 (m, 1H), 7.39 (m, 1H), 7.15 (d, J=1.0 Hz, 1H), 5.12 (d, J=8.8 Hz, 4H).

Step 6: Synthesis of Compound WX042

Under a nitrogen atmosphere, at 15° C., to a solution of WX042-6 (80.00 mg, 275.56 μmol) and BB-1 (57.11 mg, 275.56 μmol) in toluene (10.00 mL) was added trimethyl-aluminium (1 M, 826.68 μL), and the system was stirred at 110° C. for 2 hours, until the reaction was complete. At 0° C., to the system was added 10 mL methanol to quench the reaction, and the system was filtered. The filtrate was concentrated under reduced pressure. The residue was purified by preparative chromatography to afford Compound WX042 (1.70 mg, 1.15% yield, 100% purity). $^{1}$H NMR (400 MHz, DMSO-d6) δ 8.65 (d, J=4.0 Hz, 1H), 8.07 (s, 1H), 8.03 (d, J=8.0 Hz, 1H), 7.97-7.93 (m, 1H), 7.91-7.85 (m, 1H), 7.57 (s, 2H), 7.45 (d, J=8.0 Hz, 1H), 7.35 (dd, J=5.1, 6.9 Hz, 1H), 4.96 (d, J=6.3 Hz, 4H), 3.58 (s, 2H), 2.48 (s, 3H).

Example 2: WX076

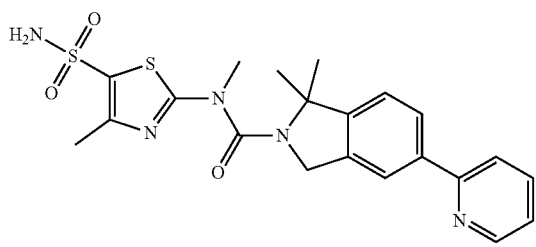 [SMILES: Cc1nc(N(C)C(=O)N2Cc3cc(-c4ccccn4)ccc3C2(C)C)sc1S(N)(=O)=O]

Synthetic Route:

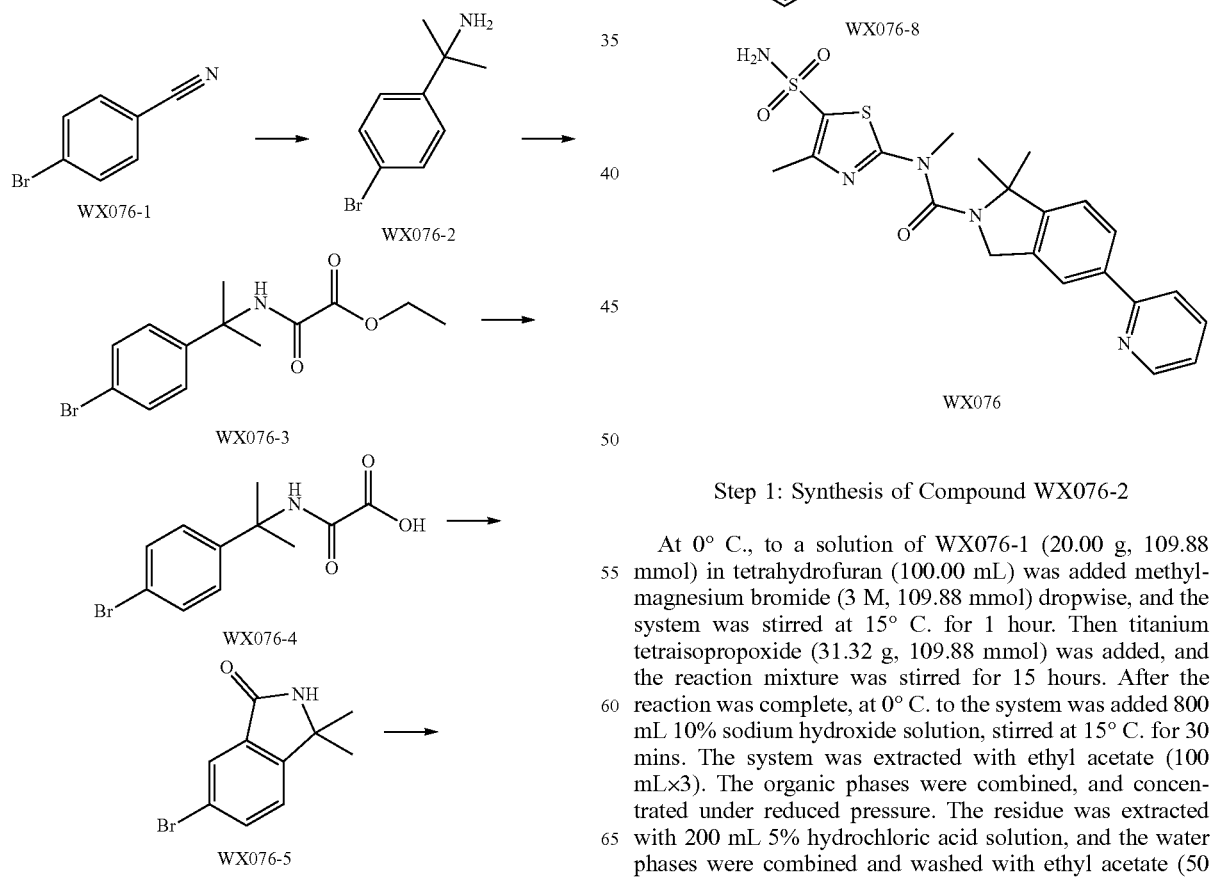

Step 1: Synthesis of Compound WX076-2

At 0° C., to a solution of WX076-1 (20.00 g, 109.88 mmol) in tetrahydrofuran (100.00 mL) was added methylmagnesium bromide (3 M, 109.88 mmol) dropwise, and the system was stirred at 15° C. for 1 hour. Then titanium tetraisopropoxide (31.32 g, 109.88 mmol) was added, and the reaction mixture was stirred for 15 hours. After the reaction was complete, at 0° C. to the system was added 800 mL 10% sodium hydroxide solution, stirred at 15° C. for 30 mins. The system was extracted with ethyl acetate (100 mL×3). The organic phases were combined, and concentrated under reduced pressure. The residue was extracted with 200 mL 5% hydrochloric acid solution, and the water phases were combined and washed with ethyl acetate (50 mL×2), and adjusted to pH of 14 with 20% sodium hydroxide solution, and extracted with ethyl acetate (150 mL×3). The organic phases were combined and washed with brine (100 mL×3), dried over anhydrous sodium sulfate, and concentrated to afford Compound WX076-2 (17.00 g, crude product), yellow oil. $^1$H NMR (400 MHz, CDCl$_3$) δ 7.36-7.47 (m, 4H), 1.47 (s, 6H).

Step 2: Synthesis of Compound WX076-3

Under a nitrogen atmosphere, at 0° C., to a solution of WX076-2 (16.30 g, 76.13 mmol), triethylamine (15.41 g, 152.26 mmol) in dichloromethane (200.00 mL) was added oxalyl chloride monoethyl ester (41.58 g, 304.52 mmol) dropwise, and the system was stirred at 15° C. for 0.5 hour. After the reaction was complete, to the system was added 100 mL dichloromethane, and the reaction mixture was washed with 10% hydrochloric acid solution. The water layers were combined, extracted with dichloromethane (75 mL×3), and the organic phase was washed with brine (100 mL×3), dried over anhydrous sodium sulfate, filtered and concentrated. The residue was purified by column chromatography (petroleum ether:ethyl acetate=100:0-0:100) to afford Compound WX076-3 as a yellow oil. $^1$H NMR (400 MHz, CDCl$_3$) δ 7.46 (d, J=8.53 Hz, 3H), 7.28 (d, J=8.53 Hz, 2H), 4.33 (q, J=7.03 Hz, 2H), 1.74 (s, 6H), 1.39 (t, J=7.03 Hz, 3H).

Step 3: Synthesis of Compound WX076-4

To a solution of WX076-3 (21.00 g, 66.84 mmol) in ethanol (100.00 mL) was added a solution of sodium hydroxide (8.02 g, 200.52 mmol) in water (50.00 mL), and the system was stirred at 15° C. for 1 hour. After the reaction was complete, the system was adjusted to pH=2-3 with 1M hydrochloric acid solution, and extracted with ethyl acetate (100 mL×3). The organic phase was washed with brine (50 mL×3), dried over anhydrous sodium sulfate, filtered and concentrated to afford Compound WX076-4, white solid. $^1$H NMR (400 MHz, CDCl$_3$) δ 7.90-8.50 (m, 1H), 7.67 (br. s., 1H), 7.47 (d, J=8.53 Hz, 2H), 7.24 (d, J=8.53 Hz, 2H), 1.73 (s, 6H).

Step 4: Synthesis of Compound WX076-5

To a solution of WX076-4 (5.00 g, 17.48 mmol) in dimethyl sulfoxide (250.00 mL) was added Na$_2$S$_2$O$_8$ (8.32 g, 34.96 mmol), and the system was stirred at 110° C. for 36 hours. After the reaction was complete, the system was poured into 500 mL saturated aqueous sodium carbonate solution, extracted with ethyl acetate (150 mL×3). The organic layers were combined, washed separately with water (150 mL×3) and brine (150 mL×3), dried over anhydrous sodium sulfate, filtered and concentrated. The residue was purified by column chromatography (petroleum ether:ethyl acetate=10:90-0:100) to afford Compound WX076-5, yellow oil. $^1$H NMR (400 MHz, CDCl$_3$) δ 7.94 (d, J=1.25 Hz, 1H), 7.68 (dd, J=1.51, 8.03 Hz, 1H), 7.28 (d, J=8.03 Hz, 1H), 6.42 (br. s., 1H), 1.54 (s, 6H).

Step 5: Synthesis of Compound WX076-6

A solution of WX076-5 (1.50 g, 6.25 mmol) and tri-tert-butyl(2-pyridyl)stannane (3.45 g, 9.37 mmol) in toluene (10.00 mL) was purged with nitrogen gas for three times, and then to the reaction mixture was added tetrakis(triphenylphosphine)palladium (721.92 mg, 624.74 μmol). The system was stirred at 110° C. under a nitrogen atmosphere for 3 hours. After the reaction was complete, it was concentrated under reduced pressure. The residue was purified by preparative chromatography to afford Compound WX076-6, white solid. $^1$H NMR (400 MHz, CDCl$_3$) δ 8.73 (d, J=4.52 Hz, 1H), 8.33-8.41 (m, 2H), 7.76-7.86 (m, 2H), 7.54 (d, J=8.53 Hz, 1H), 7.25-7.32 (m, 1H), 7.15 (br. s., 1H), 1.62 (s, 6H).

Step 6: Synthesis of Compound WX076-7

To a solution of WX076-6 (112.00 mg, 470.04 μmol) in tetrahydrofuran (5.00 mL) was added lithium aluminum hydride (26.76 mg, 705.05 μmol). The system was stirred at 70° C. for 20 hours. After the reaction was complete, to the system was added 50 mL water. The mixture was extracted with ethyl acetate (50 mL×3). The organic layers were combined, and washed with 50 mL brine, dried over anhydrous sodium sulfate, filtered and concentrated. The residue was purified with thin layer chromatography (dichloromethane:methanol=10:1) to afford Compound WX076-7, yellow oil. $^1$H NMR (400 MHz, CDCl$_3$) δ 8.69 (d, J=4.52 Hz, 1H), 7.92-8.00 (m, 2H), 7.75-7.83 (m, 1H), 7.67-7.73 (m, 1H), 7.27-7.29 (m, 1H), 7.26 (br. s., 1H), 4.72 (s, 2H), 1.87 (s, 6H).

Step 7: Synthesis of Compound WX076-8

Under a nitrogen atmosphere, at 20° C., to a solution of CDI (34.70 mg, 214.00 μmol) in tetrahydrofuran (5.00 mL) were added Compound WX076-7 (40.00 mg, 178.33 μmol) and triethylamine (18.05 mg, 178.33 μmol). The reaction system was reacted under reflux for 20 hours. After the reaction was complete, it was concentrated under reduced pressure. The residue was dissolved in 50 mL water. The system was extracted with ethyl acetate (50 mL×3). The organic layers were combined and washed separately with 50 mL brine and 50 mL water, dried over anhydrous sodium sulfate, filtered and concentrated to afford Compound WX076-8, white solid. $^1$H NMR (400 MHz, CDCl$_3$) δ 8.70 (d, J=4.27 Hz, 1H), 8.06 (br. s., 1H), 7.97 (d, J=8.28 Hz, 1H), 7.87 (s, 1H), 7.78 (s, 1H), 7.68-7.73 (m, 1H), 7.39 (br. s., 1H), 7.33 (d, J=8.03 Hz, 1H), 7.16 (br. s., 1H), 4.99 (s, 2H), 1.89 (s, 4H).

Step 8: Synthesis of Compound WX076

Under a nitrogen atmosphere, at 15° C., to a solution of WX076-8 (50.00 mg, 157.05 μmol) and BB-1 (32.55 mg, 157.05 μmol) in toluene (5.00 mL) was added trimethylaluminium (2 M, 235.57 μL). The reaction system was reacted at 110° C. for 4 hours. After the reaction was complete, it was concentrated under reduced pressure. The residue was dissolved in 50 mL dichloromethane. The system was washed separately with 25 mL brine and 25 mL water, dried over anhydrous sodium sulfate, filtered and concentrated. The residue was purified by preparative chromatography to afford Compound WX076. $^1$H NMR (400 MHz, CD$_3$OD) 8.61-8.65 (m, 1H), 8.48-8.53 (m, 1H), 7.86-7.98 (m, 4H), 7.42-7.46 (m, 1H), 7.38-7.41 (m, 1H), 4.98-5.01 (m, 3H), 3.44-3.49 (m, 3H), 2.48-2.52 (m, 2H), 1.79-1.94 (m, 6H).

Example 3: WX128

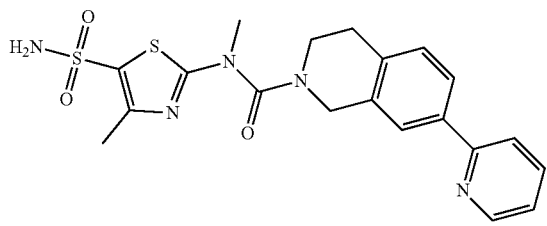 [SMILES: Cc1nc(N(C)C(=O)N2CCc3ccc(-c4ccccn4)cc3C2)sc1S(N)(=O)=O]

Synthetic Route:

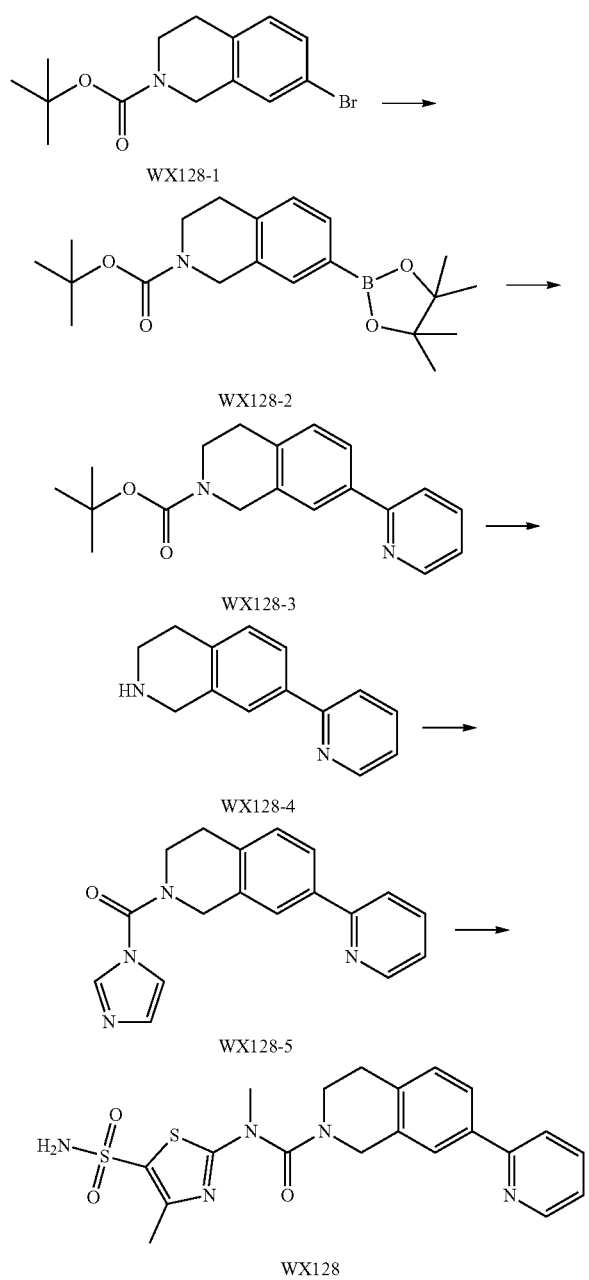

Step 1: Synthesis of Compound WX128-2

A solution of WX128-1 (2.00 g, 6.41 mmol), bis(Pinacolato)Diboron (1.79 g, 7.05 mmol) and potassium acetate (1.89 g, 19.22 mmol) in dioxane (20.00 mL) was purged with nitrogen gas for three times, and then to the system was added Pd(dppf)Cl$_2$ (1.41 g, 1.92 mmol). The reaction mixture was reacted at 80° C. under a nitrogen atmosphere for 15 hours. After the reaction was complete, it was concentrated under reduced pressure. The residue was dissolved in 30 mL water, and extracted with ethyl acetate (30 mL×3). The organic layers were combined, and washed with brine (50 mL×3), dried over anhydrous sodium sulfate, filtered and concentrated to afford Compound WX128-2 (3.38 g, crude product), dark brown oil. $^1$H NMR (400 MHz, CDCl$_3$) δ 7.63-7.54 (m, 2H), 7.15 (d, J=7.5 Hz, 1H), 4.59 (s, 2H), 3.65 (br s, 2H), 2.85 (br s, 2H), 1.49 (s, 9H), 1.35 (s, 12H).

Step 2: Synthesis of Compound WX128-3

Under a nitrogen atmosphere, at 25° C., to a solution of WX128-2 (2.88 g, 8.02 mmol), and 2-bromopyridine (1.27 g, 8.02 mmol, 763.35 μL) in dioxane (30.00 mL) and water (7.50 mL) were added sodium carbonate (1.02 g, 9.62 mmol) and tetrakis(triphenylphosphine)palladium (185.35 mg, 160.40 μmol). The reaction mixture was reacted at 100° C. under a nitrogen atmosphere for 15 hours. After the reaction was complete, it was concentrated under reduced pressure. The residue was purified by column chromatography to afford Compound WX128-3 (1.83 g, 62.88% yield), white solid. $^1$H NMR (400 MHz, CDCl$_3$) 7.63-7.54 (m, 2H), 7.15 (d, J=7.5 Hz, 1H), 4.59 (s, 2H), 3.65 (br s, 2H), 2.85 (br s, 2H), 1.49 (s, 9H), 1.35 (s, 12H). $^1$H NMR (400 MHz, CDCl$_3$) δ 8.69 (d, J=4.8 Hz, 1H), 7.84-7.68 (m, 4H), 7.27-7.21 (m, 2H), 4.68 (s, 2H), 3.69 (br s, 2H), 2.90 (br t, J=5.5 Hz, 2H), 1.51 (s, 9H).

Step 3: Synthesis of Compound WX128-4

Under a nitrogen atmosphere, at 0° C., to a solution of WX128-3 (1.83 g, 5.90 mmol) in dichloromethane (20.00 mL) was added trifluoroacetic acid (10.00 mL) dropwise. The reaction mixture was reacted at 25° C. for 20 mins After the reaction was complete, it was concentrated under reduced pressure. The residue was diluted with 20 mL dichloromethane. The system was adjusted to pH=8-9 with saturated aqueous sodium carbonate solution, extracted with dichloromethane (20 mL×3). The organic layers were combined and washed with brine (25 mL×2), dried over anhydrous sodium sulfate, filtered and concentrated to afford Compound WX128-4 (1.09 g, 87.86% yield). $^1$H NMR (400 MHz, CDCl$_3$) δ 8.68 (d, J=4.8 Hz, 1H), 7.77-7.67 (m, 4H), 7.25-7.16 (m, 2H), 4.12 (s, 2H), 3.19 (t, J=6.0 Hz, 2H), 2.86 (t, J=5.9 Hz, 2H).

Step 4: Synthesis of Compound WX128-5

Under a nitrogen atmosphere, at 25° C., to a solution of WX128-4 (300.00 mg, 1.43 mmol) in toluene (5.00 mL) was added CDI (255.06 mg, 1.57 mmol). The system was stirred at 80° C. for 15 hours. After the reaction was complete, 15 mL water was added to quench the reaction. The mixture was diluted with 20 mL ethyl acetate. The system was extracted with ethyl acetate (20 mL×3). The organic layers were combined and washed with 50 mL brine, dried over anhydrous sodium sulfate, filtered and concentrated. The residue was purified by column chromatography to afford Compound WX128-5 (327.00 mg, crude product), yellow oil. $^1$H NMR (400 MHz, CDCl$_3$) δ 8.71-8.67 (m, 1H), 7.97 (s, 1H), 7.86-7.67 (m, 4H), 7.34-7.28 (m, 2H), 7.27-7.23 (m, 1H), 7.13 (d, J=9.8 Hz, 1H), 4.86 (s, 2H), 3.88 (t, J=5.9 Hz, 2H), 3.08 (t, J=5.9 Hz, 2H).

Step 5: Synthesis of Compound WX128

Under a nitrogen atmosphere, at 25° C., to a solution of WX128-5 (100.00 mg, 328.57 μmol) and BB-1 (68.10 mg, 328.57 μmol) in toluene (5.00 mL) was added trimethylaluminium (1 M, 985.71 μL) dropwise. The reaction system was reacted at 110° C. for 2 hours. After the reaction was complete, at 25° C. to the system was added 2 mL 1M diluted hydrochloric acid to quench the reaction. The mixture was concentrated under reduced pressure. The residue was purified by preparative chromatography to afford Compound WX128 (23.80 mg, 16.33% yield). $^1$H NMR (400 MHz, DMSO-d6) δ 8.75 (br d, J=4.8 Hz, 1H), 8.24-8.09 (m, 2H), 7.95 (s, 1H), 7.92 (d, J=8.3 Hz, 1H), 7.69-7.48 (m, 3H), 7.39 (d, J=8.0 Hz, 1H), 4.66 (s, 2H), 3.65 (br t, J=5.6 Hz, 2H), 3.51 (s, 3H), 3.00 (br t, J=5.4 Hz, 2H), 2.43 (s, 3H).

Example 4: WX135

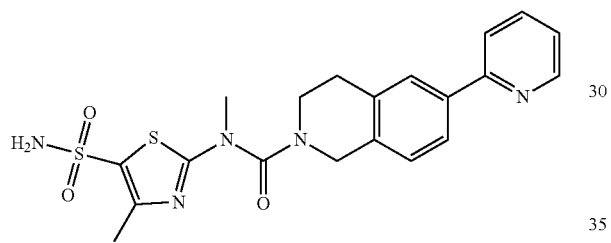

Synthetic Route:

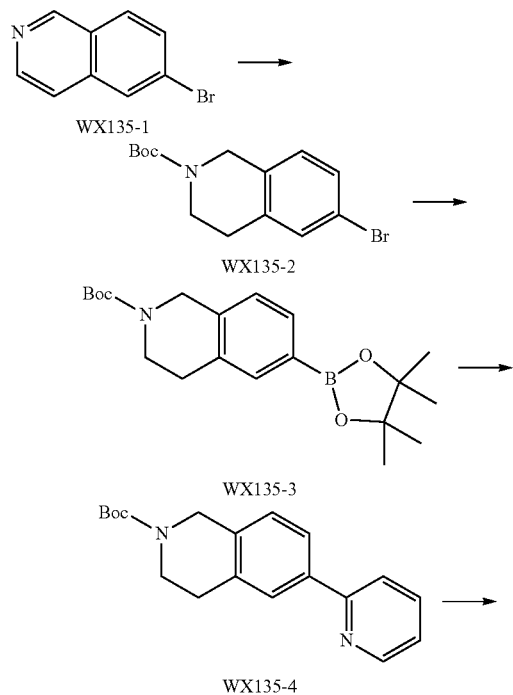

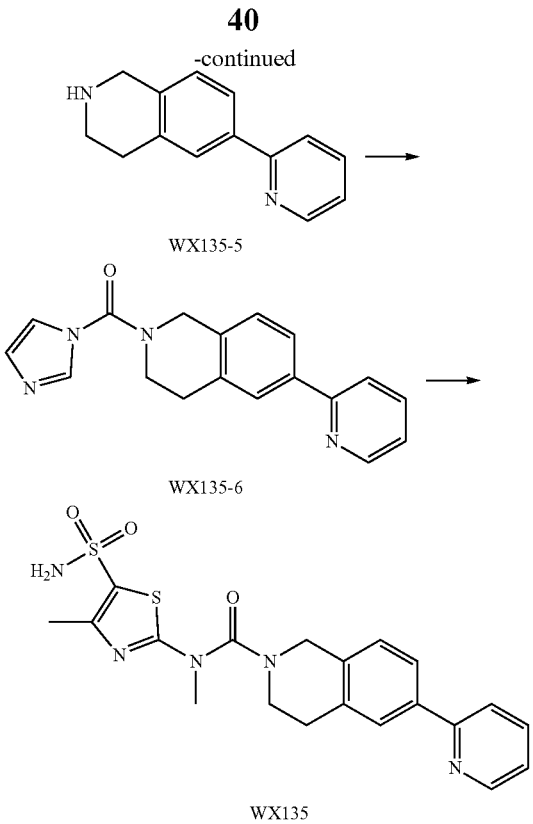

Step 1: Synthesis of Compound WX135-2

Under a nitrogen atmosphere, at 0° C., to a solution of WX135-1 (2.00 g, 9.61 mmol) in tetrahydrofuran (20.00 mL) was added lithium triethylborohydride (1 M, 42.28 mL) dropwise, and the system was reacted at 25° C. for 2 hours. After the reaction was complete, the system was firstly adjusted to pH=2-3 with 1M diluted hydrochloric acid, and then adjusted to pH=9-10 with sodium carbonate solution. At 0° C., to the system was added Boc$_2$O (4.19 g, 19.22 mmol, 4.42 mL), and the reaction mixture was stirred at 25° C. for 15 hours. After the reaction was complete, at 25° C., to the reaction system was added 100 mL water. The system was diluted with 100 mL ethyl acetate, and extracted with ethyl acetate (100 mL×3). The organic layers were combined, washed with brine (150 mL×2), dried over anhydrous sodium sulfate, filtered, and concentrated under reduced pressure. The residue was purified by column chromatography (petroleum ether:ethyl acetate=100:1-50:1) to afford Compound WX135-2 (2.42 g, 70.14% yield), colorless oil. $^1$H NMR (400 MHz, CDCl$_3$) δ 7.33-7.29 (m, 2H), 6.99 (br d, J=8.0 Hz, 1H), 4.52 (s, 2H), 3.63 (br s, 2H), 2.81 (br t, J=5.6 Hz, 2H), 1.50 (s, 9H).

Step 2: Synthesis of Compound WX135-3

Synthesis of Compound WX135-3 was carried out by referring to the synthetic method of Example 3 Step 1, $^1$H NMR (400 MHz, CDCl$_3$) δ 7.65-7.58 (m, 2H), 7.13 (br d, J=7.5 Hz, 1H), 4.59 (s, 2H), 3.64 (br s, 2H), 2.85 (br s, 2H), 1.49 (s, 9H), 1.36-1.33 (m, 12H).

Step 3: Synthesis of Compound WX135-4

Synthesis of Compound WX135-4 was carried out by referring to the synthetic method of Example 3 Step 2, $^1$H NMR (400 MHz, CDCl₃) δ 8.69 (d, J=4.5 Hz, 1H), 7.85-7.68 (m, 4H), 7.26-7.18 (m, 2H), 4.64 (s, 2H), 3.69 (br s, 2H), 2.94 (br t, J=5.3 Hz, 2H), 1.51 (s, 9H).

Step 4: Synthesis of Compound WX135-5

Synthesis of Compound WX135-5 was carried out by referring to the synthetic method of Example 3 Step 3, ¹H NMR (400 MHz, DMSO-d6) δ 8.63 (d, J=4.8 Hz, 1H), 7.93-7.89 (m, 1H), 7.85 (dd, J=1.6, 7.4 Hz, 1H), 7.83-7.78 (m, 2H), 7.34-7.26 (m, 1H), 7.16-7.05 (m, 1H), 3.88 (s, 2H), 3.01-2.93 (m, 2H), 2.81-2.72 (m, 2H).

Step 5: Synthesis of Compound WX135-6

Synthesis of Compound WX135-6 was carried out by referring to the synthetic method of Example 3 Step 4, ¹H NMR (400 MHz, DMSO-d6) δ 8.66 (d, J=4.0 Hz, 1H), 8.13 (s, 1H), 7.96 (br d, J=5.0 Hz, 2H), 7.94 (br d, J=8.0 Hz, 1H), 7.91-7.85 (m, 1H), 7.58 (s, 1H), 7.38-7.31 (m, 2H), 7.08 (s, 1H), 4.77 (s, 2H), 3.75 (t, J=5.8 Hz, 2H), 3.05 (t, J=5.6 Hz, 2H).

Step 6: Synthesis of Compound WX135

Synthesis of Compound WX135 was carried out by referring to the synthetic method of Example 3 Step 5, ¹H NMR (400 MHz, DMSO-d6) 8.76 (d, J=5.0 Hz, 1H), 8.25 (br s, 1H), 8.21-8.15 (m, 1H), 7.94 (s, 1H), 7.91 (br d, J=8.0 Hz, 1H), 7.67 (br s, 1H), 7.57 (br s, 2H), 7.41 (d, J=8.3 Hz, 1H), 4.64 (s, 2H), 3.65 (br t, J=5.6 Hz, 2H), 3.50 (s, 3H), 3.02 (br t, J=5.5 Hz, 2H), 2.43 (s, 3H).

Example 5: WX027

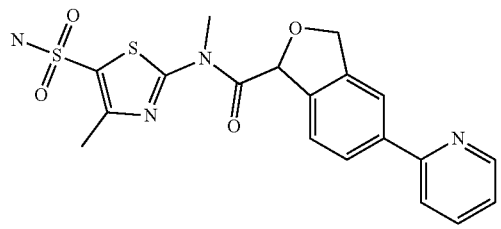 [SMILES: Cc1nc(N(C)C(=O)C2OCc3cc(-c4ccccn4)ccc32)sc1S(N)(=O)=O]

Synthetic Route:

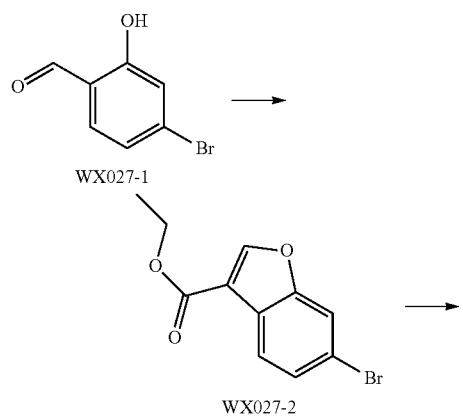

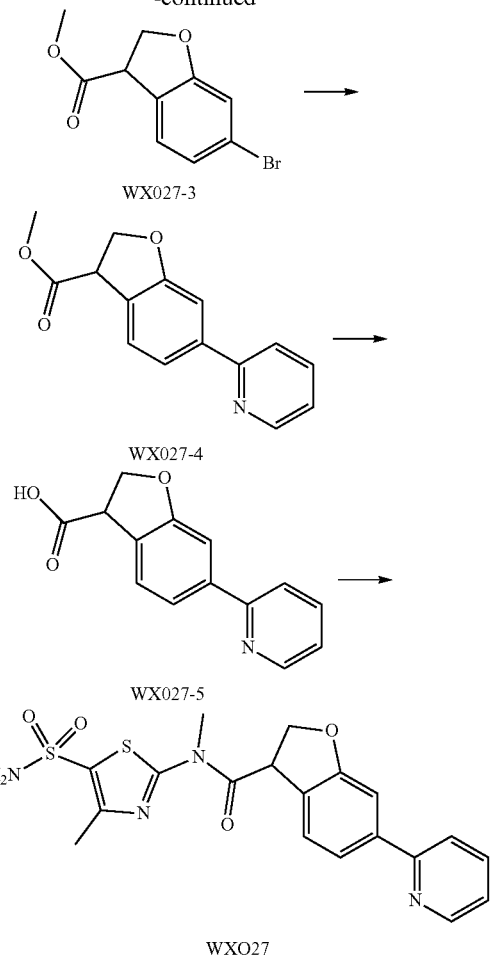

Step 1: Synthesis of Compound WX027-2

To a solution of WX027-1 (4.00 g, 19.90 mmol) in dichloromethane (35.00 mL) was added HBF₄·Et₂O (322.24 mg, 1.99 mmol), and the system turned black. Then a solution of ethyl diazoacetate (5.45 g, 47.77 mmol) in dichloromethane (5.00 mL) was added dropwise. The reaction temperature was maintained to below 38° C., and the system was stirred at 20° C. for 1 hours. The reaction mixture was concentrated under reduced pressure at 20° C., and 2 mL sulphuric acid was added dropwise. The reaction mixture was stirred for 1 hours. After the reaction was complete, the reaction mixture was poured into 30 mL ice water, and extracted with dichloromethane (30 mL×3). The organic layers were combined, and washed separately with 5% sodium bicarbonate (20 mL×2) and brine (150 mL×2), dried over anhydrous sodium sulfate, filtered, and concentrated under reduced pressure. The residue was purified by column chromatography (petroleum ether:ethyl acetate=3:1) to afford Compound WX027-2 (3.00 g, 56.02% yield), light yellow solid. ¹H NMR (400 MHz, CDCl₃) δ 8.22 (s, 1H), 7.93 (d, J=8.3 Hz, 1H), 7.71 (d, J=1.3 Hz, 1H), 7.48 (dd, J=1.5, 8.3 Hz, 1H), 4.41 (q, J=7.0 Hz, 2H), 1.42 (t, J=7.2 Hz, 3H).

Step 2: Synthesis of Compound WX027-3

At 20° C., to a solution of WX027-2 (400.94 mg, 1.49 mmol) in methanol (10.00 mL) was added magnesium (181.11 mg, 7.45 mmol), and the system was stirred at 20° C. for 3 hours. After the reaction was complete, the reaction mixture was poured into 30 mL ice water, and 30 mL ethyl acetate was added, and the reaction mixture was stirred at 20° C. for 30 mins, and filtered. The filtrate was extracted with ethyl acetate (20 mL×3). The organic layers were combined, washed separately with water (20 mL×3) and brine (15 mL×3), dried over anhydrous sodium sulfate, filtered, and concentrated under reduced pressure to afford Compound WX027-3 (260.00 mg, 67.79% yield), white solid.

$^1$H NMR (400 MHz, CDCl$_3$) δ 7.38 (d, J=7.3 Hz, 1H), 6.89 (t, J=7.4 Hz, 1H), 6.83 (d, J=8.0 Hz, 1H), 5.01-4.90 (m, 1H), 4.75-4.60 (m, 1H), 4.35 (dd, J=6.8, 9.8 Hz, 1H), 3.78 (s, 3H).

Step 3: Synthesis of Compound WX027-4

A solution of WX027-3 (200.00 mg, 737.71 μmol) and tri-tert-butyl(2-pyridyl)stannane (407.37 mg, 1.11 mmol) in toluene (10.00 mL) was purged with nitrogen gas for three times, and then to the reaction mixture was added tetrakis(triphenylphosphine)palladium (42.62 mg, 36.89 μmol), and the system was stirred at 110° C. under a nitrogen atmosphere for 5 hours. After the reaction was complete, it was concentrated under reduced pressure. The residue was purified by preparative chromatography (petroleum ether:ethyl acetate=3:1) to afford Compound WX027-4 (90.00 mg, 40.77% yield), white solid. $^1$H NMR (400 MHz, CDCl$_3$) 8.70-8.64 (m, 1H), 7.76-7.64 (m, 2H), 7.57-7.52 (m, 1H), 7.48-7.43 (m, 2H), 7.23 (m, 1H), 4.99 (dd, J=6.5, 9.3 Hz, 1H), 4.74 (t, J=9.5 Hz, 1H), 4.39 (dd, J=6.5, 9.5 Hz, 1H), 3.80 (s, 3H).

Step 4: Synthesis of Compound WX027-5

At 20° C., to a solution of WX027-4 (80.00 mg, 313.39 μmol) in methanol (3.00 mL) was added sodium hydroxide solution (2 M, 313.39 μL), and the system was stirred at 20° C. for 30 mins After the reaction was complete, 10 mL water was added to dilute the reaction mixture. The system was adjusted to pH=6-7 with 1M hydrochloric acid solution, and extracted with ethyl acetate (15 mL×3). The organic phase was washed with brine (10 mL×2), dried over anhydrous sodium sulfate, filtered and concentrated to afford Compound WX027-5 (70.00 mg, 92.59% yield), white solid. $^1$H NMR (400 MHz, DMSO-d6) δ 8.65 (d, J=4.8 Hz, 1H), 7.97-7.90 (m, 1H), 7.90-7.82 (m, 1H), 7.64 (dd, J=1.3, 7.8 Hz, 1H), 7.50 (s, 1H), 7.46 (d, J=7.8 Hz, 1H), 7.35 (dd, J=5.3, 6.8 Hz, 1H), 4.81 (dd, J=6.4, 8.9 Hz, 1H), 4.71 (t, J=9.4 Hz, 1H), 4.45 (dd, J=6.7, 9.2 Hz, 1H).

Step 5: Synthesis of Compound WX027

A solution of WX027-5 (80.00 mg, 331.62 μmol), BB-1 (75.61 mg, 364.78 μmol), EDCI (95.36 mg, 497.43 μmol) and HOBt (67.21 mg, 497.43 μmol) in DMF (3.00 mL) was stirred at 40° C. for 4 hours. After the reaction was complete, at 25° C., to the system was added 10 mL water. The mixture was extracted with ethyl acetate (15 mL×3). The organic phase was separately washed with water (15 mL×3) and brine (10 mL×3), dried over anhydrous sodium sulfate, filtered and concentrated. The residue was purified with thin layer chromatography (dichloromethane:methanol=15:1) to afford Compound WX027 (61.00 mg, 42.84% yield). $^1$H NMR (400 MHz, DMSO-d6) δ 8.64 (br. s., 1H), 7.98-7.80 (m, 2H), 7.71-7.58 (m, 3H), 7.53 (s., 1H), 7.43-7.29 (m, 2H), 5.28 (br. s., 1H), 4.85 (s., 2H), 3.86 (s., 3H), 2.49-2.49 (m, 3H).

Example 6: WX131

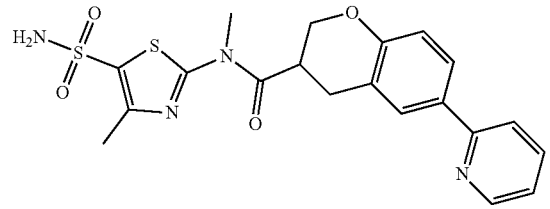 [SMILES: Cc1nc(N(C)C(=O)C2COc3ccc(-c4ccccn4)cc3C2)sc1S(N)(=O)=O]

Synthetic Route:

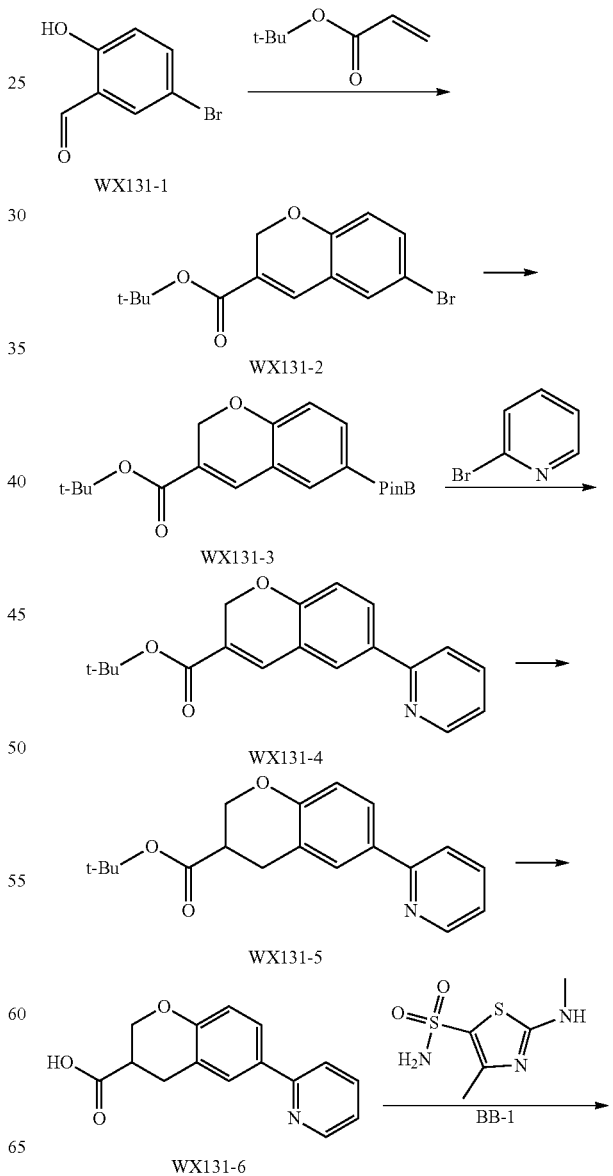

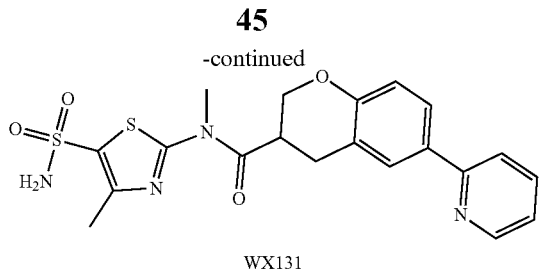

WX131

Step 1: Synthesis of Compound WX131-2

At 25° C., to a solution of WX131-1 (80.00 mg, 331.62 μmol) and tert-butyl acrylate (15.30 g, 119.40 mmol, 17.39 mL) in tert-butyl alcohol (100.00 mL) was added potassium tert-butoxide (1.67 g, 14.93 mmol, 0.3 eq.), and the system was stirred at 130° C. for 48 hours. After the reaction was complete, to the system was added 100 mL water and 100 mL ethyl acetate. The organic layer was washed with brine (100 mL), dried over anhydrous sodium sulfate, filtered and concentrated. The residue was purified by column chromatography to afford Compound WX131-2 (8.50 g, 54.91% yield), white solid. $^1$H NMR (400 MHz, DMSO-d6) δ 7.58 (d, J=2.4 Hz, 1H), 7.42-7.37 (m, 2H), 6.82 (d, J=8.7 Hz, 1H), 4.91 (d, J=1.4 Hz, 2H), 1.48 (s, 9H).

Step 2: Synthesis of Compound WX131-3

Synthesis of Compound WX131-3 was carried out by referring to the synthetic method of Example 3 Step 1, $^1$H NMR (400 MHz, DMSO-d6) δ 7.61 (s, 1H), 7.57-7.51 (m, 1H), 7.46 (s, 1H), 6.83 (d, J=8.2 Hz, 1H), 4.93 (s, 2H), 1.48 (s, 9H), 1.28 (s, 12H).

Step 3: Synthesis of Compound WX131-4

Synthesis of Compound WX131-4 was carried out by referring to the synthetic method of Example 3 Step 2, $^1$H NMR (400 MHz, CDCl$_3$) δ 8.58 (d, J=4.9 Hz, 1H), 7.81-7.73 (m, 2H), 7.69-7.63 (m, 1H), 7.61-7.56 (m, 1H), 7.36 (s, 1H), 7.19 (s, 1H), 7.13 (dd, J=4.9, 7.3 Hz, 1H), 6.86 (d, J=8.5 Hz, 1H), 4.94 (d, J=1.1 Hz, 2H), 1.47 (s, 9H).

Step 4: Synthesis of Compound WX131-5

Under a nitrogen atmosphere, to a solution of WX131-4 (820.00 mg, 2.65 mmol) in methanol (10.00 mL) was added Pd/C (10%, 0.1 g), and the system was stirred under a hydrogen atmosphere at 25° C. for 16 hours. After the reaction was complete, it was filtered, and concentrated under reduced pressure. The residue was purified by column chromatography (petroleum ether:ethyl acetate=15:1-5:1) to afford Compound WX131-5 (600.00 mg, 72.72% yield). $^1$H NMR (400 MHz, CDCl$_3$) δ 8.64-8.60 (m, 1H), 7.77 (d, J=1.1 Hz, 1H), 7.72-7.66 (m, 2H), 7.65-7.61 (m, 1H), 7.15 (ddd, J=1.3, 4.9, 7.2 Hz, 1H), 6.89 (d, J=8.6 Hz, 1H), 4.43 (dd, J=3.3, 10.8 Hz, 1H), 4.15-4.10 (m, 1H), 3.10-3.04 (m, 2H), 2.98-2.90 (m, 1H), 1.46 (s, 9H).

Step 5: Synthesis of Compound WX131-6

A solution of WX131-5 (600.00 mg, 1.93 mmol,) in formic acid (10.00 mL) was stirred at 25° C. for 12 hours. After the reaction was complete, it was concentrated under reduced pressure. The residue was purified by column chromatography (dichloromethane:methanol=30:1-10:1) to afford Compound WX131-6 (390.00 mg, 79.16% yield), white solid. $^1$H NMR (400 MHz, CDCl$_3$) δ 8.75 (br d, J=4.5 Hz, 1H), 7.83-7.78 (m, 2H), 7.68 (d, J=8.0 Hz, 1H), 7.60 (br d, J=8.4 Hz, 1H), 7.30 (s, 1H), 6.94 (d, J=8.5 Hz, 1H), 4.53 (dd, J=3.5, 11.0 Hz, 1H), 4.30-4.24 (m, 1H), 3.27-3.21 (m, 2H), 3.17-3.09 (m, 1H).

Step 6: Synthesis of Compound WX131

A solution of WX131-6 (50.00 mg, 195.87 μmol), EDCI (45.06 mg, 235.04 μmol) and HOBt (31.76 mg, 235.04 μmol) in DMF (1.00 mL) was stirred for 30 mins, and then BB-1 (48.72 mg, 235.04 μmol) was added. The system was stirred at 25° C. for 12 hours. After the reaction was complete, at 25° C., to the system was added 5 mL water. The system was extracted with ethyl acetate (20 mL×2). The organic phase was washed with brine (20 mL), dried over anhydrous sodium sulfate, filtered and concentrated. The residue was purified by column chromatography (petroleum ether:ethyl acetate=1:1) to afford Compound WX131 (50.00 mg, 57.43% yield). $^1$H NMR (400 MHz, DMSO-d6) δ 8.61 (d, J=4.4 Hz, 1H), 7.93 (s, 1H), 7.90-7.80 (m, 3H), 7.66 (s, 2H), 7.30-7.25 (m, 1H), 6.91 (d, J=8.5 Hz, 1H), 4.53 (br d, J=10.3 Hz, 1H), 4.17-4.09 (m, 1H), 3.79 (s, 3H), 3.76-3.69 (m, 1H), 3.21-3.13 (m, 1H), 3.12-3.04 (m, 1H).

Example 7: WX138

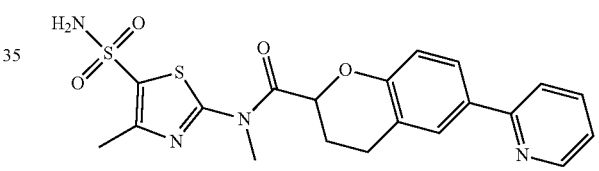

Synthetic Route:

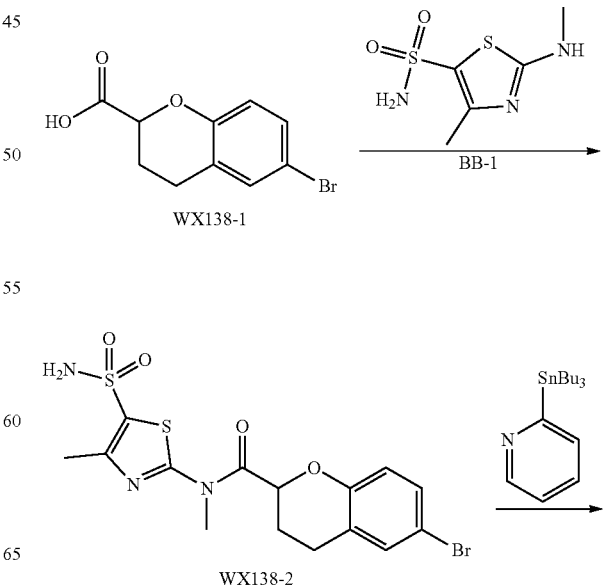

47
-continued

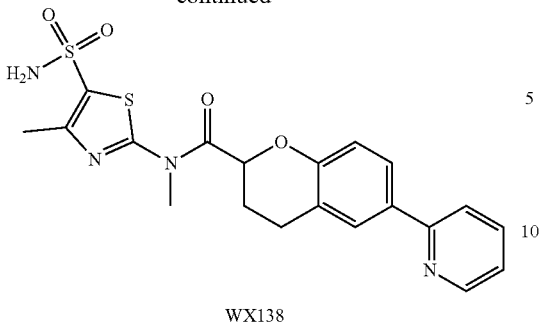
WX138

Step 1: Synthesis of Compound WX138-2

To a solution of WX138-1 (30.00 mg, 116.70 μmol) and BB-1 (29.02 mg, 140.04 μmol) in DMF (1.00 mL) were added EDCI (26.84 mg, 140.04 μmol) and HOBt (18.92 mg, 140.04μ), and the system was stirred at 50° C. for 8 hours. After the reaction was complete, it was concentrated under reduced pressure. To the system was added 10 mL water. The system was extracted with dichloromethane (10 mL×2). The organic phase was concentrated under reduced pressure to afford Compound WX138-2 (40.00 mg, crude product), white solid. $^1$H NMR (400 MHz, DMSO-d6) δ 7.69 (s, 2H), 7.30 (s, 1H), 7.26 (br d, J=8.7 Hz, 1H), 6.82 (d, J=8.5 Hz, 1H), 5.52 (dd, J=3.6, 6.8 Hz, 1H), 3.72 (s, 3H), 2.91-2.80 (m, 1H), 2.75-2.65 (m, 1H), 2.20 (br d, J=3.9 Hz, 1H), 2.15-2.04 (m, 1H).

Step 2: Synthesis of Compound WX138

Synthesis of Compound WX138 was carried out by referring to the synthetic method of Example 5 Step 3, $^1$H NMR (400 MHz, DMSO-d6) δ 8.61 (d, J=4.0 Hz, 1H), 7.91-7.80 (m, 4H), 7.69 (s, 2H), 7.29 (s, 1H), 6.96 (d, J=8.3 Hz, 1H), 5.58 (dd, J=3.5, 7.3 Hz, 1H), 3.77 (s, 3H), 2.95 (br d, J=8.3 Hz, 1H), 2.86-2.76 (m, 1H), 2.31-2.25 (m, 1H), 2.22-2.11 (m, 1H).

Example 8: WX141

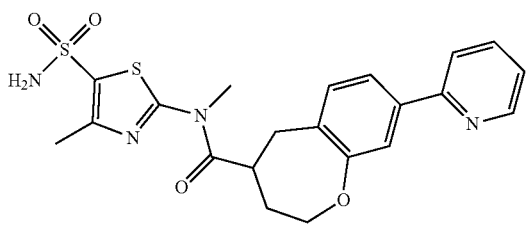 [SMILES: Cc1nc(N(C)C(=O)C2CCOc3cc(-c4ccccn4)ccc3C2)sc1S(N)(=O)=O]

Synthetic Route:

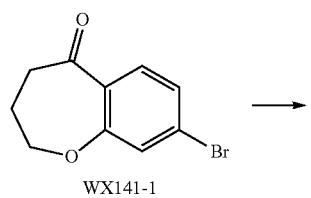
WX141-1

48
-continued

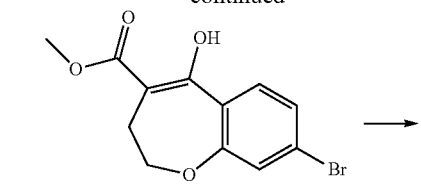
WX141-2

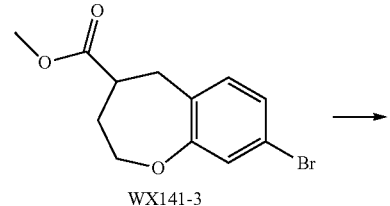
WX141-3

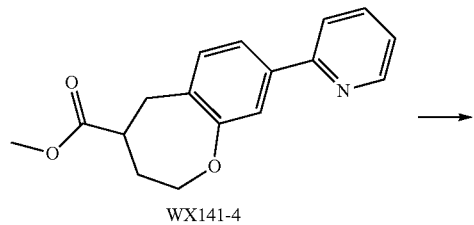
WX141-4

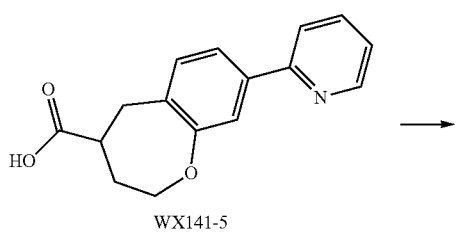
WX141-5

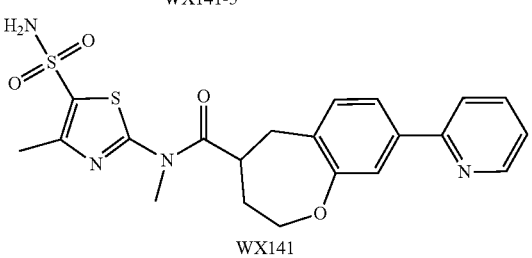
WX141

Step 1: Synthesis of Compound WX141-2

At 0° C., to a solution of sodium hydride (1.49 g, 37.32 mmol, 60% purity) in tetrahydrofuran (20.00 mL) was added a solution of WX141-1 (3.00 g, 12.44 mmol) in tetrahydrofuran (20.00 mL) dropwise. The mixture was stirred for 10 mins and stirred at room temperature for 10 mins, and then dimethyl carbonate (6.72 g, 74.64 mmol, 6.28 mL) was added dropwise. The system was stirred at room temperature for 1 hour, and at 40° C. for 1 hour. After the reaction was complete, to the system was added 100 mL 1M hydrochloric acid dropwise. The system was extracted with ethyl acetate (100 mL×3), dried over anhydrous sodium sulfate, filtered and concentrated. The residue was purified by column chromatography to afford Compound WX141-2 (2.25 g, crude product), light yellow solid. $^1$H NMR (400 MHz, CDCl$_3$) δ 13.13 (s, 1H), 7.84 (d, J=8.5 Hz, 1H), 7.28-7.25 (m, 1H), 7.22 (d, J=2.0 Hz, 1H), 4.39 (t, J=5.3 Hz, 2H), 3.86 (s, 3H), 2.72 (t, J=5.3 Hz, 2H).

Step 2: Synthesis of Compound WX141-3

To a solution of WX141-2 (75.00 mg, 250.74 μmol) in trifluoroacetic acid (5.00 mL) was added triethyl silane (174.93 mg, 1.50 mmol, 239.63 μL), and the system was reacted at room temperature for 18 hours. It was concentrated under reduced pressure. The residue was purified by column chromatography to afford WX141-3 (200.00 mg, crude product), light yellow oil. $^1$H NMR (400 MHz, DMSO-d6) δ 7.18 (s, 2H), 7.13 (s, 1H), 4.26-4.17 (m, 1H), 3.84 (ddd, J=2.8, 8.7, 12.1 Hz, 1H), 3.61 (s, 3H), 3.02-2.84 (m, 2H), 2.77-2.65 (m, 1H), 2.16-1.98 (m, 2H).

Step 3: Synthesis of Compound WX141-4

Synthesis of Compound WX141-4 was carried out by referring to the synthetic method of Example 5 Step 3, $^1$H NMR (400 MHz, DMSO-d6) δ 8.64 (d, J=4.3 Hz, 1H), 7.97-7.90 (m, 1H), 7.88-7.82 (m, 1H), 7.72 (d, J=7.8 Hz, 1H), 7.65 (s, 1H), 7.36-7.29 (m, 2H), 4.31-4.20 (m, 1H), 3.89-3.81 (m, 1H), 3.63 (s, 3H), 3.07-2.96 (m, 2H), 2.75 (td, J=4.2, 8.8 Hz, 1H), 2.11 (br dd, J=8.0, 11.0 Hz, 2H).

Step 4: Synthesis of Compound WX141-5

To a solution of WX141-4 (80.00 mg, 282.37 μmol) in tetrahydrofuran (1.50 mL), water (150.00 μL) and methanol (300.00 μL) was added lithium hydroxide (13.53 mg, 564.74 μmol), and the system was stirred at room temperature for 3 hours. After the reaction was complete, the system was adjusted to neutral with 1M hydrochloric acid, extracted with ethyl acetate (10 mL×3), dried over anhydrous sodium sulfate, filtered and concentrated to afford Compound WX141-5 (70.00 mg, 92.06% yield), light yellow oil. $^1$H NMR (400 MHz, DMSO-d6) δ 8.63 (d, J=4.3 Hz, 1H), 7.93 (d, J=7.8 Hz, 1H), 7.88-7.82 (m, 1H), 7.71 (d, J=8.0 Hz, 1H), 7.64 (s, 1H), 7.35-7.30 (m, 2H), 4.30-4.22 (m, 1H), 3.89-3.79 (m, 1H), 3.08-2.95 (m, 2H), 2.65-2.57 (m, 1H), 2.17-2.05 (m, 2H).

Step 5: Synthesis of Compound WX141

Synthesis of Compound WX141 was carried out by referring to the synthetic method of Example 7 Step 1, $^1$H NMR (400 MHz, DMSO-d6) δ 8.77 (d, J=5.3 Hz, 1H), 8.29-8.16 (m, 2H), 7.79-7.63 (m, 5H), 7.48 (d, J=7.8 Hz, 1H), 4.55-4.44 (m, 1H), 3.87 (br s, 1H), 3.78-3.77 (m, 3H), 3.33 (br s, 1H), 3.14-3.00 (m, 2H), 2.53 (br s, 3H), 2.22-2.06 (m, 2H).

Example 9: WX043

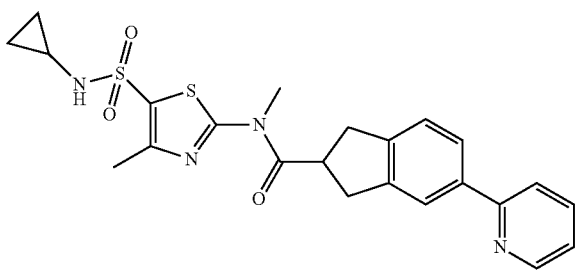 [SMILES: Cc1nc(N(C)C(=O)C2Cc3ccc(-c4ccccn4)cc3C2)sc1S(=O)(=O)NC1CC1]

Synthetic Route:

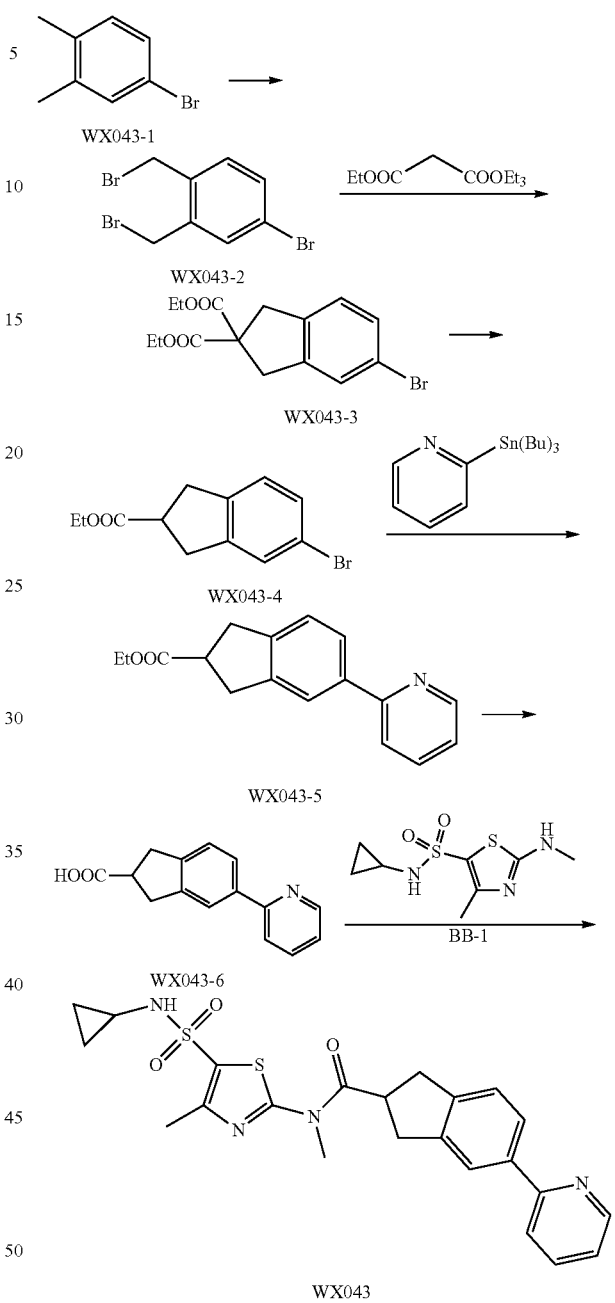

Step 1: Synthesis of Compound WX043-2

To a solution of WX043-1 (30.00 g, 162.11 mmol) in carbon tetrachloride (400.00 m) was added NBS (57.70 g, 324.22 mmol) and AIBN (5.32 g, 32.42 mmol), and the system was stirred at 80° C. for 2 hours. After the reaction was complete, it was concentrated under reduced pressure. The residue was purified by column chromatography to afford Compound WX043-2 (37.00 g, crude product), colorless oil. $^1$H NMR (400 MHz, CDCl$_3$) δ 7.55 (s, 1H), 7.47-7.45 (m, 1H), 7.28-7.25 (m, 1H), 4.62 (s, 2H), 4.60 (s, 2H).

Step 2: Synthesis of Compound WX043-3

Sodium hydride was slowly added to ethanol (144.00 mL) and tetrahydrofuran (432.00 mL), stirred at room temperature for 5 mins, and then to the system was added diethyl malonate (18.22 g, 113.75 mmol) and WX043-2 (39.00 g, 113.75 mmol), and the system was stirred at room temperature for 30 mins After the reaction was complete, water was added to quench the reaction. After concentration under reduced pressure, the residue was purified by column chromatography to afford Compound WX043-3 (21.00 g, crude product), colorless oil.

Step 3: Synthesis of Compound WX043-4

To a solution of WX043-3 (10.00 g, 29.31 mmol) in water (10.00 mL) and DMSO (100.00 mL) was added lithium chloride (7.45 g, 175.86 mmol), and the system was stirred at 160° C. for 4 hours. After the reaction was complete, 100 mL water was added. The system was extracted with ethyl acetate (50 mL×5). The organic layer was washed with aqueous sodium bicarbonate solution (50 mL×2), dried over anhydrous sodium sulfate, and filtered, and the filtrate was concentrated under reduced pressure. The residue was purified by column chromatography (petroleum ether:ethyl acetate=10:1) to afford Compound WX043-4 (3.5 g, crude product), yellow oil. $^1$H NMR (400 MHz, DMSO-d6) δ 7.40 (s, 1H), 7.29 (d, J=8.0 Hz, 1H), 7.15 (d, J=8.0 Hz, 1H), 4.07 (t, J=14.0 Hz, 2H), 3.42-3.35 (m, 1H), 3.16-3.04 (m, 4H), 1.18 (t, J=15.6 Hz, 3H).

Step 4: Synthesis of Compound WX043-5

Synthesis of Compound WX043-5 was carried out by referring to the synthetic method of Example 5 Step 3, $^1$H NMR (400 MHz, DMSO-d6) δ 8.62 (d, J=6.4 Hz, 1H), 7.92-7.81 (m, 4H), 7.29 (d, J=5.2 Hz, 2H), 4.09 (q, J1=18.0 Hz, J2=6.8 Hz, 2H), 3.40-3.23 (m, 1H), 3.21-3.15 (m, 4H), 1.20 (t, J=14.4 Hz, 3H).

Step 5: Synthesis of Compound WX043-6

Synthesis of Compound WX043-6 was carried out by referring to the synthetic method of Example 5 Step 4, $^1$H NMR (400 MHz, DMSO-d6) δ 8.63 (d, J=4.4 Hz, 1H), 7.94-7.83 (m, 4H), 7.34-7.31 (m, 2H), 3.310-3.00 (m, 1H), 3.22-3.16 (m, 4H).

Step 6: Synthesis of Compound WX043

Synthesis of Compound WX043 was carried out by referring to the synthetic method of Example 7 Step 1, $^1$H NMR (400 MHz, DMSO-d6) δ 8.65 (d, J=3.6 Hz, 1H), 7.95-7.84 (m, 4H), 7.36-7.32 (m, 2H), 4.12-4.06 (m, 1H), 3.78 (s, 3H), 3.44-3.39 (m, 2H), 3.30-3.27 (m, 2H), 3.25 (s, 3H), 2.24-2.19 (m, 1H), 0.55-0.52 (m, 2H), 0.44-0.43 (m, 2H).

Example 10: WX072

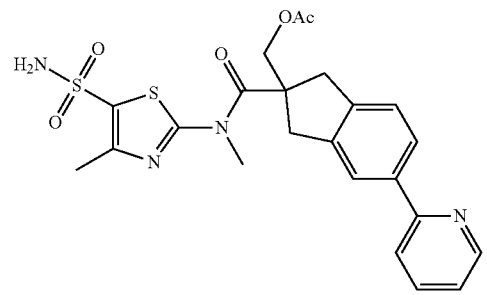 [SMILES: CC(=O)OCC1(C(=O)N(C)c2nc(C)c(S(N)(=O)=O)s2)Cc2ccc(-c3ccccn3)cc2C1]

Synthetic Route:

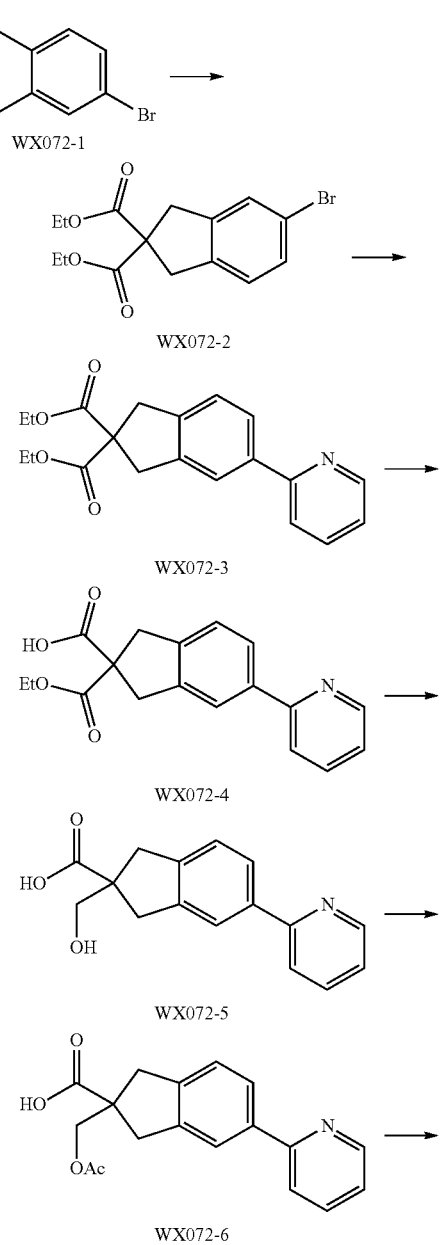

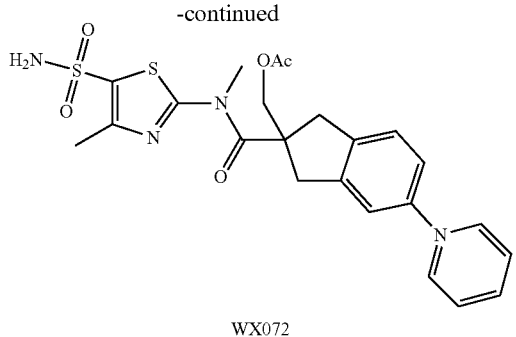

WX072

Step 1: Synthesis of Compound WX072-2

To a solution of ethanol (10.00 mL) and tetrahydrofuran (30.00 mL) was slowly added sodium hydride (4.92 g, 123.08 mmol) (60%), and stirred at 15° C. for 5 mins, and then to the system was added diethyl malonate (9.34 g, 58.33 mmol) and WX072-1 (20.00 g, 58.33 mmol) in tetrahydrofuran (30.00 mL), and the system was stirred at 15° C. for 55 mins. After the reaction was complete, 100 mL ammonium chloride solution was added to quench the reaction. The system was extracted with ethyl acetate (500 mL×3). The organic layer was washed with brine (300 mL), dried over anhydrous sodium sulfate, and filtered, and the filtrate was concentrated under reduced pressure. The residue was purified by column chromatography to afford Compound WX072-2 (12.00 g, 60.29% yield), yellow oil. $^1$H NMR (400 MHz, CDCl$_3$) 7.40-7.31 (m, 2H), 7.14-7.02 (m, 1H), 4.27-4.20 (m, 4H), 3.72-3.27 (m, 4H), 1.37-1.22 (m, 6H).

Step 2: Synthesis of Compound WX072-3

Synthesis of Compound WX072-3 was carried out by referring to the synthetic method of Example 5 Step 3.

Step 3: Synthesis of Compound WX072-4

Synthesis of Compound WX072-4 was carried out by referring to the synthetic method of Example 5 Step 4, $^1$H NMR (400 MHz, DMSO-d6) δ 8.58-8.70 (m, 1H), 7.69-7.95 (m, 4H), 7.07-7.42 (m, 2H), 3.96-4.07 (m, 2H), 3.35-3.54 (m, 4H), 1.16 (t, J=7.03 Hz, 3H).

Step 4: Synthesis of Compound WX072-5

At 15° C., to a solution of WX072-4 (2.50 g, 8.03 mmol) in tetrahydrofuran (30.00 m) and 2-propanol (30.00 mL) was added lithium borohydride (349.79 mg, 16.06 mmol), and the system was stirred at 15° C. for 16 hours. After the reaction was complete, the system was adjusted to pH=4 with 1M hydrochloric acid, and then adjusted to neutral with potassium carbonate solution, and concentrated under reduced pressure. The residue was dissolved in dichloromethane:methanol=10:1 (1 L). The precipitate was filtered off, and the filtrate was concentrated to afford Compound WX072-5 (2.00 g, 92.49% yield), yellow solid. $^1$H NMR (400 MHz, METHANOL-d$_4$) δ 8.78 (d, J=5.52 Hz, 1H), 8.59-8.51 (m, 1H), 8.30 (d, J=8.03 Hz, 1H), 7.92 (t, J=6.78 Hz, 1H), 7.85-7.80 (m, 1H), 7.77 (d, J=8.03 Hz, 1H), 7.55-7.46 (m, 1H), 3.81-3.74 (m, 2H), 3.56-3.47 (m, 2H), 3.18 (dd, J=16.81, 7.78 Hz, 2H).

Step 5: Synthesis of Compound WX072-6

At 0° C., to a solution of WX072-5 (2.00 g, 7.43 mmol) in pyridine (30.00 m) was added acetyl chloride (2.65 mL, 37.13 mmol), and the system was stirred at 15° C. for 16 hours. After the reaction was complete, the system was adjusted to pH=6 with 1M hydrochloric acid. The reaction mixture was extracted with dichloromethane (500 mL×3). The organic phases were combined, and washed separately with 300 mL brine and 300 mL water, dried over anhydrous sodium sulfate, filtered and concentrated to afford Compound WX072-6 (2.30 g, crude product), brown oil.

Step 6: Synthesis of Compound WX072

Synthesis of Compound WX072 was carried out by referring to the synthetic method of Example 7 Step 1, $^1$H NMR (400 MHz, DMSO-d6) δ 8.63 (d, J=4.27 Hz, 1H), 7.82-7.99 (m, 4H), 7.65 (br. s., 2H), 7.29-7.39 (m, 2H), 4.30 (s, 2H), 3.63-3.71 (m, 5H), 3.36 (br. s., 2H), 2.43-2.47 (m, 3H), 1.94 (s, 3H).

Example 11: WX073

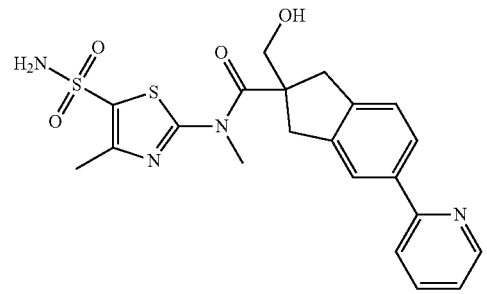 [SMILES: Cc1nc(N(C)C(=O)C2(CO)Cc3ccc(-c4ccccn4)cc3C2)sc1S(N)(=O)=O]

Synthetic Route:

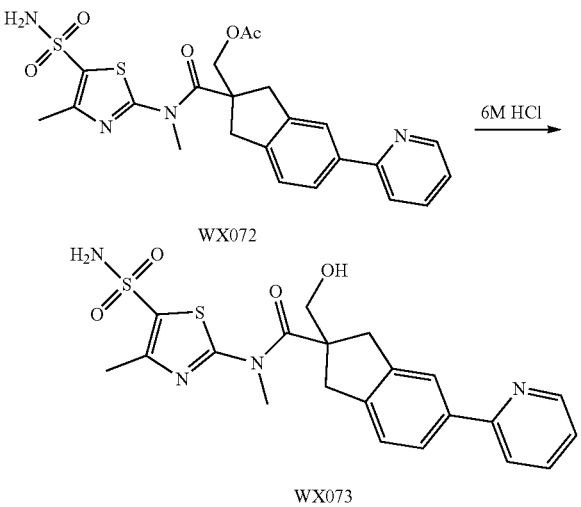

Step 1: Synthesis of Compound WX073

A solution of WX072 (50.00 mg, 99.88 μmol) in hydrochloric acid (6 M, 3.00 mL) was stirred at 15° C. for 1 hour.

After the reaction was complete, the system was adjusted to pH=7 with sodium bicarbonate solution. The reaction mixture was extracted with dichloromethane (100 mL×3). The organic phases were combined, dried over anhydrous sodium sulfate, filtered and concentrated. The residue was purified by preparative chromatography to afford Compound WX073 (6.00 mg, 13.10% yield). $^1$H NMR (400 MHz, DMSO-d6) δ 8.65 (d, J=4.02 Hz, 1H), 7.83-8.00 (m, 4H), 7.65 (br. s., 2H), 7.30-7.40 (m, 2H), 5.31-5.41 (m, 1H), 3.76 (s, 3H), 3.67 (d, J=5.02 Hz, 2H), 3.58-3.65 (m, 2H), 3.27 (br. s., 2H), 2.54-2.58 (m, 3H).

Example 12: WX074

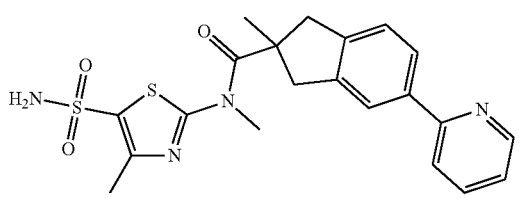 [SMILES: Cc1nc(N(C)C(=O)C2(C)Cc3ccc(-c4ccccn4)cc3C2)sc1S(N)(=O)=O]

Synthetic Route:

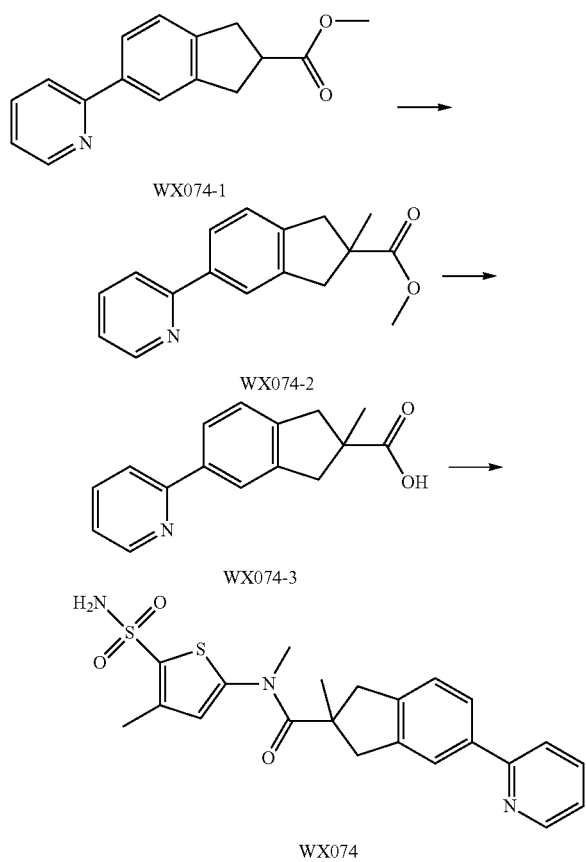

Step 1: Synthesis of Compound WX074-2

Under a nitrogen atmosphere, at −78° C., to a solution of WX074-1 (1.00 g, 3.95 mmol) in tetrahydrofuran (10.00 mL) was added LDA (2 M, 2.96 mL) dropwise, and stirred at −78° C. for 1 hour, then to the system was added methyl iodide (2.80 g, 19.74 mmol), and stirred at this temperature for 2 hours. After the reaction was complete, 10 mL water was added at 0° C. to quench the reaction. The reaction mixture was extracted with ethyl acetate (15 mL×3). The organic phase was washed with 15 mL brine, dried over anhydrous sodium sulfate, filtered and concentrated. The residue was purified by column chromatography to afford Compound WX074-2 (600.00 mg, 56.82% yield), white solid. $^1$H NMR (400 MHz, CDCl$_3$) δ 8.67 (m, 1H), 7.85 (s, 1H), 7.77-7.69 (m, 3H), 7.29 (d, J=7.8 Hz, 1H), 7.21 (m, 1H), 3.73 (s, 3H), 3.53 (dd, J=3.0, 16.1 Hz, 2H), 2.88 (t, J=15.4 Hz, 2H), 1.39 (s, 3H).

Step 2: Synthesis of Compound WX074-3

Synthesis of Compound WX074-3 was carried out by referring to the synthetic method of Example 5 Step 4, $^1$H NMR (400 MHz, CDCl$_3$) δ 8.70 (d, J=4.02 Hz, 1H), 7.83 (s, 1H), 7.67-7.78 (m, 3H), 7.29 (d, J=7.78 Hz, 1H), 7.19-7.25 (m, 1H), 3.49-3.61 (m, 2H), 2.81-2.96 (m, 2H), 1.36-1.46 (m, 3H).

Step 3: Synthesis of Compound WX074

Synthesis of Compound WX074 was carried out by referring to the synthetic method of Example 7 Step 1, $^1$H NMR (400 MHz, DMSO-d6) δ 8.61-8.67 (m, 1H), 7.98 (s, 1H), 7.92 (br. s., 2H), 7.83-7.89 (m, 1H), 7.65 (s, 2H), 7.35-7.40 (m, 1H), 7.29-7.35 (m, 1H), 3.71 (s, 5H), 3.06-3.17 (m, 2H), 2.48-2.49 (m, 3H), 1.44 (s, 3H).

Example 13: WX129

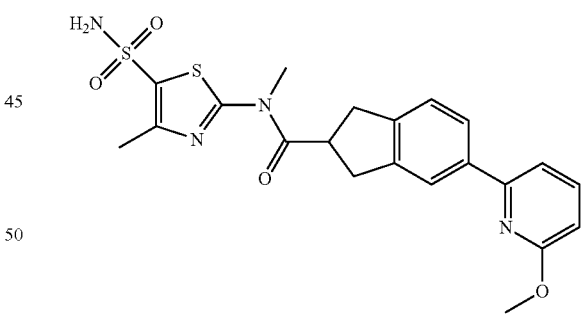

Synthetic Route:

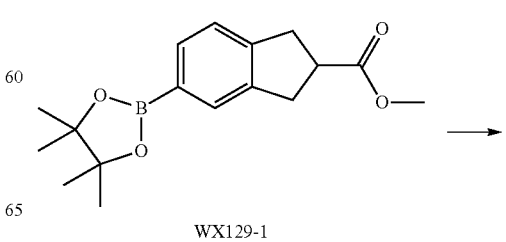

Example 14: WX156

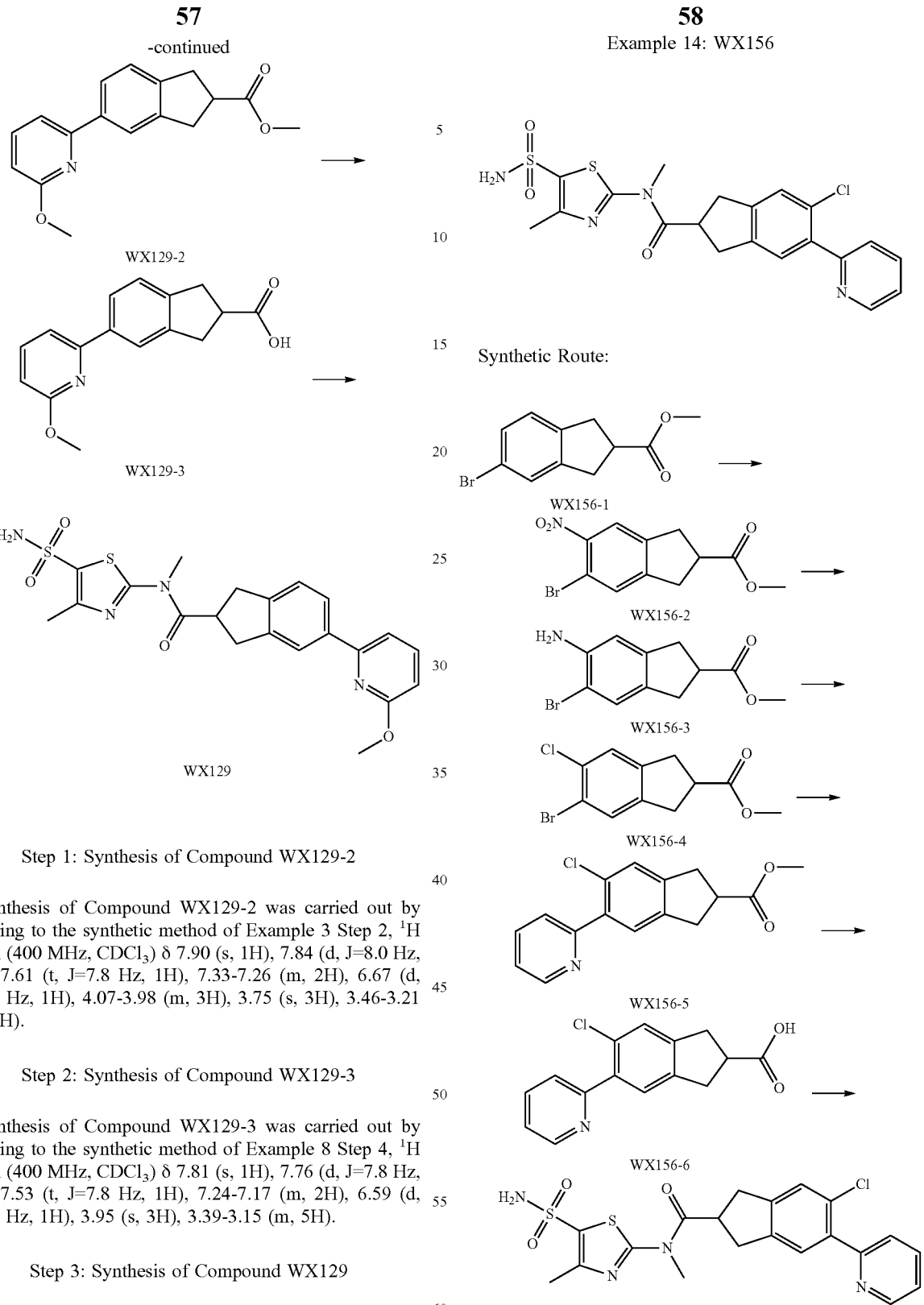

Step 1: Synthesis of Compound WX129-2

Synthesis of Compound WX129-2 was carried out by referring to the synthetic method of Example 3 Step 2, $^1$H NMR (400 MHz, CDCl$_3$) δ 7.90 (s, 1H), 7.84 (d, J=8.0 Hz, 1H), 7.61 (t, J=7.8 Hz, 1H), 7.33-7.26 (m, 2H), 6.67 (d, J=8.3 Hz, 1H), 4.07-3.98 (m, 3H), 3.75 (s, 3H), 3.46-3.21 (m, 5H).

Step 2: Synthesis of Compound WX129-3

Synthesis of Compound WX129-3 was carried out by referring to the synthetic method of Example 8 Step 4, $^1$H NMR (400 MHz, CDCl$_3$) δ 7.81 (s, 1H), 7.76 (d, J=7.8 Hz, 1H), 7.53 (t, J=7.8 Hz, 1H), 7.24-7.17 (m, 2H), 6.59 (d, J=8.0 Hz, 1H), 3.95 (s, 3H), 3.39-3.15 (m, 5H).

Step 3: Synthesis of Compound WX129

Synthesis of Compound WX129 was carried out by referring to the synthetic method of Example 7 Step 1, $^1$H NMR (400 MHz, DMSO-d6) δ 7.98 (s, 1H), 7.92 (d, J=7.8 Hz, 1H), 7.77 (t, J=7.9 Hz, 1H), 7.64 (s, 2H), 7.53 (d, J=7.5 Hz, 1H), 7.35 (d, J=8.0 Hz, 1H), 6.76 (d, J=8.3 Hz, 1H), 4.16-4.04 (m, 1H), 3.96 (s, 3H), 3.77 (s, 3H), 3.40-3.22 (m, 4H).

Step 1: Synthesis of Compound WX156-2

At 0° C., to a solution of WX156-1 (5.00 g, 19.60 mmol) in sulphuric acid (40.00 mL) was added nitric acid (2.09 g, 21.56 mmol, 1.49 mL) and sulphuric acid (3.69 g, 36.85 mmol, 2.00 mL, 98% purity) slowly during 5 mins, stirred at −78° C. for 1 hour, and then to the system was added methyl iodide (2.80 g, 19.74 mmol), stirred at this temperature for 25 mins After the reaction was complete, the reaction mixture was poured into 300 mL ice water. The reaction mixture was extracted with ethyl acetate (300 mL×3). The organic phase was washed separately with 250 mL aqueous sodium bicarbonate solution and 250 mL brine, dried over anhydrous sodium sulfate, filtered and concentrated to afford Compound WX156-2 (5.25 g, crude product). $^1$H NMR (400 MHz, CDCl$_3$) δ 7.62 (s, 1H), 7.48 (s, 1H), 3.63 (br s, 3H), 3.40-3.18 (m, 5H).

Step 2: Synthesis of Compound WX156-3

To a solution of WX156-2 (5.20 g, 17.33 mmol) and iron (4.84 g, 86.65 mmol) in tetrahydrofuran (32.00 mL) was added methanol (8.00 mL) and water (8.00 mL), and then ammonium chloride (2.32 g, 43.33 mmol). After the reaction was complete, 200 mL water was added. The mixture was extracted with ethyl acetate (200 mL×3). The organic phases were combined, and washed with brine (200 mL). The organic phase was dried over anhydrous sodium sulfate, filtered and concentrated. The residue was purified by column chromatography to afford Compound WX156-3 (3.15 g, 67.29% yield), colorless liquid. $^1$H NMR (400 MHz, CDCl$_3$) δ 7.62 (s, 1H), 7.48 (s, 1H), 3.63 (br s, 3H), 3.40-3.18 (m, 5H).

Step 3: Synthesis of Compound WX156-4

A solution of WX156-3 (5.20 g, 17.33 mmol), tert-butyl nitrite (274.86 mg, 2.67 mmol, 315.94 μL) and ferric chloride (358.37 mg, 2.67 mmol) in acetonitrile (5.00 mL) was heated from 15° C. to 60° C., and stirred at this temperature for 1 hour. 60 mL water was added, and the mixture was extracted with ethyl acetate (60 mL×3). The organic phase was dried over anhydrous sodium sulfate, filtered and concentrated. The residue was purified by column chromatography to afford Compound WX156-4 ((245.00 mg, 63.62% yield), white solid. $^1$H NMR (400 MHz, CDCl$_3$) δ 7.45 (s, 1H), 7.29 (s, 1H), 3.73 (s, 3H), 3.41-3.31 (m, 1H), 3.25-3.13 (m, 4H).

Step 4: Synthesis of Compound WX156-5

Synthesis of Compound WX156-5 was carried out by referring to the synthetic method of Example 5 Step 3.

Step 5: Synthesis of Compound WX156-6

Synthesis of Compound WX156-6 was carried out by referring to the synthetic method of Example 8 Step 4, $^1$H NMR (400 MHz, CDCl$_3$) δ 8.64 (br d, J=3.8 Hz, 1H), 7.69 (br d, J=7.3 Hz, 1H), 7.58 (br d, J=7.5 Hz, 1H), 7.36 (br s, 1H), 7.24 (br d, J=5.5 Hz, 2H), 1.53 (s, 1H), 1.28-1.20 (m, 4H).

Step 6: Synthesis of Compound WX156

Synthesis of Compound WX156 was carried out by referring to the synthetic method of Example 7 Step 1, $^1$H NMR (400 MHz, DMSO-d6) δ 8.79 (br d, J=4.8 Hz, 1H), 8.19 (br s, 1H), 7.84 (br d, J=7.5 Hz, 1H), 7.65 (br s, 3H), 7.49 (d, J=9.5 Hz, 2H), 4.18-4.06 (m, 1H), 3.73 (s, 3H), 3.44-3.20 (m, 4H), 2.47 (br s, 3H).

Example 15: WX130

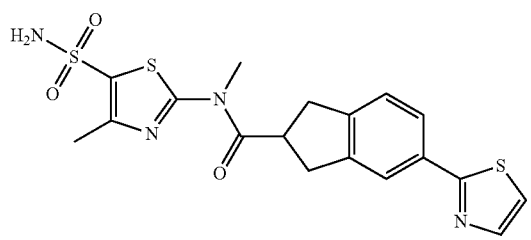 [SMILES: Cc1nc(N(C)C(=O)C2Cc3ccc(-c4nccs4)cc3C2)sc1S(N)(=O)=O]

Synthetic Route:

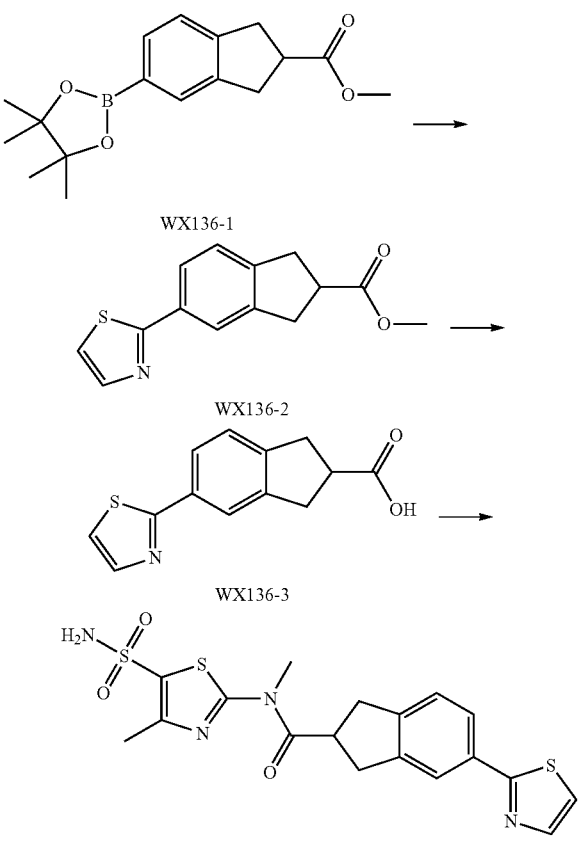

Step 1: Synthesis of Compound WX136-2

Synthesis of Compound WX136-2 was carried out by referring to the synthetic method of Example 3 Step 2, $^1$H NMR (400 MHz, CDCl$_3$) δ 7.78-7.74 (m, 2H), 7.70 (d, J=8.0 Hz, 1H), 7.23 (d, J=3.3 Hz, 1H), 7.19 (s, 1H), 3.67 (s, 3H), 3.37-3.13 (m, 5H).

Step 2: Synthesis of Compound WX136-3

Synthesis of Compound WX136-3 was carried out by referring to the synthetic method of Example 8 Step 4, $^1$H NMR (400 MHz, CDCl₃) δ 7.78 (d, J=3.3 Hz, 1H), 7.75 (s, 1H), 7.69 (d, J=8.3 Hz, 1H), 7.25-7.18 (m, 2H), 3.41-3.17 (m, 5H).

Step 3: Synthesis of Compound WX136

Synthesis of Compound WX136 was carried out by referring to the synthetic method of Example 7 Step 1, ¹H NMR (400 MHz, DMSO-d6) δ 7.90 (d, J=3.3 Hz, 1H), 7.82 (s, 1H), 7.80-7.73 (m, 2H), 7.65 (br s, 2H), 7.37 (d, J=7.8 Hz, 1H), 4.10 (quin, J=7.8 Hz, 1H), 3.75 (s, 3H), 3.45-3.22 (m, 4H), 2.49 (br s, 3H).

Example 16: WX142

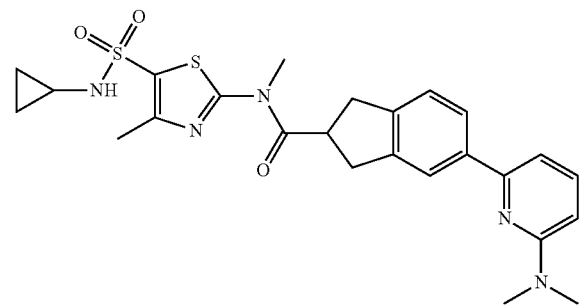 [SMILES: Cc1nc(N(C)C(=O)C2Cc3ccc(-c4cccc(N(C)C)n4)cc3C2)sc1S(=O)(=O)NC1CC1]

Synthetic Route:

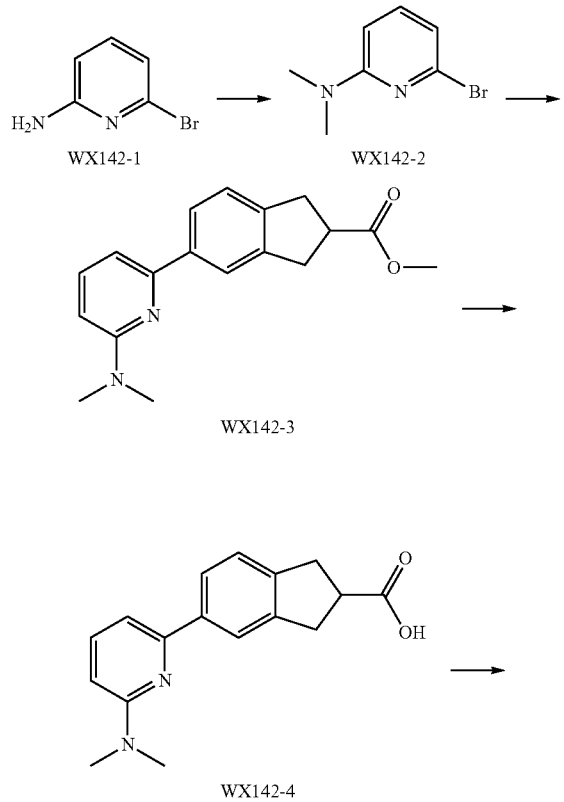

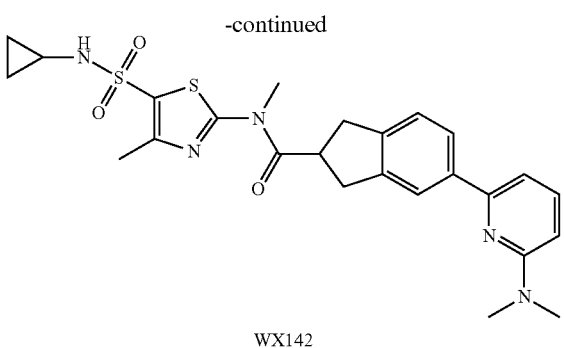

WX142

Step 1: Synthesis of Compound WX142-2

At 0° C., to a solution of WX142-1 (1.00 g, 5.78 mmol) in acetonitrile (30.00 mL) was added paraformaldehyde (3.47 g, 115.60 mmol, 3.18 mL) and sodium cyanoborohydride (1.09 g, 17.34 mmol). The system was stirred at this temperature for 10 mins, and then acetic acid (2.08 g, 34.68 mmol, 1.98 mL) was added dropwise. After the reaction was complete, it was filtered. To the filtrate was added 150 mL water, and the mixture was extracted with ethyl acetate (150 mL×3). The organic phase was dried over anhydrous sodium sulfate, filtered and concentrated. The residue was purified by column chromatography to afford Compound WX142-2 (1.02 g, 5.07 mmol, 87.77% yield), colorless liquid. ¹H NMR (400 MHz, CDCl₃) 7.17 (dd, J=7.5, 8.3 Hz, 1H), 6.59 (d, J=7.3 Hz, 1H), 6.30 (d, J=8.3 Hz, 1H), 2.99 (s, 6H).

Step 2: Synthesis of Compound WX142-3

Synthesis of Compound WX142-3 was carried out by referring to the synthetic method of Example 3 Step 2, ¹H NMR (400 MHz, CDCl₃) δ 7.81 (s, 1H), 7.76 (d, J=7.8 Hz, 1H), 7.42 (dd, J=7.5, 8.3 Hz, 1H), 7.21-7.16 (m, 1H), 6.92 (d, J=7.5 Hz, 1H), 6.39 (d, J=8.3 Hz, 1H), 3.67 (s, 3H), 3.35-3.13 (m, 5H), 3.09-3.08 (m, 1H), 3.08 (s, 7H).

Step 3: Synthesis of Compound WX142-4

Synthesis of Compound WX142-4 was carried out by referring to the synthetic method of Example 8 Step 4, ¹H NMR (400 MHz, CDCl₃) δ 7.81 (s, 1H), 7.76 (d, J=7.8 Hz, 1H), 7.42 (dd, J=7.5, 8.3 Hz, 1H), 7.19-7.17 (m, 1H), 6.91 (d, J=7.5 Hz, 1H), 6.38 (d, J=8.3 Hz, 1H), 3.39-3.15 (m, 5H), 3.08 (s, 6H).

Step 4: Synthesis of Compound WX142

Synthesis of Compound WX142 was carried out by referring to the synthetic method of Example 7 Step 1, ¹H NMR (400 MHz, DMSO-d6) δ 8.15 (br s, 1H), 7.88-7.74 (m, 2H), 7.71 (br d, J=7.5 Hz, 1H), 7.38 (d, J=7.8 Hz, 1H), 7.10 (d, J=7.3 Hz, 1H), 6.94 (br s, 1H), 4.17-4.01 (m, 1H), 3.76 (s, 3H), 3.45-3.24 (m, 4H), 3.20 (s, 6H), 2.48 (br s, 3H), 2.18 (br s, 1H), 0.55-0.34 (m, 4H).

Example 17: WX133

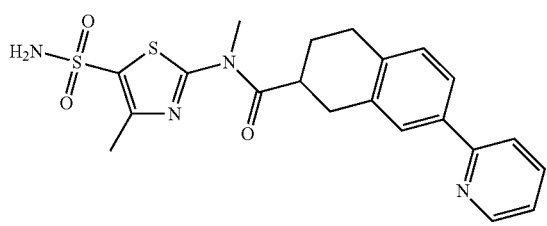 [SMILES: Cc1nc(N(C)C(=O)C2CCc3ccc(-c4ccccn4)cc3C2)sc1S(N)(=O)=O]

Synthetic Route:

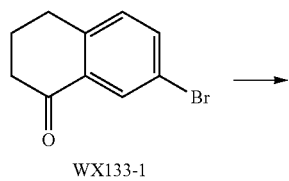

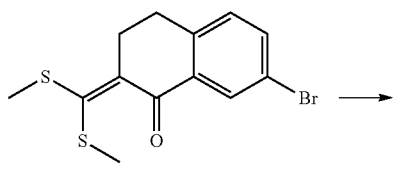

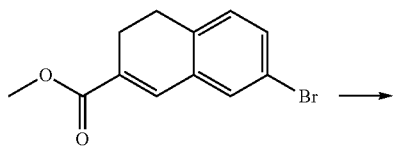

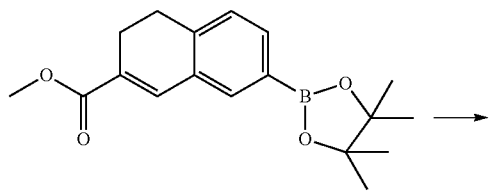

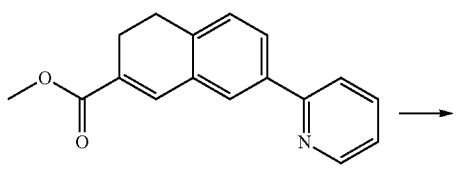

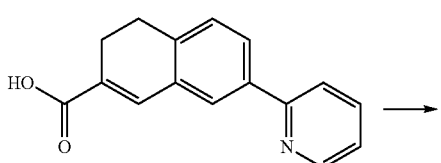

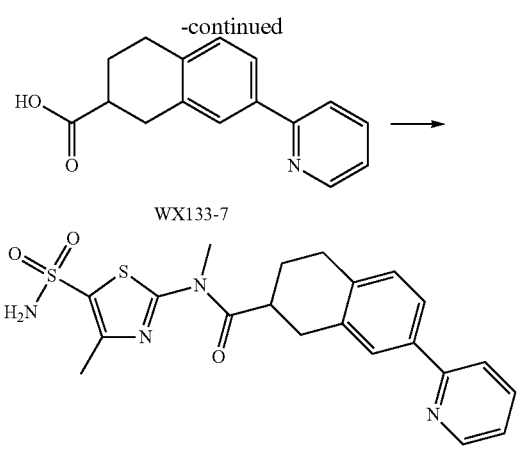

Step 1: Synthesis of Compound WX133-2

At 0° C., to a solution of potassium tert-butoxide (5.98 g, 53.30 mmol) in DMF (13.00 mL) and toluene (37.00 mL) was added a solution of WX133-1 (5.00 g, 22.21 mmol) and carbon disulfide (1.69 g, 22.21 mmol, 1.34 mL) in toluene (10.00 mL) dropwise. The system was stirred at room temperature for 4 hours, and then methyl iodide (6.62 g, 46.64 mmol, 2.90 mL) was added, and the reaction mixture was stirred at room temperature for 18 hours. After the reaction was complete, 100 mL water was added. The mixture was extracted with methyl tert-butyl ether (100 mL×3). The organic phases were combined, and washed with brine (25 mL×2). The organic phase was dried over anhydrous sodium sulfate, filtered and concentrated to afford Compound WX133-2 (4.40 g, 60.15% yield), yellow solid.

Step 2: Synthesis of Compound WX133-3

To a solution of WX133-2 (4.40 g, 13.36 mmol) in methanol (50.00 mL) was added sodium borohydride (1.01 g, 26.72 mmol) and $BF_3 \cdot Et_2O$ (34.13 g, 240.48 mmol, 29.68 mL), and the system was stirred at 25-50° C. for 16 hours. After the reaction was complete, 50 mL water was added. The mixture was extracted with ethyl acetate (100 mL×2). The organic phases were combined, and washed with brine (100 mL). The organic phase was dried over anhydrous sodium sulfate, filtered and concentrated. The residue was purified by column chromatography (petroleum ether:ethyl acetate=1:0-2:1) to afford Compound WX133-3 (3.10 g, 86.87% yield), white solid. $^1$H NMR (400 MHz, DMSO-d6) δ 7.61 (d, J=2.0 Hz, 1H), 7.51 (s, 1H), 7.45 (dd, J=2.1, 8.0 Hz, 1H), 7.19 (d, J=8.0 Hz, 1H), 3.75 (s, 3H), 2.83-2.74 (m, 2H), 2.55-2.45 (m, 2H).

Step 3: Synthesis of Compound WX133-4

Synthesis of Compound WX133-4 was carried out by referring to the synthetic method of Example 3 Step 1, $^1$H NMR (400 MHz, DMSO-d6) δ 7.62-7.53 (m, 3H), 7.25 (d, J=7.4 Hz, 1H), 3.75 (s, 3H), 2.85 (t, J=8.3 Hz, 2H), 1.30 (s, 12H).

Step 4: Synthesis of Compound WX133-5

Synthesis of Compound WX133-5 was carried out by referring to the synthetic method of Example 3 Step 2, $^1$H NMR (400 MHz, DMSO-d6) δ 8.63 (br d, J=4.4 Hz, 1H), 8.04 (s, 1H), 8.02-7.97 (m, 1H), 7.95-7.90 (m, 1H), 7.88-7.82 (m, 1H), 7.61 (br s, 1H), 7.32 (br dd, J=3.5, 7.3 Hz, 2H), 3.76-3.72 (m, 3H), 2.91-2.82 (m, 2H), 2.56-2.51 (m, 2H).

Step 5: Synthesis of Compound WX133-6

Synthesis of Compound WX133-6 was carried out by referring to the synthetic method of Example 5 Step 4, $^1$H NMR (400 MHz, DMSO-d6) δ 12.49 (br s, 1H), 8.67 (d, J=4.8 Hz, 1H), 8.04 (s, 1H), 8.01 (d, J=7.8 Hz, 1H), 7.99-7.95 (m, 1H), 7.90 (br d, J=6.1 Hz, 1H), 7.59 (s, 1H), 7.38-7.33 (m, 2H), 2.88 (t, J=8.3 Hz, 2H), 2.5 (m, 2H).

Step 6: Synthesis of Compound WX133-7

Under a nitrogen atmosphere, to a solution of WX133-6 (100.00 mg, 397.96 μmol) in methanol (10.00 mL) was added Pd/C (10%, 10 mg), and the system was purged with hydrogen gas for several times, and stirred at 25° C. for 5 hours. After the reaction was complete, it was filtered and concentrated. The residue was purified by column chromatography (dichloromethane:methanol=100:1-20:1) to afford Compound WX133-7 (48.00 mg), white solid. $^1$H NMR (400 MHz, DMSO-d6) δ 12.32 (br s, 1H), 8.64 (d, J=4.5 Hz, 1H), 7.94-7.90 (m, 1H), 7.88-7.79 (m, 3H), 7.36-7.28 (m, 1H), 7.19 (d, J=7.8 Hz, 1H), 3.09-3.01 (m, 1H), 2.94 (s, 1H), 2.91-2.80 (m, 3H), 2.75-2.66 (m, 2H), 2.12 (br d, J=10.2 Hz, 1H), 1.85-1.72 (m, 1H).

Step 7: Synthesis of Compound WX133-8

Synthesis of Compound WX133 was carried out by referring to the synthetic method of Example 7 Step 1, $^1$H NMR (400 MHz, DMSO-d6) δ 8.65 (br d, J=5.0 Hz, 1H), 7.95-7.91 (m, 1H), 7.88 (s, 1H), 7.85 (br d, J=7.9 Hz, 1H), 7.89-7.82 (m, 1H), 7.65 (s, 2H), 7.36-7.30 (m, 1H), 7.24 (d, J=7.7 Hz, 1H), 3.77 (s, 3H), 3.53-3.42 (m, 1H), 3.10-2.89 (m, 1H), 3.10-2.89 (m, 1H), 3.14-2.86 (m, 2H), 2.97 (br s, 1H), 2.68 (br s, 1H), 2.70-2.65 (m, 1H), 2.34 (br s, 1H), 2.21-2.13 (m, 1H), 1.81 (br dd, J=5.2, 11.6 Hz, 1H), 1.24 (s, 1H).

Example 18: WX144

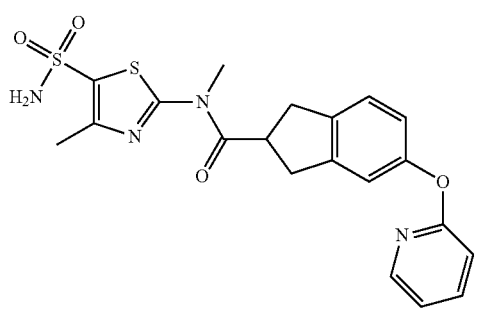 [SMILES: Cc1nc(N(C)C(=O)C2Cc3ccc(Oc4ccccn4)cc3C2)sc1S(N)(=O)=O]

Synthetic Route:

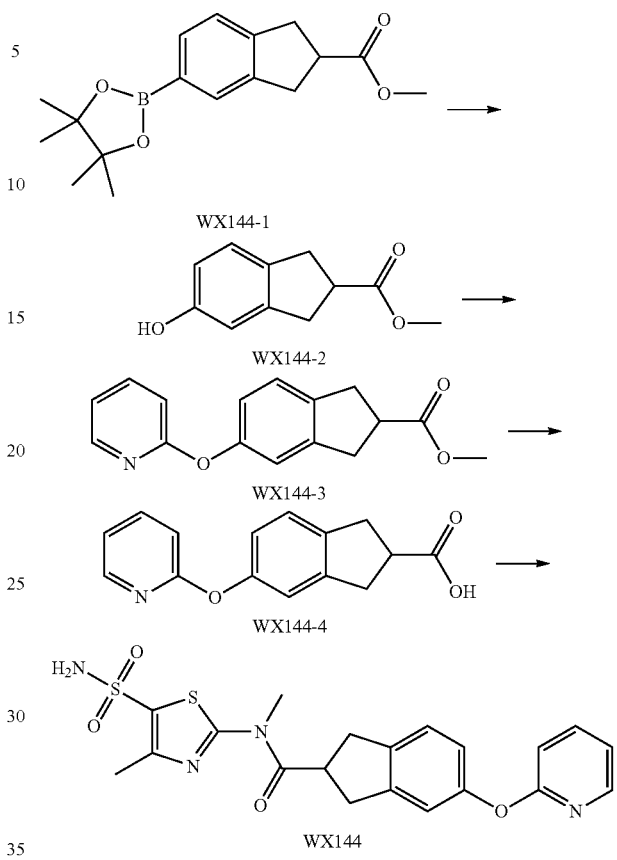

Step 1: Synthesis of Compound WX144-2

At room temperature, to a solution of WX144-1 (500.00 mg, 1.65 mmol) in ethanol/water (2:1, 9.00 mL) was added m-chloroperoxybenzoic acid (298.98 mg, 1.73 mmol), and the system was stirred at 25° C. for 2 hours. After the reaction was complete, 50 mL water was added. The mixture was extracted with ethyl acetate (50 mL×2). The organic phases were combined, dried over anhydrous sodium sulfate, filtered and concentrated. The residue was purified by column chromatography to afford Compound WX144-2 (231.00 mg, 72.73% yield), white solid. $^1$H NMR (400 MHz, CDCl$_3$) δ 7.06 (d, J=8.0 Hz, 1H), 6.71 (s, 1H), 6.66 (dd, J=2.3, 8.0 Hz, 1H), 3.75 (s, 3H), 3.42-3.31 (m, 1H), 3.29-3.08 (m, 4H).

Step 2: Synthesis of Compound WX144-3

At room temperature, to a solution of WX144-2 (140.00 mg, 728.37 μmol) in DMF (2.00 mL) was added 2-fluoropyridine (77.79 mg, 801.21 μmol, 68.84 μL) and potassium carbonate (201.34 mg, 1.46 mmol), and the system was reacted at 120° C. under microwave for 2 hours. After the reaction was complete, 15 mL water was added. The mixture was extracted with ethyl acetate (15 mL×3). The organic phases were combined, dried over anhydrous sodium sulfate, filtered and concentrated. The residue was purified by column chromatography to afford Compound WX144-3 (65.00 mg, 21.11% yield). $^1$H NMR (400 MHz, CDCl$_3$) δ 8.19 (dd, J=1.3, 5.0 Hz, 1H), 7.70-7.64 (m, 1H), 7.21 (d, J=8.0 Hz, 1H), 7.00-6.87 (m, 4H), 3.74 (s, 3H), 3.45-3.34 (m, 1H), 3.30-3.13 (m, 4H).

Step 3: Synthesis of Compound WX144-4

Synthesis of Compound WX144-4 was carried out by referring to the synthetic method of Example 8 Step 4, ¹H NMR (400 MHz, CDCl₃) δ 8.18 (dd, J=1.5, 5.0 Hz, 1H), 7.73-7.63 (m, 1H), 7.20 (d, J=8.0 Hz, 1H), 7.01-6.85 (m, 4H), 3.44-3.33 (m, 1H), 3.28-3.19 (m, 4H).

Step 4: Synthesis of Compound WX144

Synthesis of Compound WX144 was carried out by referring to the synthetic method of Example 7 Step 1, ¹H NMR (400 MHz, DMSO-d6) δ 8.12 (dd, J=1.3, 5.0 Hz, 1H), 7.86-7.78 (m, 1H), 7.64 (br s, 2H), 7.23 (d, J=8.0 Hz, 1H), 7.09 (dd, J=5.0, 6.5 Hz, 1H), 7.01-6.95 (m, 2H), 6.89 (dd, J=2.3, 8.0 Hz, 1H), 4.08 (quin, J=8.0 Hz, 1H), 3.72 (s, 3H), 3.35-3.14 (m, 4H), 2.47 (s, 3H).

Example 19: WX017 and WX018

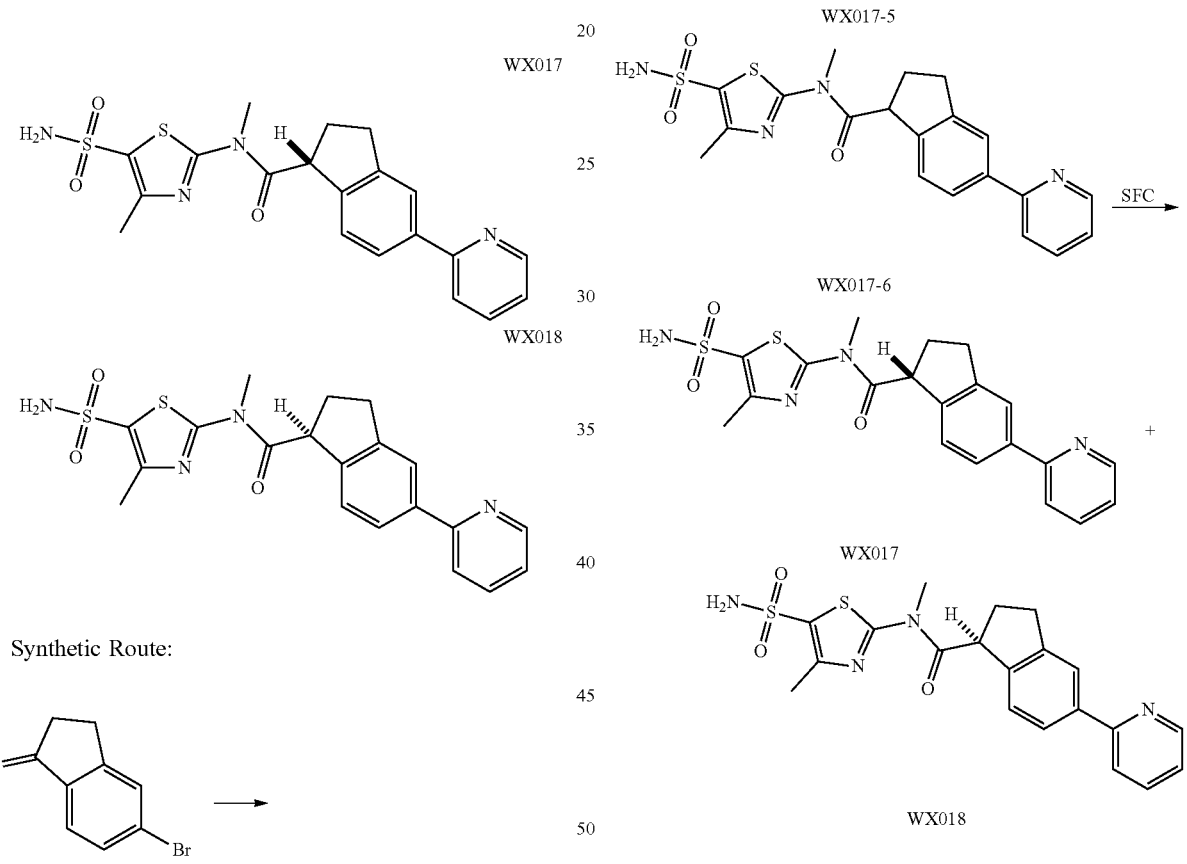

Synthetic Route:

Step 1: Synthesis of Compound WX017-2

At 5° C., to a solution of WX017-1 (5.00 g, 23.69 mmol) in DMF (100.00 mL) was added ethanol (3.27 g, 71.07 mmol) and TosMIC (9.25 g, 47.38 mmol), and then potassium tert-butoxide (9.30 g, 82.92 mmol). The temperature was warmed to room temperature, and the mixture was stirred for 2 hours. After the reaction was complete, 20 mL water was added, and the mixture was adjusted to pH=6 with 1M hydrochloric acid, and extracted with ethyl acetate (20 mL×2). The organic layer was washed with 50 mL brine. The organic phases were combined, dried over anhydrous sodium sulfate, filtered and concentrated. The residue was purified by column chromatography to afford Compound WX017-2 (1.80 g, 31.82% yield). ¹H NMR (400 MHz, CDCl$_3$) δ 7.37-7.45 (m, 1H), 7.31 (s, 1H), 4.06 (t, J=8.28 Hz, 1H), 3.02-3.15 (m, 1H), 2.89-3.01 (m, 1H), 2.53-2.74 (m, 1H), 2.35-2.44 (m, 1H).

Step 2: Synthesis of Compound WX017-3

A solution of WX017-2 (1.80 g, 8.11 mmol) in HCl in methanol (4 M, 30.01 mL) was reacted at 80° C. for 16 hours. After the reaction was complete, it was concentrated under reduced pressure. 50 mL dichloromethane was added, and the solution was washed with 50 mL brine. The organic phase was dried over anhydrous sodium sulfate, filtered and concentrated. The residue was purified by column chromatography to afford Compound WX017-3 (1.80 g, 80.91% yield). $^1$H NMR (400 MHz, CDCl$_3$) δ 7.40 (s, 1H), 7.31-7.35 (m, 1H), 7.25-7.29 (m, 1H), 3.99-4.07 (m, 1H), 3.75 (s, 3H), 3.04-3.15 (m, 1H), 2.92 (dt, J=15.81, 7.65 Hz, 1H), 2.43-2.51 (m, 1H), 2.32-2.41 (m, 1H).

Step 3: Synthesis of Compound WX017-4

Synthesis of Compound WX017-4 was carried out by referring to the synthetic method of Example 5 Step 3. $^1H$ NMR (400 MHz, CDCl$_3$) δ 8.68 (d, J=4.52 Hz, 1H), 7.89 (s, 1H), 7.79 (d, J=8.03 Hz, 1H), 7.68-7.76 (m, 2H), 7.47 (d, J=8.03 Hz, 1H), 7.18-7.25 (m, 1H), 4.11 (t, J=7.28 Hz, 1H), 3.75 (s, 3H), 3.13-3.22 (m, 1H), 2.94-3.05 (m, 1H), 2.46-2.55 (m, 1H), 2.35-2.44 (m, 1H).

Step 4: Synthesis of Compound WX017-5

Synthesis of Compound WX017-5 was carried out by referring to the synthetic method of Example 5 Step 4, $^1$H NMR (400 MHz, METHANOL-d$_4$) δ 8.60 (d, J=4.52 Hz, 1H), 7.88-7.94 (m, 1H), 7.84 (d, J=11.54 Hz, 2H), 7.76 (d, J=8.03 Hz, 1H), 7.52 (d, J=8.03 Hz, 1H), 7.34-7.40 (m, 1H), 4.10 (t, J=7.53 Hz, 1H), 3.11-3.22 (m, 1H), 2.95-3.07 (m, 1H), 2.36-2.51 (m, 2H).

Step 5: Synthesis of Compound WX017-6

Synthesis of Compound WX017-6 was carried out by referring to the synthetic method of Example 7 Step 1, $^1$H NMR (400 MHz, DMSO-d6) δ 8.64 (d, J=3.76 Hz, 1H), 7.99 (s, 1H), 7.83-7.95 (m, 3H), 7.64 (s, 2H), 7.27-7.37 (m, 2H), 4.86 (br. s., 1H), 3.86 (s, 3H), 2.97-3.10 (m, 2H), 2.53 (br. s., 1H), 2.46-2.49 (m, 3H), 2.28 (dd, J=12.17, 7.65 Hz, 1H).

Step 6: Synthesis of Compounds WX017 and WX018

At room temperature, to a solution of WX017-6 (300.00 mg, 700.07 μmol) in methanol (10 mL) was added HCl in methanol (4 M, 350.04 μL), and the system was stirred for 10 mins, and concentrated under reduced pressure. The residue was chirally resolved by supercritical fluid chromatography (separation condition: column: AS (250 mm*30 mm, 5 um); mobile phase: [0.1% NH$_3$H$_2$O MeOH]; B %: 40%-40%), to afford rotational isomers WX017 and WX018. Their retention time was respectively 7.5 min, and 8.7 min Compound WX017 (65.00 mg, 21.02% yield), $^1$H NMR (400 MHz, DMSO-d6) δ 8.64 (d, J=3.76 Hz, 1H), 7.99 (s, 1H), 2.23-2.33 (m, 1H) 7.83-7.94 (m, 3H), 7.64 (s, 2H), 7.27-7.35 (m, 2H), 4.86 (t, J=7.65 Hz, 1H), 3.32 (s, 3H), 2.95-3.14 (m, 2H), 2.54 (d, J=8.03 Hz, 1H), 2.44-2.49 (m, 3H) and Compound WX018 (60.90 mg, 19.89% yield), $^1$H NMR (400 MHz, DMSO-d6) δ 8.66 (d, J=4.02 Hz, 1H), 8.02 (s, 1H), 7.96 (m, 3H), 7.65 (s, 2H), 7.34 (m, 2H), 4.89 (t, J=7.78 Hz, 1H), 3.89 (s, 3H), 2.97-3.17 (m, 2H), 2.59 (m, 1H), 2.52-2.54 (m, 3H), 2.31 (m, 1H).

Example 20: WX030 and WX031

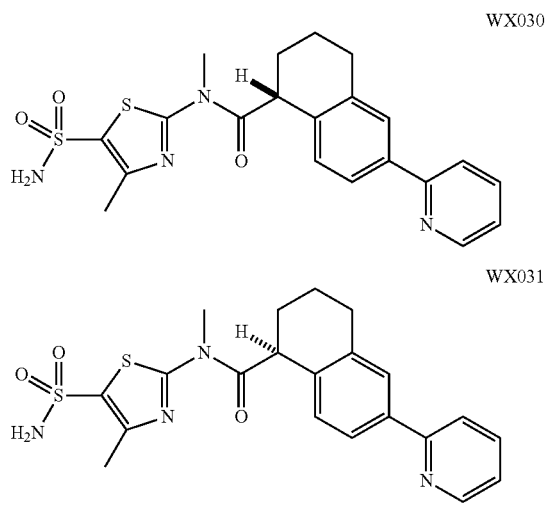

Synthetic Route:

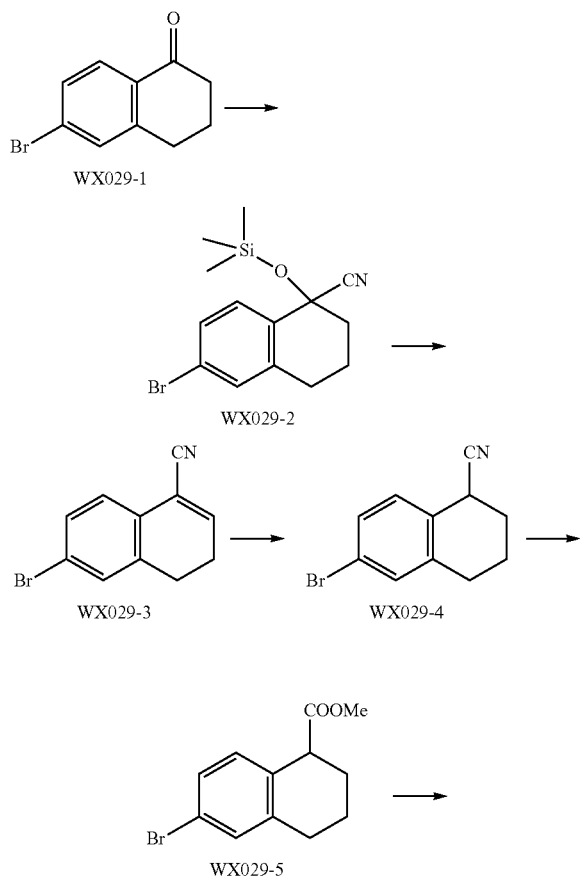

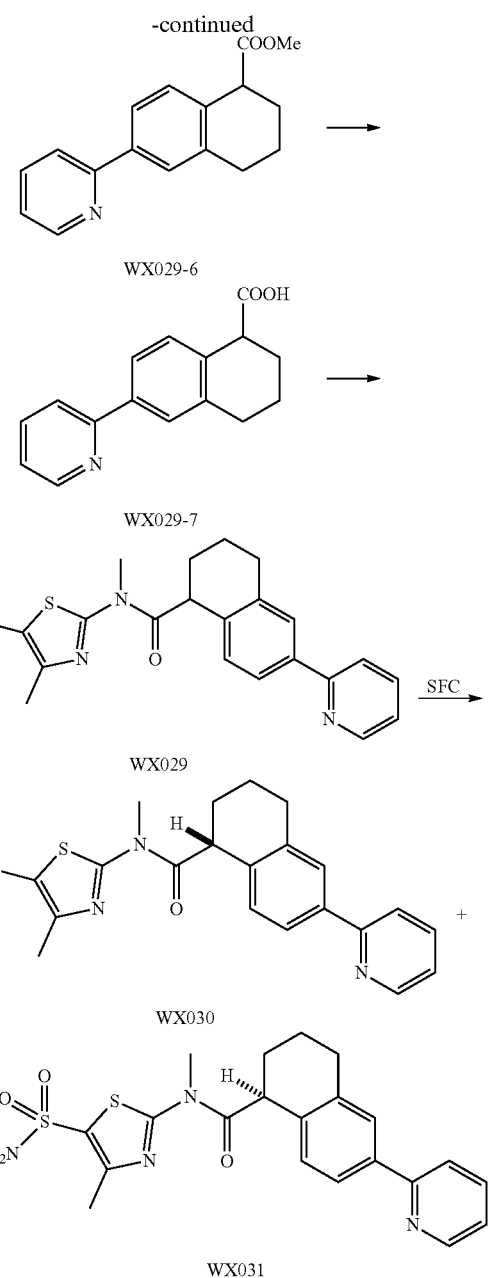

Step 2: Synthesis of Compound WX029-3

At 0° C., to WX029-2 (4.70 g, 14.49 mmol) was added sulphuric acid (55.20 g, 551.55 mmol), and the system was stirred at 20° C. for 10 mins After the reaction was complete, the reaction mixture was poured into 200 mL ice water. The reaction mixture was extracted with dichloromethane (100 mL×2). The organic phase was washed separately with 200 mL carbonic acid solution and 200 mL brine. The organic phase was dried over anhydrous sodium sulfate, filtered and concentrated. The residue was purified by column chromatography to afford Compound WX029-3 (3.00 g, 76.06% yield). $^1$H NMR (400 MHz, CDCl$_3$) δ 7.42 (d, J=9.54 Hz, 1H), 7.29-7.34 (m, 2H), 6.91 (t, J=4.77 Hz, 1H), 2.84 (t, J=8.03 Hz, 2H), 2.50 (td, J=8.16, 4.77 Hz, 2H).

Step 3: Synthesis of Compound WX029-4

To a solution of WX029-3 (3.00 g, 12.82 mmol) in methanol (50.00 mL) was added sodium borohydride (2.91 g, 76.92 mmol), and the system was stirred at 80° C. for 30 mins After the reaction was complete, to the system was added 100 mL water and 100 mL dichloromethane. The organic layer was washed with 100 mL brine. The organic phase was dried over anhydrous sodium sulfate, filtered and concentrated. The residue was purified by column chromatography to afford Compound WX029-4 (2.20 g, 65.44% yield). $^1$H NMR (400 MHz, CDCl$_3$) (57.34 (d, J=8.03 Hz, 1H), 7.30 (s, 1H), 7.22-7.27 (m, 1H), 3.92 (t, J=6.27 Hz, 1H), 2.74-2.86 (m, 2H), 2.11-2.18 (m, 2H), 1.99-2.06 (m, 1H), 1.79-1.88 (m, 1H).

Step 4: Synthesis of Compound WX029-5

A solution of WX029-4 (2.20 g, 9.32 mmol) in HCl in methanol (4 M, 50.00 mL) was stirred at 80° C. for 16 hours. After the reaction was complete, it was concentrated under reduced pressure, dissolved in 100 mL dichloromethane, and washed with 100 mL brine. The organic phase was dried over anhydrous sodium sulfate, filtered and concentrated. The residue was purified by column chromatography to afford Compound WX029-5 (1.50 g, 55.04% yield), yellow liquid. $^1$H NMR (400 MHz, CDCl$_3$) (57.23-7.28 (m, 1H), 7.04 (d, J=8.03 Hz, 1H), 3.77 (t, J=5.77 Hz, 1H), 3.72 (s, 3H), 2.65-2.90 (m, 2H), 2.09-2.20 (m, 1H), 1.90-2.02 (m, 2H), 1.71-1.80 (m, 1H).

Step 5: Synthesis of Compound WX029-6

Synthesis of Compound WX029-6 was carried out by referring to the synthetic method of Example 5 Step 3. $^1$H NMR (400 MHz, CDCl$_3$) δ 8.70 (d, J=4.77 Hz, 1H), 7.80 (s, 1H), 7.73-7.76 (m, 2H), 7.28-7.31 (m, 1H), 7.21-7.26 (m, 1H), 3.91 (t, J=5.77 Hz, 1H), 3.75 (s, 3H), 2.81-3.00 (m, 2H), 2.20 (br. s., 1H), 1.98-2.10 (m, 2H), 1.77-1.88 (m, 1H).

Step 6: Synthesis of Compound WX029-7

Synthesis of Compound WX029-7 was carried out by referring to the synthetic method of Example 5 Step 4, $^1$H NMR (400 MHz, METHANOL-d$_4$) δ8.60 (d, J=4.52 Hz, 1H), 7.88-7.94 (m, 1H), 7.82-7.87 (m, 1H), 7.67-7.71 (m, 2H), 7.31-7.39 (m, 2H), 3.87 (t, J=5.90 Hz, 1H), 2.83-2.99 (m, 2H), 2.18 (t, J=5.27 Hz, 1H), 1.98-2.12 (m, 2H), 1.84 (d, J=11.54 Hz, 1H).

Step 7: Synthesis of Compound WX029

Synthesis of Compound WX029 was carried out by referring to the synthetic method of Example 7 Step 1, $^1$H Step 1: Synthesis of Compound WX029-2

At 20° C., to a solution of WX029-1 (3.70 g, 16.44 mmol) and TMSCN (16.31 g, 164.39 mmol) was added zinc iodide (1.57 g, 4.93 mmol), and the system was stirred for 16 hours. After the reaction was complete, 50 mL ethyl acetate was added to dilute the reaction mixture. The mixture was separately washed with 100 mL saturated aqueous sodium carbonate solution and 50 mL brine. The organic phase was dried over anhydrous sodium sulfate, filtered and concentrated. The residue was purified by column chromatography to afford Compound WX029-2 (4.70 g, 79.32% yield). $^1$H NMR (400 MHz, CDCl$_3$) δ 7.54 (d, J=8.53 Hz, 1H), 7.41 (d, J=8.53 Hz, 1H), 7.30 (s, 1H), 2.32-2.40 (m, 1H), 2.18 (dd, J=12.92, 9.54, 3.14 Hz, 1H), 1.94-2.10 (m, 2H), 0.26 (s, 9H).

NMR (400 MHz, DMSO-d6) δ8.66 (d, J=4.02 Hz, 1H), 7.93 (s, 1H), 7.89 (s, 2H), 7.81 (s, 1H), 7.65 (s, 2H), 7.28-7.39 (m, 1H), 7.11 (d, J=8.53 Hz, 1H), 4.67 (s, 1H), 3.87 (s, 3H), 2.89 (d, J=6.53 Hz, 2H), 2.50-2.51 (m, 3H), 2.16 (d, J=4.02 Hz, 1H), 2.09 (s, 1H), 1.92-2.01 (m, 1H), 1.84 (d, J=4.02 Hz, 2H).

Step 8: Synthesis of Compounds WX030 and WX031

Compound WX029 was chirally resolved by supercritical fluid chromatography (Instrument: SFC-80; Column:OD (250 mm*30 mm, 10 μm); mobile phase: supercritical CO$_2$/MeOH (0.1% NH$_3$H$_2$O)=45/55; flow rate 70 mL/min; column temperature: 38° C.), to afford rotational isomers WX030 and WX031. Their retention time was respectively 2.1 min and 2.5 min Compound WX030, $^1$H NMR (400 MHz, DMSO-d6) δ 8.64 (d, J=4.52 Hz, 1H), 8.64 (d, J=4.52 Hz, 1H), 7.93 (m, 1H), 7.86 (m, 2H), 7.79 (d, J=8.28 Hz, 1H), 7.62 (s, 2H), 7.32 (dd, J=6.53, 5.02 Hz, 1H), 7.09 (d, J=8.28 Hz, 1H), 4.65 (t, J=6.40 Hz, 1H), 3.84 (s, 3H), 2.87 (m, 2H), 2.53 (m, 3H), 2.15 (m, 1H), 1.86 (m, 3H) and WX031, $^1$H NMR (400 MHz, DMSO-d6) δ 8.64 (d, J=4.52 Hz, 1H), 7.92 (m, 1H), 7.86 (m, 2H), 7.79 (d, J=8.03 Hz, 1H), 7.62 (s, 2H), 7.32 (dd, J=6.78, 5.27 Hz, 1H), 7.09 (d, J=8.28 Hz, 1H), 4.65 (t, J=6.40 Hz, 1H), 3.84 (s, 3H), 2.86 (q, J=6.78 Hz, 2H), 2.53 (m, 3H), 2.16 (m, 1H), 1.87 (m, 3H).

Example 21: WX036 and WX037

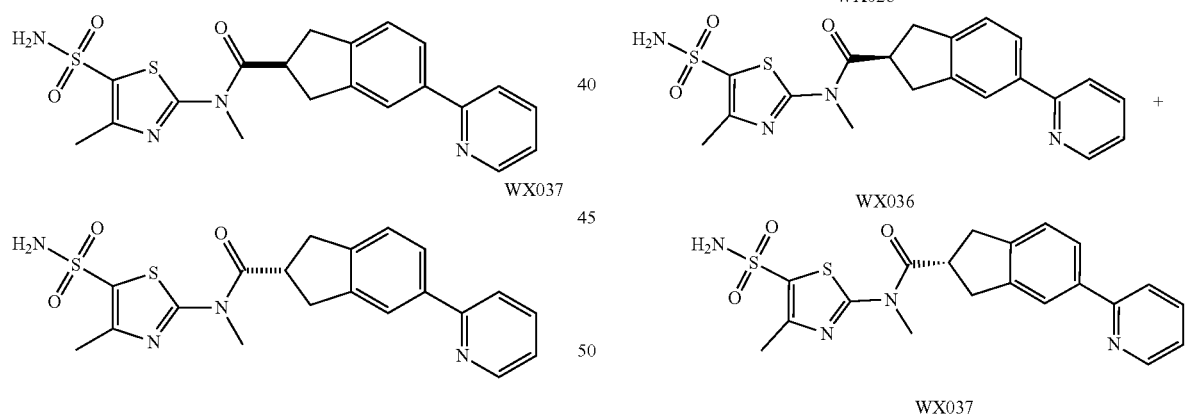

Synthetic Route:

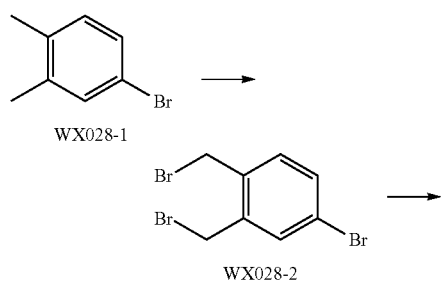

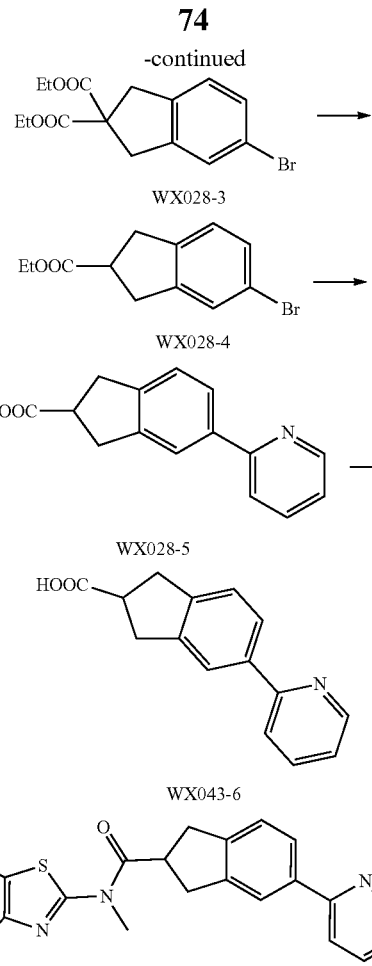

Step 1: Synthesis of Compound WX028-2

To a solution of WX028-1 (30.00 g, 162.11 mmol) in carbon tetrachloride (400.00 mL) was added NBS (57.70 g, 324.22 mmol) and AIBN (5.32 g, 32.42 mmol), and the system was stirred at 80° C. for 2 hours. After the reaction was complete, it was concentrated under reduced pressure. The residue was purified by column chromatography to afford Compound WX028-2 (37 g, crude product), colorless oil. $^1$H NMR (400 MHz, CDCl$_3$) δ 7.55 (s, 1H), 7.47-7.45 (m, 1H), 7.28-7.25 (m, 1H), 4.62 (s, 2H), 4.60 (s, 2H).

Step 2: Synthesis of Compound WX028-3

Synthesis of Compound WX028-3 was carried out by referring to the synthetic method of Example 9 Step 2, ¹H NMR (400 MHz, DMSO-d6) δ 7.36 (s, 1H), 7.34-7.32 (m, 1H), 7.22-7.12 (m, 1H), 4.13 (q, J1=14.0 Hz, J2=7.2 Hz, 6H), 1.18-1.14 (m, 8H).

Step 3: Synthesis of Compound WX028-4

Synthesis of Compound WX028-4 was carried out by referring to the synthetic method of Example 9 Step 3, ¹H NMR (400 MHz, DMSO-d6) δ 7.40 (s, 1H), 7.29 (d, J=8.0 Hz, 1H), 7.15 (d, J=8.0 Hz, 1H), 4.07 (t, J=14.0 Hz, 2H), 3.42-3.35 (m, 1H), 3.16-3.04 (m, 4H), 1.18 (t, J=15.6 Hz, 3H).

Step 4: Synthesis of Compound WX028-5

Synthesis of Compound WX028-5 was carried out by referring to the synthetic method of Example 5 Step 3, ¹H NMR (400 MHz, DMSO-d6) δ 8.62 (d, J=6.4 Hz, 1H), 7.92-7.81 (m, 4H), 7.29 (d, J=5.2 Hz, 2H), 4.09 (q, J1=18.0 Hz, J2=6.8 Hz, 2H), 3.40-3.23 (m, 1H), 3.21-3.15 (m, 4H), 1.20 (t, J=14.4 Hz, 3H).

Step 5: Synthesis of Compound WX028-6

Synthesis of Compound WX028-6 was carried out by referring to the synthetic method of Example 5 Step 4, ¹H NMR (400 MHz, DMSO-d6) δ 8.63 (d, J=4.4 Hz, 1H), 7.94-7.83 (m, 4H), 7.34-7.31 (m, 2H), 3.30-3.00 (m, 1H), 3.22-3.16 (m, 4H).

Step 6: Synthesis of Compound WX028

Synthesis of Compound WX028 was carried out by referring to the synthetic method of Example 7 Step 1, ¹H NMR (400 MHz, CDCl₃) δ 12.26 (br, 1H), 8.70 (d, J=4.0 Hz, 1H), (s, 1H), 7.81-7.71 (m, 3H), 7.34 (d, J=8.0 Hz, 1H), 7.26-7.25 (m, 1H), (s, 2H), 3.91-3.83 (m, 1H), 3.79 (s, 3H), 3.45-3.35 (m, 4H), 2.60 (s, 3H).

Step 7: Synthesis of Compounds WX036 and WX037

Compound WX028 (690.00 mg, 1.61 mmol) was chirally resolved by supercritical fluid chromatography (Instrument: SFC-10; Column: AD (250 mm*50 mm, 10 μm); mobile phase: supercritical CO₂/MeOH (0.1% NH₃H₂O)=55/45; flow rate 180 mL/min; column temperature: 38° C.), to afford rotational isomers WX036 and WX037. Their retention time was respectively 1.2 min and 1.7 min Compound WX036 (134.00 mg, 19.11% yield, 98.37% purity), ¹H NMR (400 MHz, DMSO-d6) δ 8.62 (d, J=3.2 Hz, 1H), 7.94-7.82 (m, 4H), 7.64 (s, 2H), 7.34-7.29 (m, 2H), 4.09-4.06 (m, 1H), 3.74 (s, 3H), 3.32-3.26 (m, 4H), 2.45 (s, 3H) and Compound WX037 (13.00 mg, 1.86% yield, 98.54% purity), ¹H NMR (400 MHz, DMSO-d6) δ 8.62 (d, J=3.2 Hz, 1H), 7.94-7.82 (m, 4H), 7.63 (s, 2H), 7.34-7.29 (m, 2H), 4.09-4.06 (m, 1H), 3.74 (s, 3H), 3.32-3.26 (m, 4H), 2.45 (s, 3H).

Example 22: WX158 and WX159

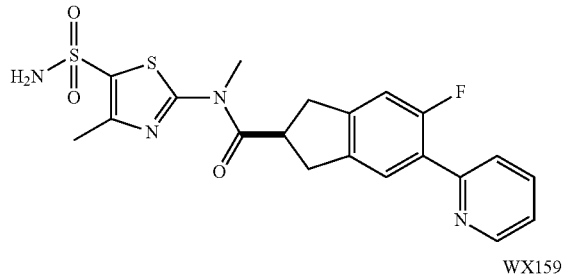

WX158

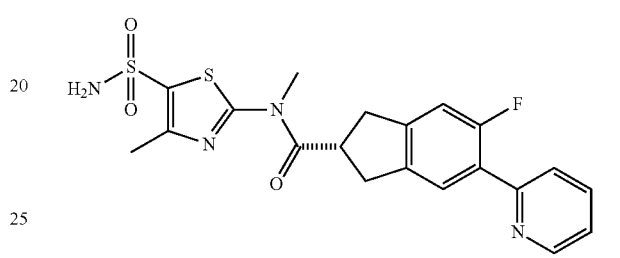

WX159

Synthetic Route:

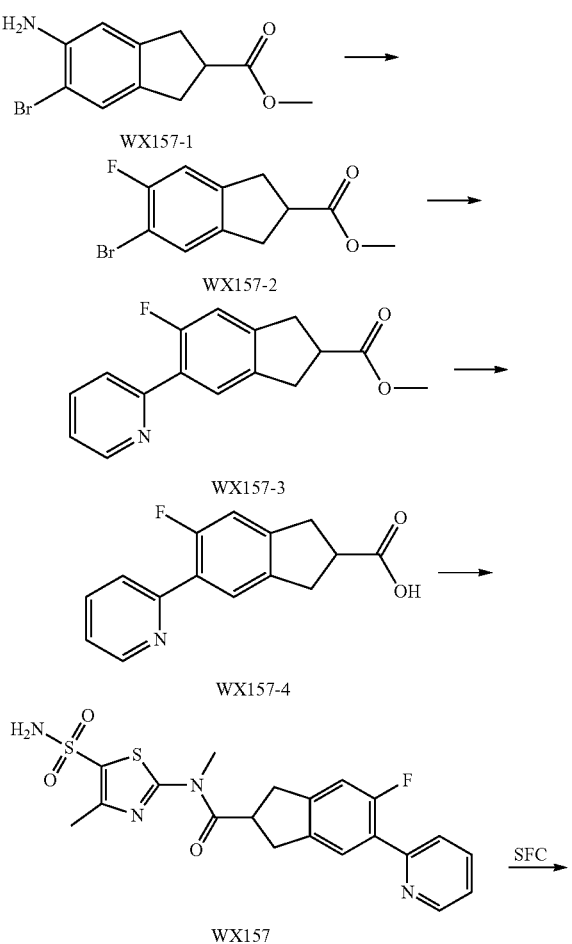

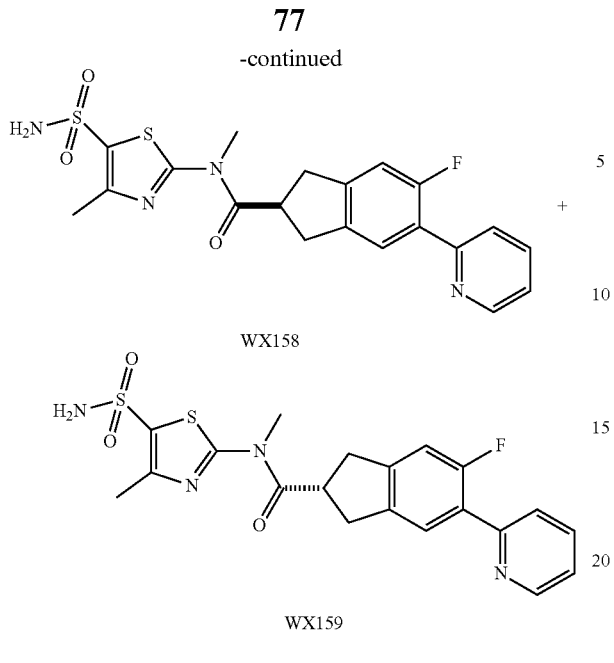

WX158

WX159

Step 1: Synthesis of Compound WX157-2

At −10° C., to a solution of WX157-1 (1.00 g, 3.70 mmol) in tetrahydrofuran (2.00 mL) was added boron trifluoride-.hydrofluoride (1.41 g, 16.07 mmol, 1.00 mL), and the system was stirred for 30 mins. Then tert-butyl nitrite (1.41 g, 16.07 mmol, 1.00 mL) was added dropwise, and the system was stirred for 30 mins After the reaction was complete, it was filtered. The filter cake was washed with 10 mL tetrahydrofuran and 10 mL petroleum ether, and then dried to afford 740 mg solid, and decomposed at 150° C. for 1 hour. After cooling to room temperature, 50 mL water was added. The mixture was extracted with ethyl acetate (50 mL×3). The organic phase was dried over anhydrous sodium sulfate, and concentrated under reduced pressure. The residue was purified by column chromatography to afford Compound WX157-2 (141.00 mg, 13.95% yield), white solid. $^1$H NMR (400 MHz, CDCl$_3$) δ 7.29 (d, J=6.3 Hz, 1H), 6.89 (d, J=8.5 Hz, 1H), 3.66 (s, 3H), 3.35-3.25 (m, 1H), 3.16-3.07 (m, 4H).

Step 2: Synthesis of Compound WX157-3

Synthesis of Compound WX157-3 was carried out by referring to the synthetic method of Example 5 Step 3.

Step 3: Synthesis of Compound WX157-4

Synthesis of Compound WX157-4 was carried out by referring to the synthetic method of Example 8 Step 4, $^1$H NMR (400 MHz, CDCl3) δ 8.64 (br s, 2H), 8.33 (br d, J=7.3 Hz, 1H), 7.76 (br t, J=7.7 Hz, 1H), 7.24 (br d, J=5.8 Hz, 1H), 6.94 (br d, J=11.3 Hz, 1H), 3.35-3.07 (m, 5H).

Step 4: Synthesis of Compound WX157

Synthesis of Compound WX157 was carried out by referring to the synthetic method of Example 7 Step 1.

Step 5: Synthesis of Compounds WX158 and WX159

Compound WX157 was chirally resolved by supercritical fluid chromatography (separation condition: column: OD (250 mm*30 mm, 10 um); mobile phase: supercritical CO$_2$/MeOH (0.1% NH$_3$H$_2$O), B %: 55%-55%), to afford rotational isomers WX158 and WX159. Their retention time was respectively 1.2 min and 2.7 min Compound WX158 $^1$H NMR (400 MHz, DMSO-d6) δ 8.70 (br d, J=4.0 Hz, 1H), 7.89 (dt, J=1.8, 7.7 Hz, 1H), 7.76 (br d, J=7.0 Hz, 2H), 7.65 (s, 2H), 7.39 (dd, J=4.9, 6.7 Hz, 1H), 7.22 (d, J=11.3 Hz, 1H), 4.18-4.07 (m, 1H), 3.75 (s, 3H), 3.33-3.16 (m, 4H), 2.55-2.52 (m, 3H) and WX159 $^1$H NMR (400 MHz, DMSO-d6) δ 8.70 (br d, J=4.0 Hz, 1H), 7.89 (dt, J=1.8, 7.7 Hz, 1H), 7.76 (br d, J=7.0 Hz, 2H), 7.65 (s, 2H), 7.39 (dd, J=4.9, 6.7 Hz, 1H), 7.22 (d, J=11.3 Hz, 1H), 4.18-4.07 (m, 1H), 3.75 (s, 3H), 3.33-3.16 (m, 4H), 2.55-2.52 (m, 3H).

Example 23: WX154 and WX155

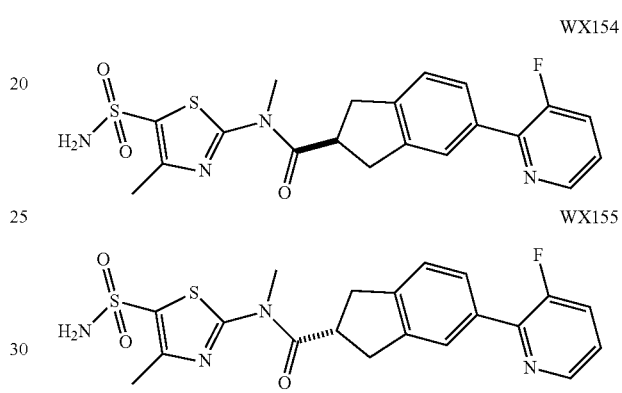

WX154

WX155

Synthetic Route:

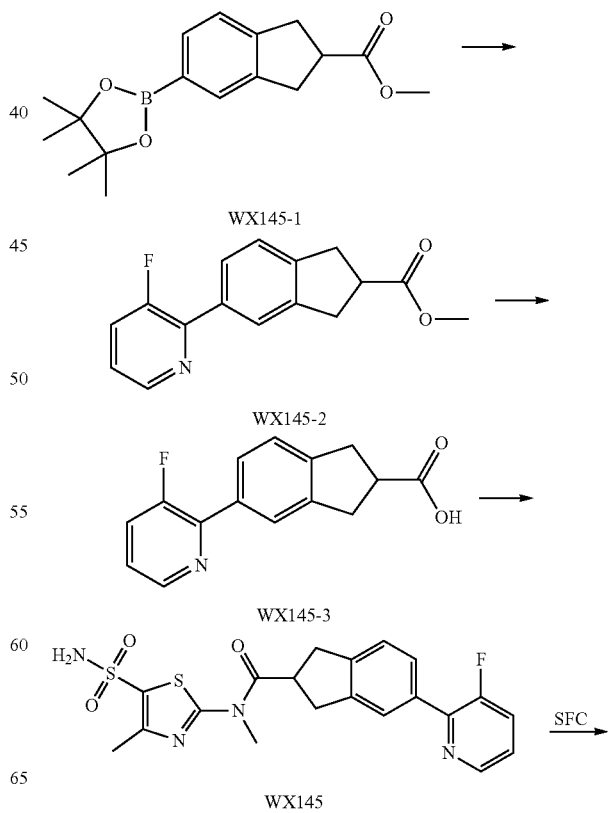

-continued

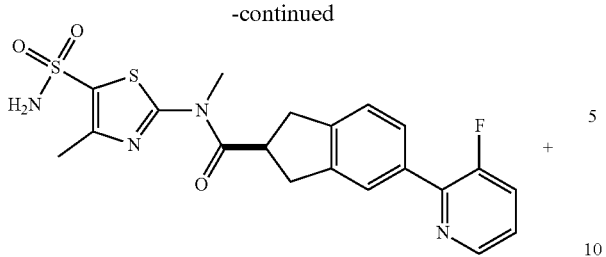

WX154

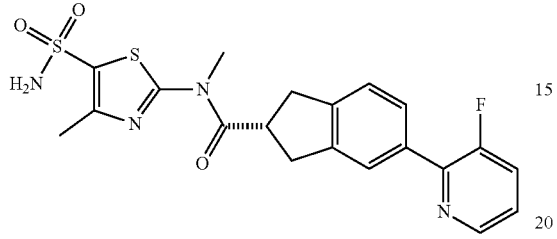

WX155

Step 1: Synthesis of Compound WX145-2

Synthesis of Compound WX145-2 was carried out by referring to the synthetic method of Example 3 Step 2, $^1$H NMR (400 MHz, DMSO-d6) δ 8.56-8.50 (m, 1H), 7.81 (ddd, J=0.8, 8.4, 11.7 Hz, 1H), 7.76 (s, 1H), 7.71 (d, J=7.8 Hz, 1H), 7.45 (td, J=4.2, 8.3 Hz, 1H), 7.36 (d, J=7.8 Hz, 1H), 3.66 (s, 3H), 3.44 (q, J=8.3 Hz, 1H), 3.29-3.14 (m, 4H).

Step 2: Synthesis of Compound WX145-3

Synthesis of Compound WX145-3 was carried out by referring to the synthetic method of Example 8 Step 4, $^1$H NMR (400 MHz, DMSO-d6) δ 12.34 (br s, 1H), 8.56-8.50 (m, 1H), 7.86-7.79 (m, 1H), 7.76 (s, 1H), 7.71 (br d, J=8.0 Hz, 1H), 7.46 (td, J=4.1, 8.4 Hz, 1H), 7.37 (d, J=7.8 Hz, 1H), 3.41-3.36 (m, 1H), 3.27-3.16 (m, 4H).

Step 3: Synthesis of Compound WX145

Synthesis of Compound WX145 was carried out by referring to the synthetic method of Example 7 Step 1. $^1$H NMR (400 MHz, DMSO-d6) δ 8.53 (d, J=4.5 Hz, 1H), 7.83 (dd, J=8.4, 11.7 Hz, 1H), 7.78 (s, 1H), 7.73 (br d, J=7.8 Hz, 1H), 7.65 (s, 2H), 7.47 (td, J=4.1, 8.3 Hz, 1H), 7.39 (d, J=7.8 Hz, 1H), 4.11 (quin, J=8.0 Hz, 1H), 3.76 (s, 3H), 3.40-3.25 (m, 4H), 2.54-2.52 (m, 3H).

Step 4: Synthesis of Compounds WX154 and WX155

Compound WX145 was chirally resolved by supercritical fluid chromatography (separation condition: column: AD (250 mm*30 mm, 10 μm); mobile phase: supercritical CO$_2$/IPA (0.1% NH$_3$H$_2$O), B %: 55%-55%), to afford rotational isomers WX154 and WX155. Their retention time was respectively 1.7 min and 2.5 min Compound WX154 $^1$H NMR (400 MHz, DMSO-d6) δ 8.54 (br d, J=4.8 Hz, 1H), 7.86-7.77 (m, 2H), 7.73 (d, J=7.8 Hz, 1H), 7.46 (td, J=4.1, 8.3 Hz, 1H), 7.39 (d, J=7.8 Hz, 1H), 4.11 (br t, J=7.8 Hz, 1H), 3.76 (s, 3H), 3.32-3.29 (m, 4H), 2.48 (br s, 3H) and Compound WX155 $^1$H NMR (400 MHz, DMSO-d6) 8.54 (br d, J=4.8 Hz, 1H), 7.86-7.77 (m, 2H), 7.73 (d, J=7.8 Hz, 1H), 7.46 (td, J=4.1, 8.3 Hz, 1H), 7.39 (d, J=7.8 Hz, 1H), 4.11 (br t, J=7.8 Hz, 1H), 3.76 (s, 3H), 3.32-3.29 (m, 4H), 2.48 (br s, 3H).

Example 24: WX152 and WX153

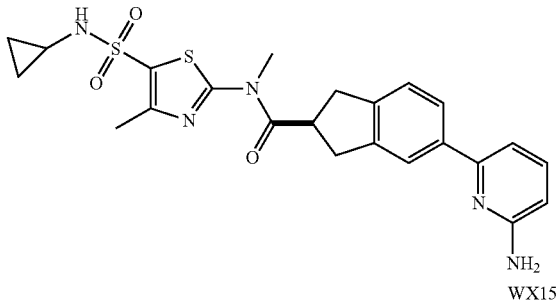

WX152

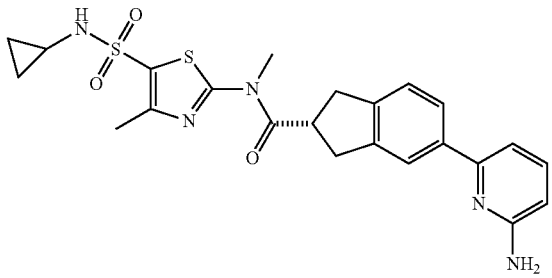

WX153

Synthetic Route:

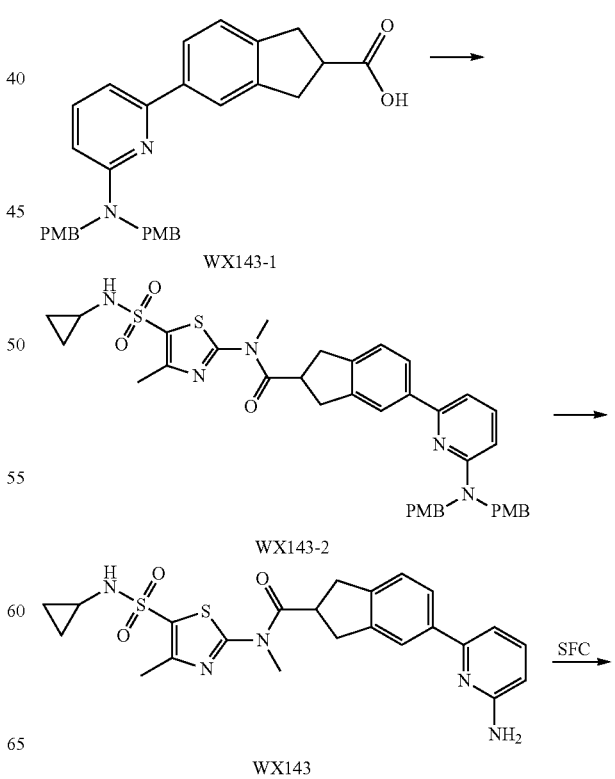

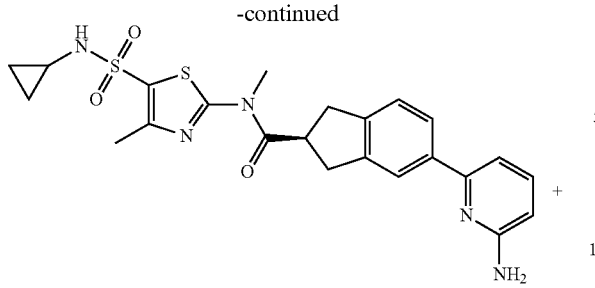

WX152

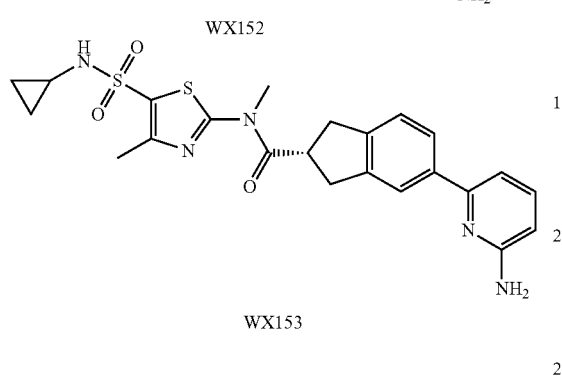

WX153

Step 1: Synthesis of Compound WX143-2

Synthesis of Compound WX143-2 was carried out by referring to the synthetic method of Example 7 Step 1. $^1$H NMR (400 MHz, CDCl3) δ 7.91-7.83 (m, 2H), 7.47-7.41 (m, 1H), 7.28 (s, 1H), 7.23-7.18 (m, 4H), 7.04 (d, J=7.3 Hz, 1H), 6.86-6.82 (m, 4H), 6.41 (d, J=8.5 Hz, 1H), 4.79 (s, 4H), 3.83 (s, 2H), 3.90-3.81 (m, 1H), 3.79 (s, 6H), 3.51-3.25 (m, 4H), 2.61 (s, 3H), 2.40-2.32 (m, 1H), 0.70-0.62 (m, 3H), 0.74-0.56 (m, 1H).

Step 2: Synthesis of Compound WX143

A solution of WX143-2 (220.00 mg, 303.91 μmol) in trifluoroacetic acid (7.70 g, 67.53 mmol, 5.00 mL) was stirred at room temperature for 16 hours. After the reaction was complete, it was concentrated under reduced pressure. The residue was purified by preparative chromatography to afford Compound WX143 (71.00 mg, 45.02% yield), light yellow solid. $^1$H NMR (400 MHz, DMSO-d6) δ 8.13 (d, J=2.5 Hz, 1H), 7.94 (dd, J=7.7, 8.7 Hz, 1H), 7.81 (s, 1H), 7.74 (d, J=8.0 Hz, 1H), 7.44 (d, J=8.0 Hz, 1H), 7.19 (d, J=7.3 Hz, 1H), 6.94 (d, J=8.8 Hz, 1H), 4.17-4.04 (m, 1H), 3.76 (s, 3H), 3.37-3.24 (m, 4H), 2.48 (br s, 3H), 2.19 (qt, J=3.4, 6.6 Hz, 1H), 0.56-0.33 (m, 4H).

Step 3: Synthesis of Compound WX152 and WX153

Compound WX143 (60 mg) was chirally resolved by supercritical fluid chromatography (separation condition: column: AS (250 mm*30 mm, 5 um); mobile phase: supercritical CO$_2$/MeOH (0.1% NH$_3$H$_2$O), B %: 40%-40%), to afford rotational isomers WX152 and WX153. Their retention time was respectively 3.9 min and 4.8 min Compound WX152 (15 mg), $^1$H NMR (400 MHz, DMSO-d6) δ 8.14 (d, J=2.5 Hz, 1H), 7.95 (br s, 1H), 7.75 (br s, 1H), 7.69 (br s, 1H), 7.47 (d, J=7.3 Hz, 1H), 7.19 (br d, J=7.8 Hz, 1H), 6.92 (br s, 1H), 4.12 (br d, J=6.8 Hz, 1H), 3.78 (s, 3H), 3.30 (br s, 4H), 2.54-2.53 (m, 3H), 2.21 (br d, J=2.8 Hz, 1H), 0.55-0.46 (m, 2H), 0.45-0.38 (m, 2H) and Compound WX153 (15 mg), $^1$H NMR (400 MHz, DMSO-d6) δ 8.14 (d, J=2.5 Hz, 1H), 7.95 (br s, 1H), 7.75 (br s, 1H), 7.69 (br s, 1H), 7.47 (d, J=7.3 Hz, 1H), 7.19 (br d, J=7.8 Hz, 1H), 6.92 (br s, 1H), 4.12 (br d, J=6.8 Hz, 1H), 3.78 (s, 3H), 3.30 (br s, 4H), 2.54-2.53 (m, 3H), 2.21 (br d, J=2.8 Hz, 1H), 0.55-0.46 (m, 2H), 0.45-0.38 (m, 2H).

Example 25: WX146 and WX147

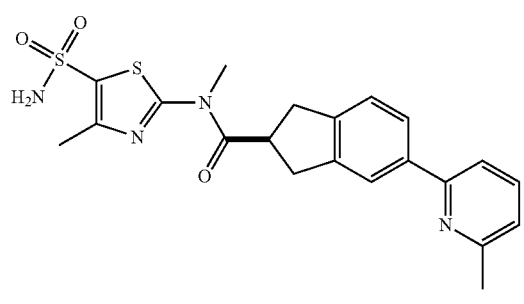

WX146

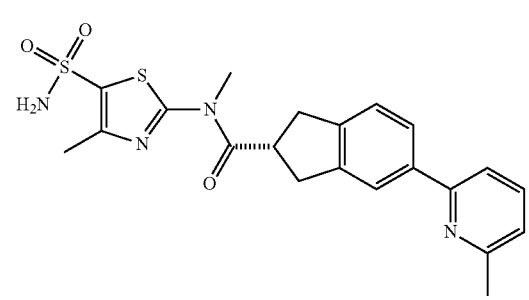

WX147

Synthetic Route:

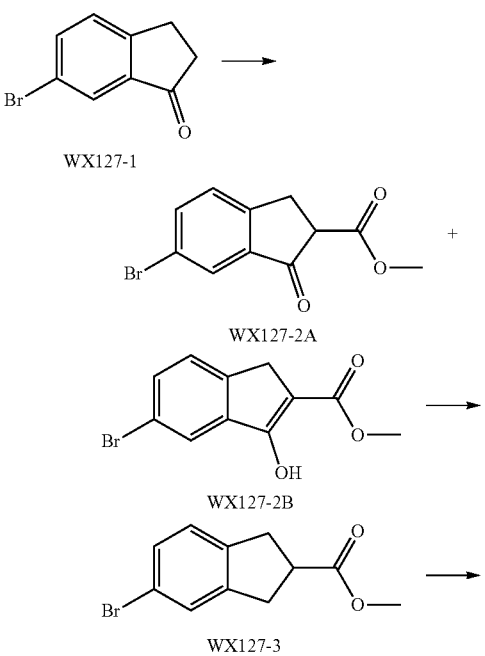

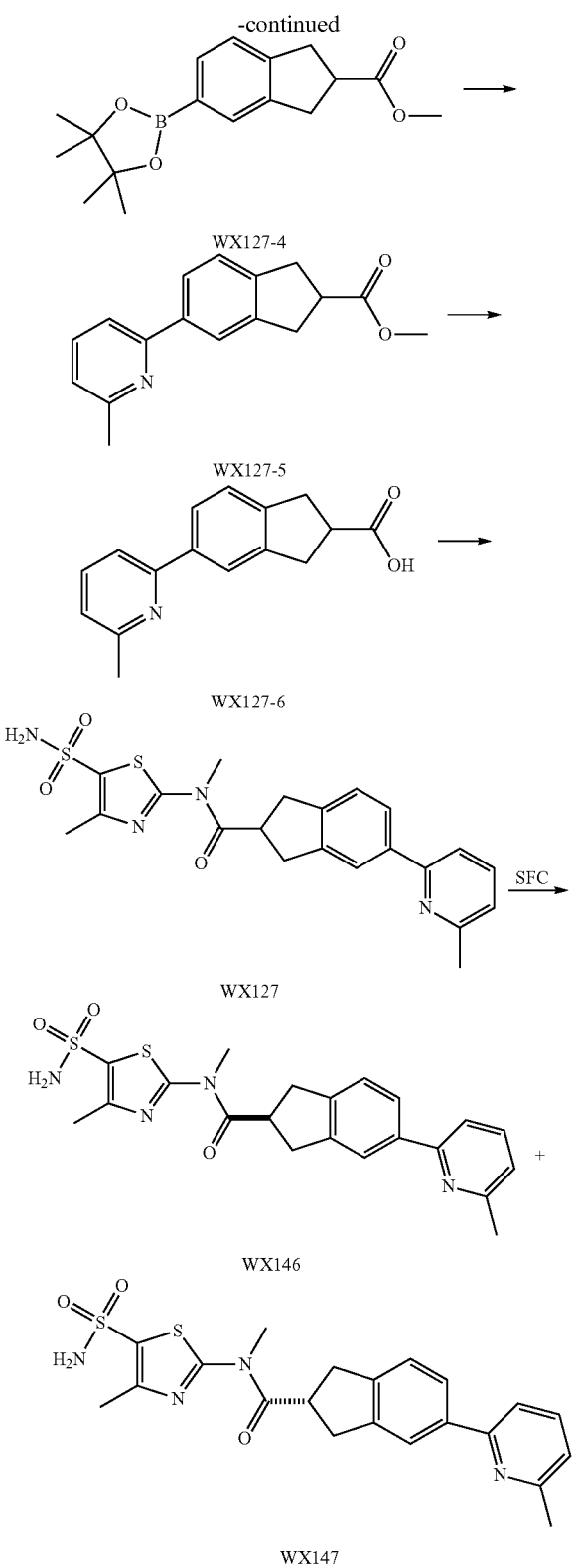

added a solution of WX127-1 (30.00 g, 142.14 mmol) in tetrahydrofuran (200.00 mL) dropwise, stirred for 15 mins, and then dimethyl carbonate (64.02 g, 710.70 mmol, 59.83 mL) was added dropwise, and the system was stirred at 45° C. for 0.5 hour. After the reaction was complete, to the system was added 500 mL 1M hydrochloric acid dropwise. The mixture was extracted with ethyl acetate (1000 mL×3), dried over anhydrous sodium sulfate, filtered and concentrated to afford Compound WX127-2A and WX127-2B as a mixture of 36 g.

Step 2: Synthesis of Compound WX127-3

Under a nitrogen atmosphere, at 0° C., to a solution of 15 g mixture of WX127-2A and WX127-2B in trifluoroacetic acid (231.46 g, 2.03 mol, 150.30 mL) was added triethyl silane (21.60 g, 185.80 mmol, 29.60 mL) dropwise, and the system was reacted at room temperature for 16 hours. It was concentrated under reduced pressure. The residue was purified by column chromatography to afford WX127-3 (8.50 g, 47.44% yield), colorless oil. $^1$H NMR (400 MHz, CDCl3) δ 7.34 (s, 1H), 7.30-7.24 (m, 1H), 7.07 (d, J=8.0 Hz, 1H), 3.73 (s, 3H), 3.40-3.30 (m, 1H), 3.27-3.11 (m, 4H).

Step 3: Synthesis of Compound WX127-4

Synthesis of Compound WX127-4 was carried out by referring to the synthetic method of Example 3 Step 1, $^1$H NMR (400 MHz, CDCl3) δ 7.67 (s, 1H), 7.62 (d, J=7.5 Hz, 1H), 7.23 (d, J=7.5 Hz, 1H), 3.72 (s, 3H), 3.38-3.15 (m, 5H), 1.42-1.30 (m, 12H).

Step 4: Synthesis of Compound WX127-5

Synthesis of Compound WX127-5 was carried out by referring to the synthetic method of Example 3 Step 2, $^1$H NMR (400 MHz, CDCl3) δ 7.87 (s, 1H), 7.77 (d, J=7.8 Hz, 1H), 7.63 (t, J=7.7 Hz, 1H), 7.50 (d, J=8.0 Hz, 1H), 7.31 (d, J=7.8 Hz, 1H), 7.09 (d, J=7.5 Hz, 1H), 3.80-3.72 (m, 3H), 3.44-3.26 (m, 5H), 2.64 (s, 3H).

Step 5: Synthesis of Compound WX127-6

Synthesis of Compound WX127-6 was carried out by referring to the synthetic method of Example 8 Step 4, $^1$H NMR (400 MHz, CDCl3) δ 7.82 (s, 1H), 7.70 (br d, J=7.8 Hz, 1H), 7.63 (t, J=7.7 Hz, 1H), 7.47 (d, J=7.8 Hz, 1H), 7.29 (d, J=8.0 Hz, 1H), 7.09 (d, J=7.5 Hz, 1H), 3.44-3.18 (m, 5H), 2.64 (s, 3H).

Step 6: Synthesis of Compound WX127

Synthesis of Compound WX127 was carried out by referring to the synthetic method of Example 7 Step 1. $^1$H NMR (400 MHz, DMSO-d6) δ 8.47 (t, J=7.9 Hz, 1H), 8.11 (d, J=8.0 Hz, 1H), 7.91 (s, 1H), 7.83 (br d, J=8.3 Hz, 2H), 7.68 (br s, 1H), 7.51 (d, J=7.8 Hz, 1H), 4.15 (ddd, J=6.5, 8.8, 15.3 Hz, 1H), 3.77 (s, 3H), 3.51-3.23 (m, 4H), 2.85 (s, 3H), 2.49 (s, 3H).

Step 8: Synthesis of Compounds WX146 and WX147

Compound WX127 was chirally resolved by supercritical fluid chromatography (separation condition: column: AS (250 mm*30 mm, 5 um); mobile phase: supercritical $CO_2$/ EtOH (0.1% $NH_3H_2O$), B %: 40%-40%), to afford rotational Step 1: Synthesis of Compounds WX127-2A and WX127-2B At 0° C., to a solution of sodium hydride (17.06 g, 426.42 mmol, 60% purity) in tetrahydrofuran (200.00 mL) was isomers WX146 and WX147. Their retention time was respectively 3.7 min and 4.7 min Compound WX146, $^1$H NMR (400 MHz, DMSO-d6) δ 8.33 (br t, J=7.4 Hz, 1H), 8.03 (br d, J=8.0 Hz, 1H), 7.88 (s, 1H), 7.81 (br d, J=7.8 Hz, 1H), 7.71 (br d, J=7.5 Hz, 1H), 7.66 (br s, 2H), 7.48 (d, J=7.8 Hz, 1H), 4.19-4.08 (m, 1H), 3.76 (s, 3H), 3.72-3.71 (m, 1H), 3.72-3.71 (m, 1H), 3.40-3.39 (m, 1H), 3.40 (br s, 1H), 3.35 (br d, J=6.5 Hz, 4H), 2.79-2.71 (m, 1H), 2.75 (s, 2H), 2.49-2.48 (m, 2H) and WX147, $^1$H NMR (400 MHz, DMSO-d6) δ7.95 (s, 1H), 7.89 (d, J=8.0 Hz, 1H), 7.77-7.68 (m, 2H), 7.65 (s, 2H), 7.33 (d, J=8.0 Hz, 1H), 7.19 (d, J=6.8 Hz, 1H), 4.15-4.02 (m, 1H), 3.76 (s, 3H), 3.34-3.22 (m, 4H), 2.53 (br s, 3H), 2.49-2.48 (m, 3H).

Example 26: WX150 and WX151

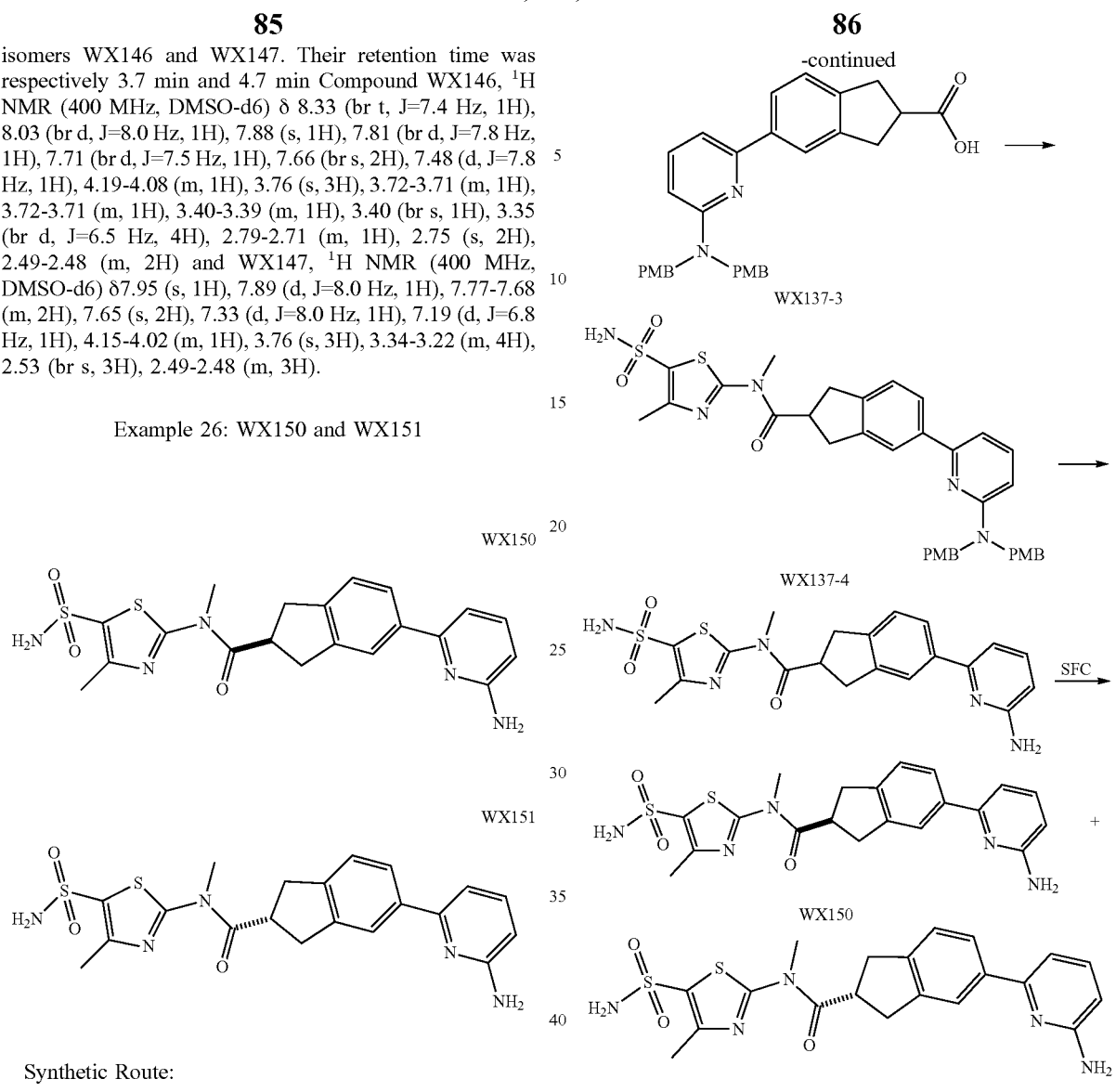

Synthetic Route:

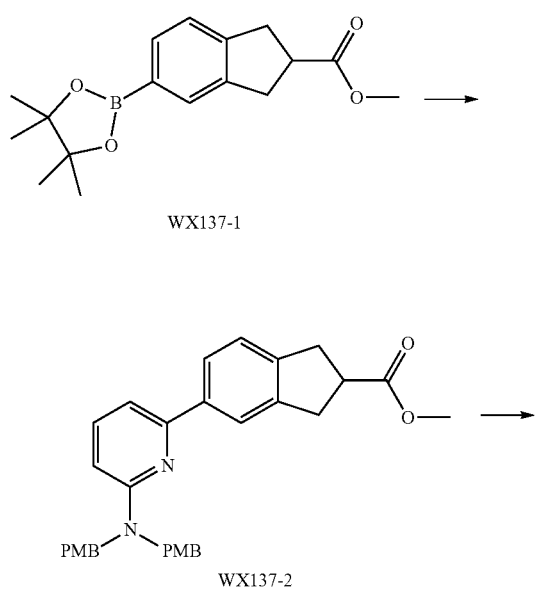

Step 1: Synthesis of Compound WX137-2

Synthesis of Compound WX137-2 was carried out by referring to the synthetic method of Example 3 Step 2, $^1$H NMR (400 MHz, CDCl3) δ 7.77 (s, 1H), 7.75 (s, 1H), 7.38-7.32 (m, 1H), 7.19-7.10 (m, 6H), 6.96 (d, J=7.3 Hz, 1H), 6.79-6.74 (m, 4H), 6.32 (d, J=8.3 Hz, 1H), 4.71 (s, 4H), 3.71 (s, 6H), 3.66 (s, 3H), 3.39-3.08 (m, 4H), 2.10 (s, 4H).

Step 2: Synthesis of Compound WX137-3

Synthesis of Compound WX137-3 was carried out by referring to the synthetic method of Example 8 Step 4, $^1$H NMR (400 MHz, CDCl3) δ 7.81-7.72 (m, 2H), 7.37-7.29 (m, 1H), 7.20-7.18 (m, 1H), 7.18 (s, 1H), 7.14-7.11 (m, 1H), 6.93 (d, J=7.5 Hz, 1H), 6.76 (d, J=8.8 Hz, 4H), 6.30 (d, J=8.3 Hz, 1H), 4.70 (s, 4H), 3.70 (s, 6H), 3.35-3.11 (m, 5H).

Step 3: Synthesis of Compound WX137-4

Synthesis of Compound WX137-4 was carried out by referring to the synthetic method of Example 7 Step 1. $^1$H NMR (400 MHz, CDCl3) δ 7.94 (s, 2H), 7.82-7.78 (m, 1H), 7.20-7.19 (m, 1H), 7.19 (s, 1H), 7.15-7.12 (m, 4H), 6.96 (d, J=7.5 Hz, 1H), 6.78-6.75 (m, 4H), 6.34 (d, J=8.5 Hz, 1H), 6.38-6.28 (m, 1H), 4.71 (s, 4H), 3.79-3.74 (m, 1H), 3.72 (s, 3H), 3.71 (s, 6H), 3.38-3.17 (m, 4H), 2.52 (s, 3H).

Step 4: Synthesis of Compound WX137

A solution of WX137-4 (350.00 mg, 511.82 μmol) in trifluoroacetic acid (12.32 g, 108.05 mmol, 8.00 mL) was reacted at room temperature for 16 hours. After the reaction was complete, it was concentrated under reduced pressure. The residue was purified by preparative chromatography to afford WX137 (184.00 mg, 80.38% yield), white solid. $^1$H NMR (400 MHz, DMSO-d6) δ 8.59-7.98 (m, 2H), 7.99-7.89 (m, 1H), 7.82 (s, 1H), 7.75 (br d, J=8.0 Hz, 1H), 7.64 (br s, 2H), 7.43 (d, J=8.0 Hz, 1H), 7.19 (d, J=7.3 Hz, 1H), 6.95 (d, J=8.8 Hz, 1H), 4.16-4.02 (m, 1H), 3.74 (s, 3H), 3.39-3.23 (m, 4H), 2.47 (s, 3H).

Step 5: Synthesis of Compounds WX150 and WX151

Compound WX137 (160 mg) was chirally resolved by supercritical fluid chromatography (separation condition: column: AS (250 mm*30 mm, 5 μm); mobile phase: supercritical CO$_2$/MeOH (0.1% NH$_3$H$_2$O), B %: 40%-40%), to afford rotational isomers WX150 and WX151. Their retention time was respectively 4.6 min and 6.4 min Compound WX150 (30 mg), $^1$H NMR (400 MHz, DMSO-d6) δ 8.48-7.92 (m, 3H), 7.79 (br s, 1H), 7.72 (br d, J=8.0 Hz, 1H), 7.65 (s, 2H), 7.47 (d, J=7.8 Hz, 1H), 7.21 (d, J=7.0 Hz, 1H), 6.96 (d, J=9.0 Hz, 1H), 4.19-4.08 (m, 1H), 3.76 (s, 3H), 3.37-3.26 (m, 4H), 2.53 (br s, 3H) and Compound WX151 (24 mg), $^1$H NMR (400 MHz, DMSO-d6) δ 8.48-7.92 (m, 3H), 7.79 (br s, 1H), 7.72 (br d, J=8.0 Hz, 1H), 7.65 (s, 2H), 7.47 (d, J=7.8 Hz, 1H), 7.21 (d, J=7.0 Hz, 1H), 6.96 (d, J=9.0 Hz, 1H), 4.19-4.08 (m, 1H), 3.76 (s, 3H), 3.37-3.26 (m, 4H), 2.53 (br s, 3H).

Example 27: WX148 and WX149

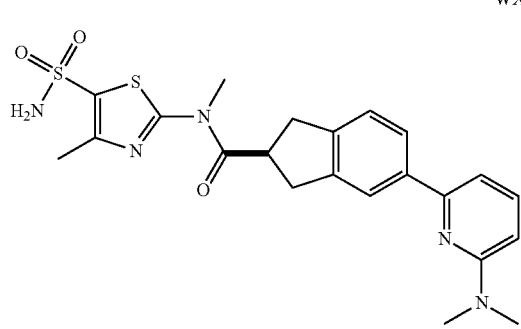

WX148

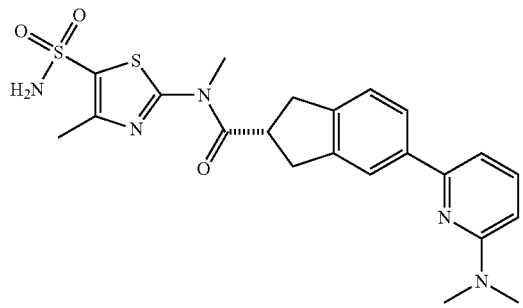

WX149

Synthetic Route:

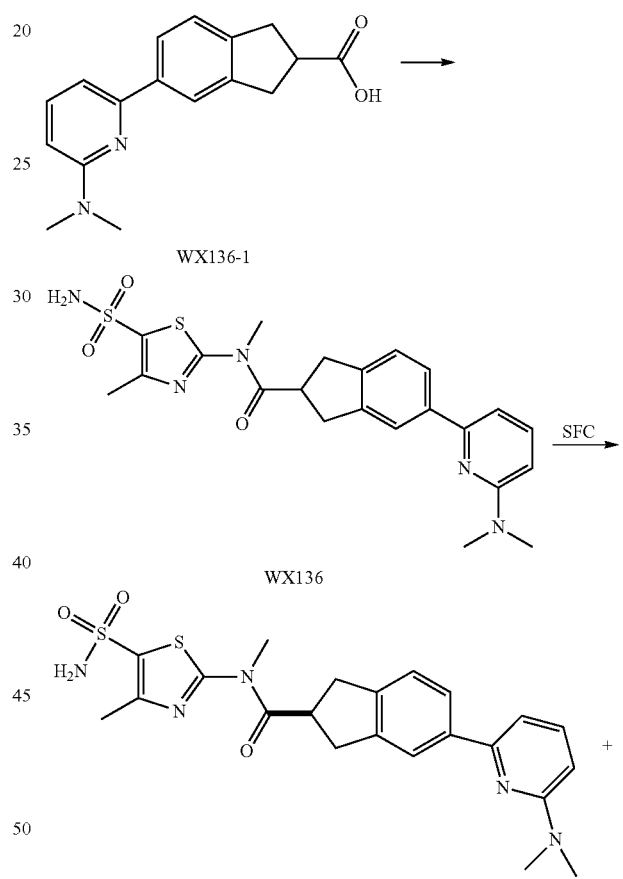

Step 1: Synthesis of Compound WX136

Synthesis of Compound WX136 was carried out by referring to the synthetic method of Example 7 Step 1. $^1$H NMR (400 MHz, DMSO-d6) δ 7.90 (s, 1H), 7.85 (d, J=7.8 Hz, 1H), 7.63 (s, 2H), 7.54 (t, J=7.9 Hz, 1H), 7.29 (d, J=8.0 Hz, 1H), 7.10 (d, J=7.5 Hz, 1H), 6.57 (d, J=8.3 Hz, 1H), 4.12-4.00 (m, 1H), 3.74 (s, 3H), 3.32-3.19 (m, 4H), 3.08 (s, 6H), 2.47-2.46 (m, 3H).

Step 2: Synthesis of Compound WX148 and WX149

Compound WX136 (40 mg) was chirally resolved by supercritical fluid chromatography (separation condition: column: AS (250 mm*30 mm, 5 μm); mobile phase: supercritical $CO_2$/EtOH, B %: 40%-40%), to afford rotational isomers WX148 and WX149. Their retention time was respectively 4.5 min and 5.1 min Compound WX148 (5 mg), $^1$H NMR (400 MHz, DMSO-d6) δ 7.81 (br s, 1H), 7.75 (br d, J=7.8 Hz, 2H), 7.65 (br s, 2H), 7.37 (br d, J=7.8 Hz, 1H), 7.11 (br d, J=7.3 Hz, 1H), 6.87 (br s, 1H), 4.15-4.05 (m, 1H), 4.05-4.05 (m, 1H), 3.75 (s, 3H), 3.38-3.33 (m, 1H), 3.36 (br d, J=9.5 Hz, 2H), 3.25-3.24 (m, 1H), 3.30 (br s, 3H), 3.19 (s, 6H), 2.48-2.47 (m, 1H) and WX149 (9 mg), $^1$H NMR (400 MHz, DMSO-d6) δ 7.92 (s, 1H), 7.87 (d, J=8.3 Hz, 1H), 7.64 (br s, 2H), 7.56 (t, J=7.9 Hz, 1H), 7.30 (d, J=7.8 Hz, 1H), 7.12 (d, J=7.5 Hz, 1H), 6.59 (d, J=8.5 Hz, 1H), 4.08 (br t, J=8.0 Hz, 1H), 3.76 (s, 3H), 3.33 (br s, 4H), 3.09 (s, 6H), 2.54-2.53 (m, 3H).

Assay Example 1: Herpes Simplex Virus Type 1 Cytopathic Effect Assay (In Vitro Evaluation)

Objective:
To evaluate the antiviral activity of compounds against the herpes simplex virus type 1 (HSV-1) GHSV-UL46 strain in the cytopathic effect (CPE) assay.

Assay Apparatus:
Cell incubator: Thermo 240I
Cell counter: Beckman Vi-Cell™ XR
Automatic dispenser: Thermo Multidrop™ Combi
Compound handling system: Labcyte ECHO 555 liquid handler
Microplate reader: Molecular Device SpectraMax340PC384.

Assay Materials:
Virus: HSV-1 GHSV-UL46, ATCC # VR-1544
Cells: African green monkey kidney cell Vero E6, obtained from Wuhan Institute of Virology, Chinese Academy of Sciences.

Assay Reagents:

| Name of the reagents | Brand and catalog No. |
|---|---|
| Dulbecco's Modified Eagle Medium (DMEM) | Gibco # 11995-065 |
| Fetal bovine serum (FBS) | Corning # 35-076-CV |
| Penicillin-Streptomycin (PS) | HyClone # SV30010 |
| Non-essential amino acids (NEAA) | Gibco # 11140050, 100× |
| Dulbecco's phosphate buffered saline (DPBS) | Corning # 21-031-CVR |
| Cell counting kit 8 (CCK8) | Biolite # 35004 |

Medium Configuration Method:
Cell culture medium: 500 ml DMEM+50 ml FBS+5 ml PS+5 ml NEAA.
Cytopathic assay medium: 500 ml DMEM+10 ml FBS+5 ml PS+5 ml NEAA.

Assay Steps:
1. Cell seeding (Day. 1)
   1.1. The worktable of the biosafety cabinet was wiped with 75% alcohol, and the biosafety cabinet was exposed to UV light for 15 minutes. The exhaust fan was turn on, the glass window was lowered to the lower edge of the cordon, and the airflow inside the cabinet was stablized for 5 minutes.
   1.2. One bottle (T 150 cell culture flask) of Vero E6 cells with a cell density of 80% was taken out. The growth medium was aspirated, and the cells were washed twice with 10 ml of phosphate buffer. 2 ml of trypsin was added, and the cells were digested in an incubator (37° C., $CO_2$).
   1.3. After the cells were separated and detached, 15 ml of cytopathic assay medium was added to terminate the digestion. After the cells were pipetted several times, 1 ml of the cell suspension was counted by a cell counter.
   1.4. The cells were diluted to 1.33×105 cells/ml using cytopathic assay medium. The diluted cell suspension was added to a 384-well plate (Corning #3701) by using Multidrop, and 30 μl of the diluted cell suspension (4000 cells) per well were added.
   1.5. The cells were evenly distributed by shaking the plate gently. They were placed and cultured overnight in a 37° C., $CO_2$ cell culture incubator.
2. Compound dilution, treatment and virus inoculation (Day. 2)
   2.1. The gradient dilution of the compound was performed with DMSO, and the diluted compound was added to the ECHO source plate.
   2.2. Compounds were added to cell-inoculated 384-well plates using an ECHO 555 liquid workstation. Eight concentrations were tested in duplicate for each assay compound. For the cell control wells, neither compound nor virus was added. For the virus control wells, no compound was added. The final concentration of DMSO in all the wells was 0.5%.
   2.3. The virus was diluted with the assay medium at an inoculation amount of 1.5 $TCID_{90}$/well, 30 μl. The assay medium was added to the cell control wells with Multidrop, 30 μl per well. Then the diluted virus was added to the compound test wells and the virus control wells with Multidrop, 30 μl per well.
   2.4. The cell plates were placed and cultured in a 37° C., $CO_2$ cell incubator for 5 days.
3. Cell viability Detection (Day. 7)
   3.1. After 5 days of culture, the cytopathic condition in all wells of the cell plate was observed, and the cells in the cell control well should be free of cytopathy, and almost all of the cells in the virus control wells showed cytopathy.
   3.2. CCK8 was added to the cell plate with Multidrop, 6 μl per well.
   3.3. The cell plates were placed and incubated in a 37° C., $CO_2$ cell incubator for 3 hours.
   3.4. The absorbance of each well of the cell plate was read with a microplate reader at a wavelength of 450 nm, and 630 nm was used as the reference wavelength. The raw data were obtained by substrating the absorbance at 630 nm from the absorbance at 450 nm (Raw data=$OD_{450}$-$OD_{630}$).
4. Data analysis
   4.1. The antiviral activity (% Inhibition) of the assay compound was calculated using the following equation:

$$\% \text{ Inhibition} = \left( \frac{\text{Sample} - \text{virus control}}{\text{cell control} - \text{virus control}} \right) \times 100$$

wherein, Sample is the absorbance of the compound test well; cell control is the average of the absorbances of the cell control wells; and virus control is the average of the absorbances of the virus control wells.

4.2. Dose-response curves were plotted using GraphPad Prism software and the half maximal effective concentration ($EC_{50}$) of the assay compounds was determined.

5. The assay results were shown in Table 1.

TABLE 1

HSV-1 cytopathic assay results

| Example Compound | Compound No. | HSV-1 cytopathic effect $EC_{50}$ (μM) |
|---|---|---|
| 1 | WX042 | 0.042 |
| 3 | WX128 | 0.14 |
| 6 | WX131 | 0.13 |
| 9 | WX043 | 0.009 |
| 10 | WX072 | 0.36 |
| 11 | WX073 | 0.12 |
| 12 | WX074 | 0.043 |
| 13 | WX129 | 0.046 |
| 14 | WX156 | 0.65 |
| 15 | WX130 | 0.017 |
| 16 | WX142 | 0.15 |
| 17 | WX133 | 0.14 |
| 18 | WX144 | 0.41 |
| 19 | WX017 | 0.046 |
|  | WX018 | 0.25 |
| 20 | WX030 | 0.95 |
|  | WX031 | 0.77 |
| 21 | WX036 | >1 |
|  | WX037 | 0.007 |
| 22 | WX158 | >1 |
|  | WX159 | 0.017 |
| 23 | WX154 | 0.31 |
|  | WX155 | 0.024 |
| 24 | WX152 | 0.007 |
|  | WX153 | 0.81 |
| 25 | WX146 | 0.012 |
|  | WX147 | 0.78 |
| 26 | WX150 | 0.012 |
|  | WX151 | 0.23 |
| 27 | WX148 | 0.044 |
|  | WX149 | 0.55 |

Conclusion: The compounds disclosed herein have good antiviral activity against herpes simplex virus (HSV).

Assay Example 2: Evaluation of Compounds' Pharmacokinetics

Objective: To test the pharmacokinetics of compounds in mice in vivo.

Experimental Materials

Balb/c mice (male, 18-22 g, 6-8 weeks old, Shanghai Slack)

Experimental Procedures

The pharmacokinetics profile of the compound in rodent was tested using a standard protocol after intravenous and oral administrations. The candidate compound was prepared as a corresponding solution, which was administered as a single intravenous injection (1.0 mg/kg, 5% DMSO/95% 20% hydroxypropyl-β-cyclodextrin) or gavage (1.0 mg/kg, 0.5% methyl Cellulose MC4000). The whole blood samples were collected within 24 hours, centrifuged at 3000 g for 15 minutes, and plasma samples were obtained by separating the supernatant. 4 times volume of acetonitrile solution containing an internal standard was added to precipitate proteins. After centrifugation, the supernatant was collected, to which an equal volume of water was added, and further centrifuged to collect the supernatant. The LC-MS/MS analysis method was used to quantitatively analyze the plasma concentration, and the pharmacokinetics parameters, such as peak concentration, peak time, clearance rate, half-life, area under the curve, and bioavailability were calculated.

The experimental results were shown in Table 2:

TABLE 2

Pharmacokinetic assay results

| Test substance (Compounds prepared by examples) | Clearance (mL/min/kg) Parameters for Intravenous administration | Half life $T_{1/2}$ (h) | Concentration Integral AUC (nM · hr) Parameters for Oral administration | Bioavailability F (%) |
|---|---|---|---|---|
| Reference (Pritelivir) | 0.4 | 6 | 128921 | 100 |
| Example 21 (WX037) | 1.2 | 6 | 24371 | 75 |

Conclusion: The compounds disclosed herein have better activity. In the in vivo pharmacokinetics studies on mice administered intragastrically, the plasma exposure of the compound is lower for the same effective dose and thus the safety thereof is better.

The invention claimed is:

1. A compound represented by formula (I), or an isomer or a pharmaceutically acceptable salt thereof,

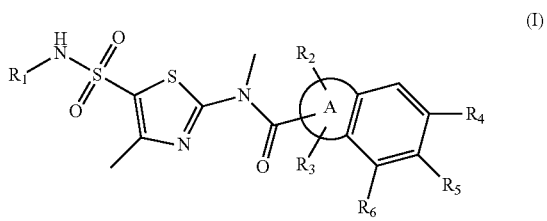

wherein,
R₁ is selected from H, $C_{1-4}$ alkyl or $C_{3-6}$ cycloalkyl;
R₂ and R₃ are independently selected from H, or are independently selected from $C_{1-3}$ alkyl optionally substituted by 1, 2 or 3 R;
R₄, R₅, and R₆ are independently selected from H, F, Cl, Br or I, or are independently selected from the group consisting of phenyl, 5- to 6-membered heteroaryl, and 5- to 6-membered heteroaryl-O—, each of which is optionally substituted by 1, 2 or 3 R;
ring A is selected from $C_{5-7}$ cycloalkyl or 5- to 8-membered heterocycloalkyl;
R is selected from F, Cl, OH, NH₂, —COOH, $C_{1-3}$ alkyl, $C_{1-3}$ alkoxy, —N,N-di($C_{1-3}$ alkyl)amino, or $C_{1-3}$ alkyl-C(=O)O—;
the heteroatom or heteroatom group in the 5- to 6-membered heteroaryl and the 5- to 8-membered heterocycloalkyl is independently selected from —S—, —O—, —NH—, or N; and
in any of the above cases, the number of the heteroatom or heteroatom group is independently selected from 1, 2 or 3.

2. The compound, or the isomer or the pharmaceutically acceptable salt thereof according to claim 1, wherein R is selected from F, Cl, OH, NH$_2$, —COOH, CH$_3$,

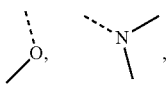

or CH$_3$—C(=O)O—.

3. The compound, or the isomer or the pharmaceutically acceptable salt thereof according to claim 1, wherein R$_1$ is selected from H or

4. The compound, or the isomer or the pharmaceutically acceptable salt thereof according to claim 1, wherein R$_2$ and R$_3$ are independently selected from H, or are independently selected from the group consisting of CH$_3$ and —CH$_2$—CH$_3$, each of which is optionally substituted by 1, 2 or 3 R.

5. The compound, or the isomer or the pharmaceutically acceptable salt thereof according to claim 4, wherein R$_2$ and R$_3$ are independently selected from H, CH$_3$, —CH$_2$—OH, or —CH$_2$—OAc.

6. The compound, or the isomer or the pharmaceutically acceptable salt thereof according to claim 5, wherein R$_2$ is selected from H, CH$_3$, —CH$_2$—OH, or —CH$_2$—OAc.

7. The compound, or the isomer or the pharmaceutically acceptable salt thereof according to claim 5, wherein R$_3$ is selected from H or CH$_3$.

8. The compound, or the isomer or the pharmaceutically acceptable salt thereof according to claim 1, wherein R$_4$, R$_5$ and R$_6$ are independently selected from H, F, Cl, Br or I, or are independently selected from the group consisting of pyridyl, thiazolyl, and pyridyl-O—, each of which is optionally substituted by 1, 2 or 3 R.

9. The compound, or the isomer or the pharmaceutically acceptable salt thereof according to claim 7, wherein R$_4$, R$_5$ and R$_6$ are independently selected from H, F, Cl, Br or I, or are independently selected from the group consisting of

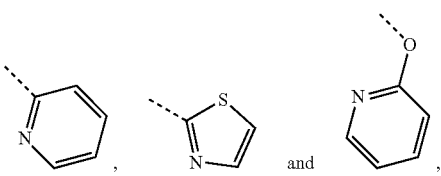

each of which is optionally substituted by 1, 2 or 3 R.

10. The compound, or the isomer or the pharmaceutically acceptable salt thereof according to claim 9, wherein R$_4$, R$_5$, and R$_6$ are independently selected from H, F, Cl,

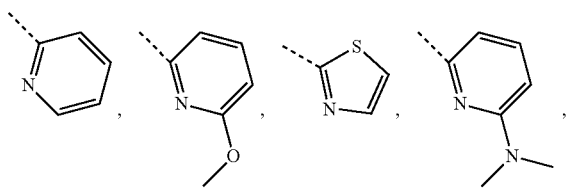

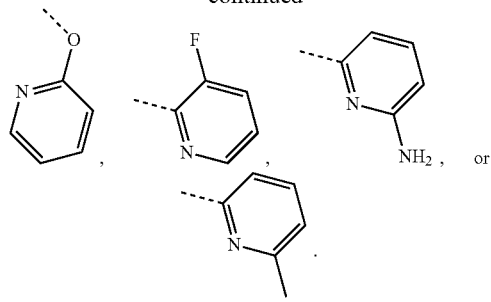

11. The compound, or the isomer or the pharmaceutically acceptable salt thereof according to claim 10, wherein R$_4$ is selected from H, F, Cl, or

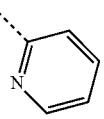

12. The compound, or the isomer or the pharmaceutically acceptable salt thereof according to claim 10, wherein R$_5$ is selected from H,

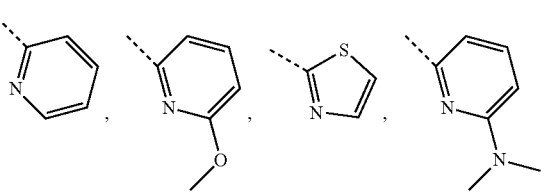

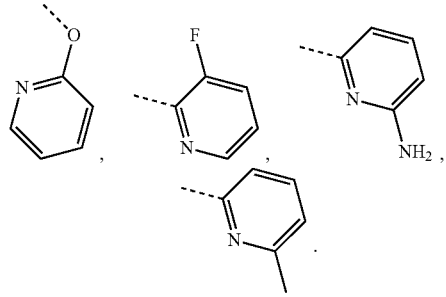

13. The compound, or the isomer or the pharmaceutically acceptable salt thereof according to claim 10, wherein R$_6$ is selected from H, F, Cl, or

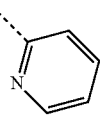

14. The compound, or the isomer or the pharmaceutically acceptable salt thereof according to claim 1, wherein ring A is selected from piperidyl, pyrrolidinyl, tetrahydrofuryl, tetrahydropyranyl, oxepanyl, cyclopentyl, or cyclohexyl.

15. The compound, or the isomer or the pharmaceutically acceptable salt thereof according to claim 1, wherein the moiety

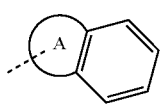
is selected from:
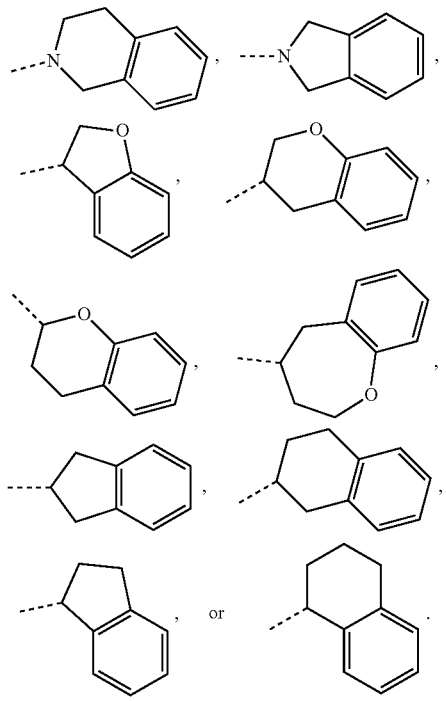
16. The compound, or the isomer or the pharmaceutically acceptable salt thereof according to claim 15, wherein the moiety
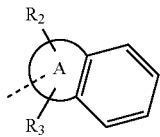
is selected from:
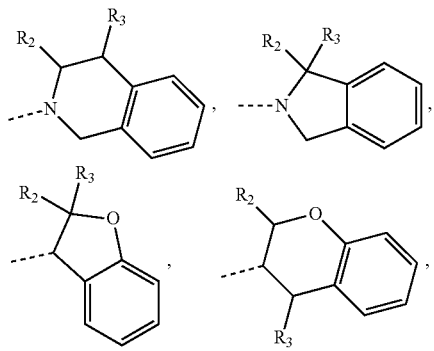
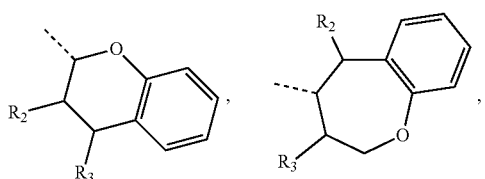
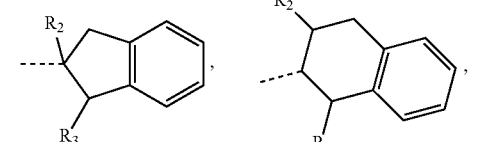
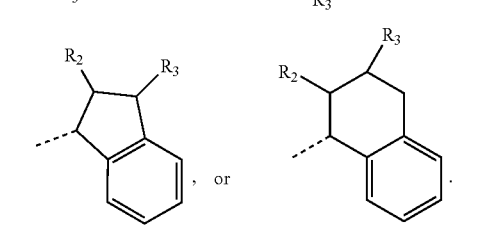
17. The compound, or the isomer or the pharmaceutically acceptable salt thereof according to claim 16, wherein the moiety
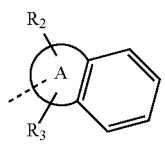
is selected from:
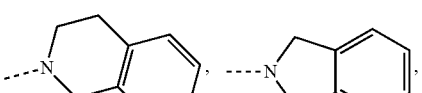
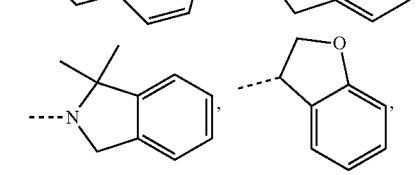
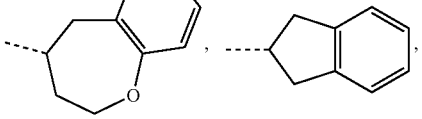
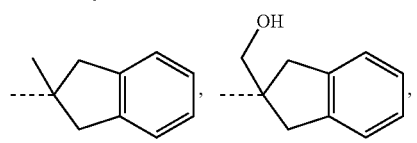

-continued
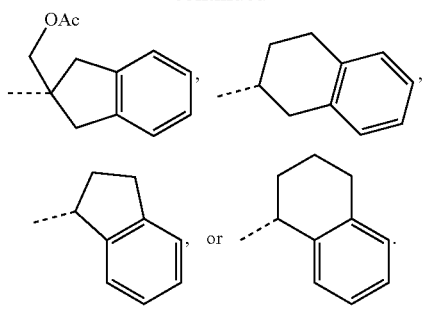
18. The compound, or the isomer or the pharmaceutically acceptable salt thereof according to claim 1, which is selected from:
(I-1)
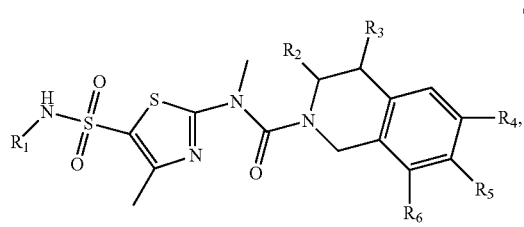
(I-2)
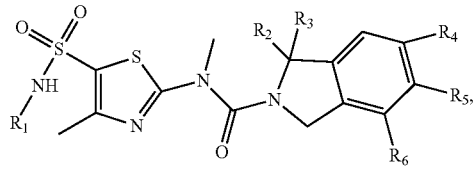
(I-3)
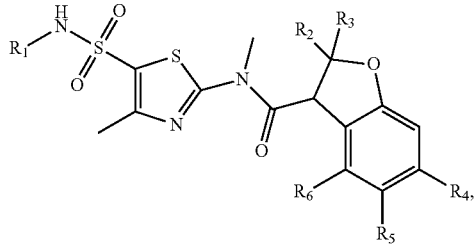
(I-4)
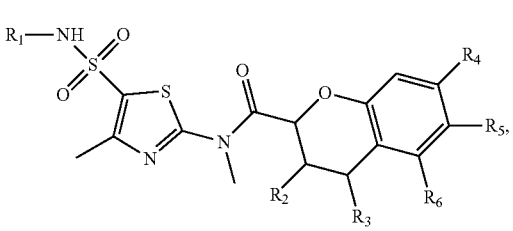
(I-5)
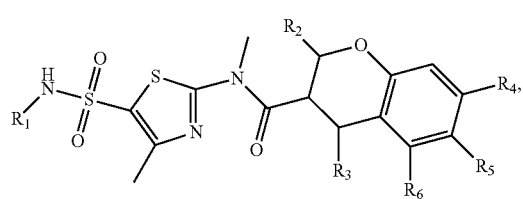
-continued
(I-6)
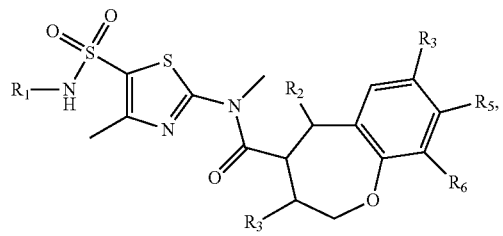
(I-7)
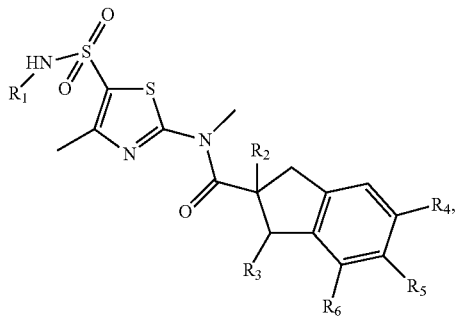
(I-8)
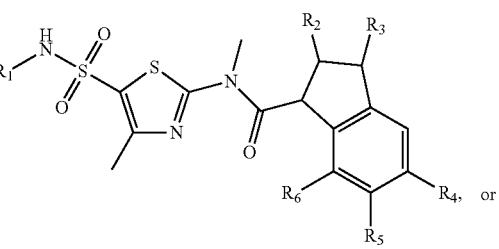
(I-9)
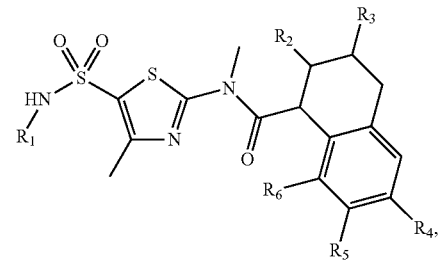
(I-10)
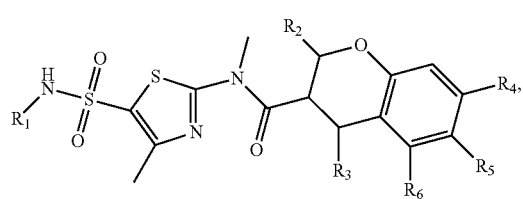
wherein
$R_1$, $R_2$, $R_3$, $R_4$, $R_5$, and $R_6$ are as defined in claim 1.
19. A compound of a formula, or an isomer or a pharmaceutically acceptable salt thereof, wherein the formula is selected from the group consisting of

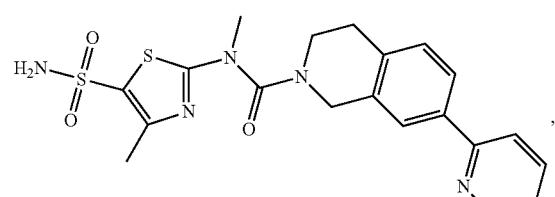
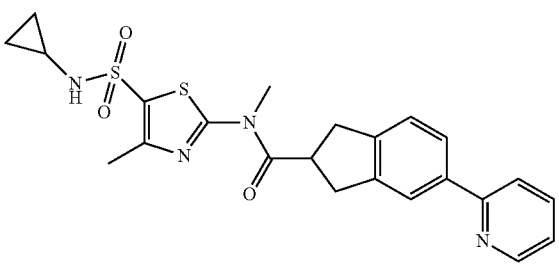
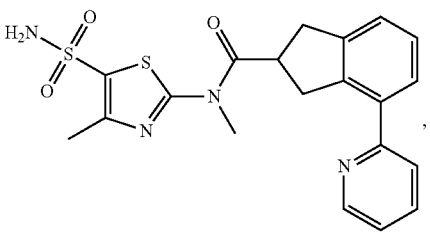
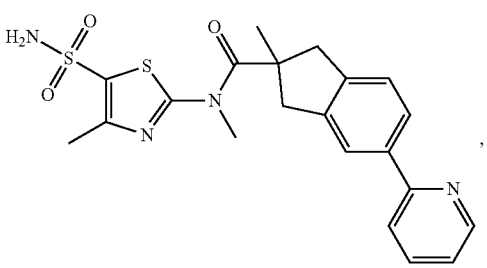
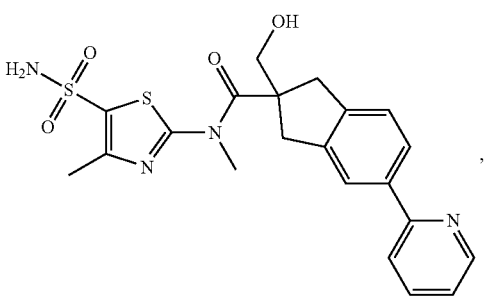
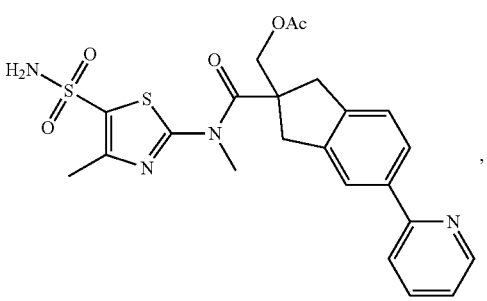
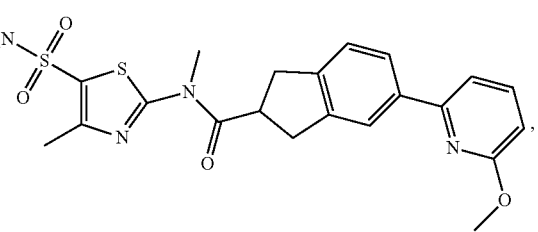

101
-continued
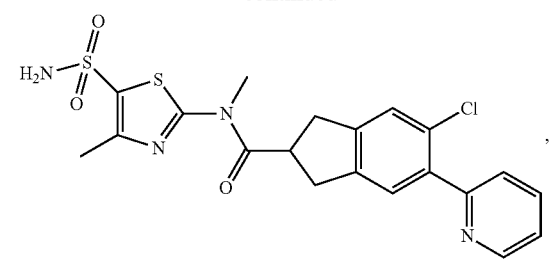
,
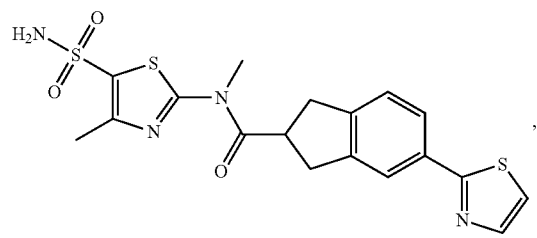
,
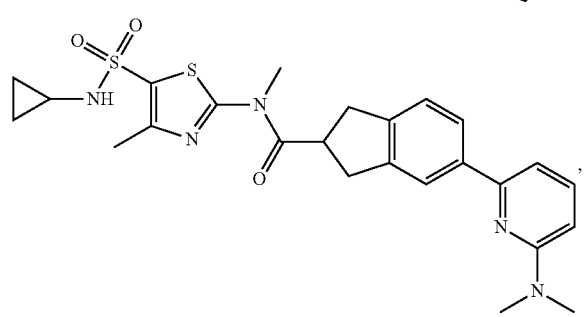
,
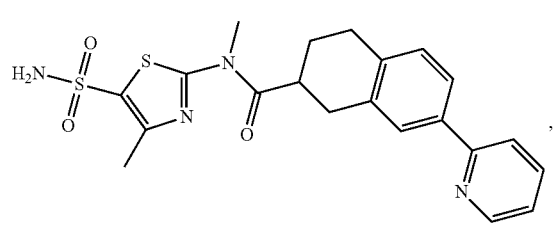
,
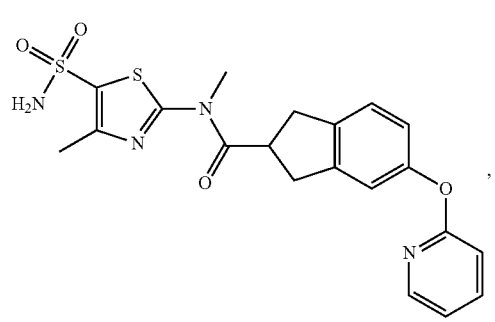
,
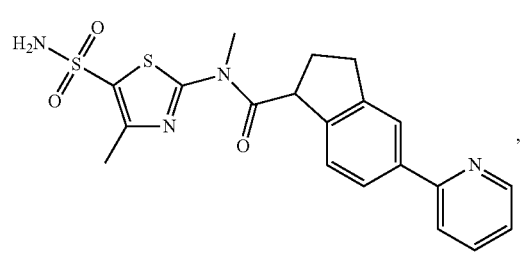
,
102
-continued
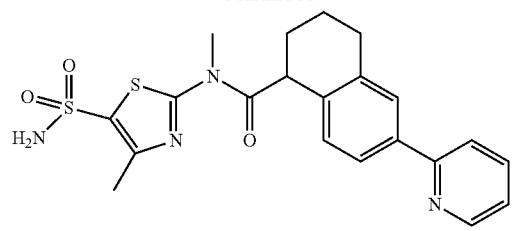
,
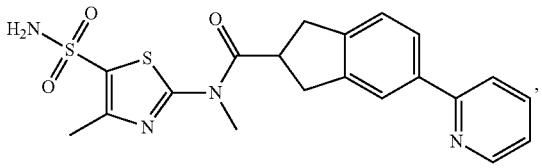
,
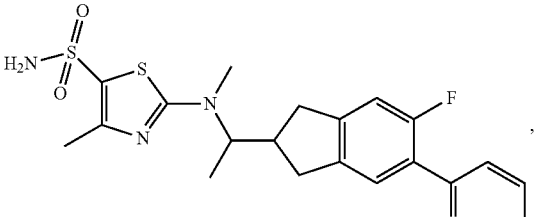
,
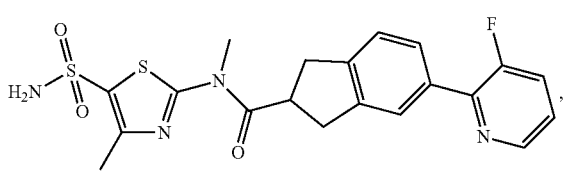
,
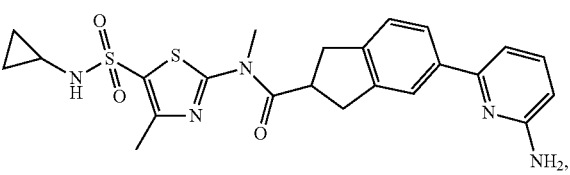
,
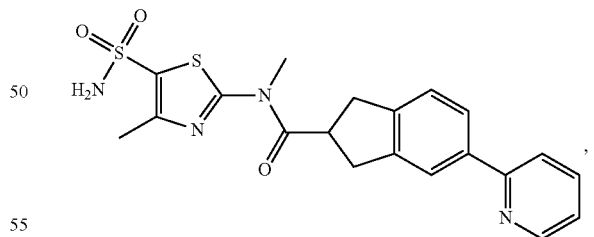
,
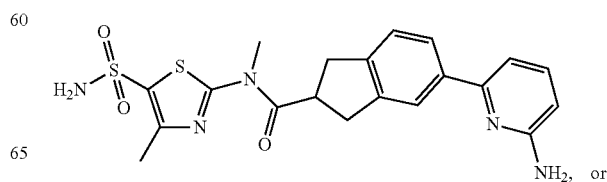
, or

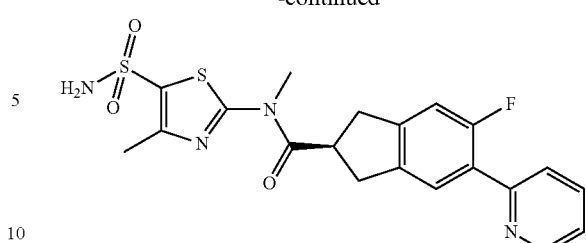
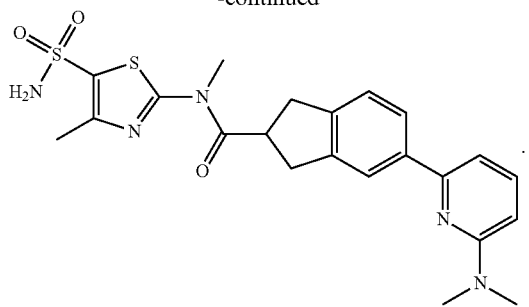
20. The compound, or the isomer or the pharmaceutically acceptable salt thereof according to claim 19, which is selected from:
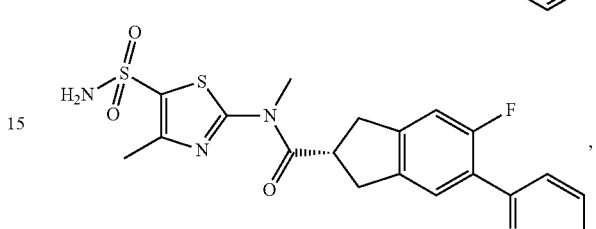
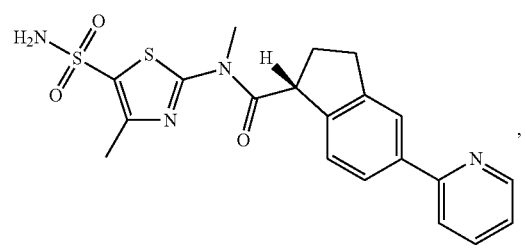
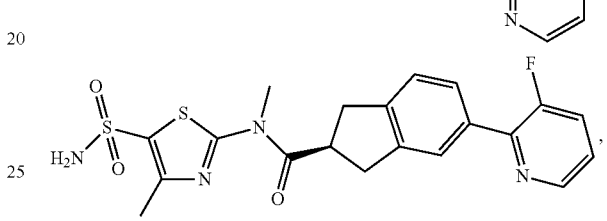
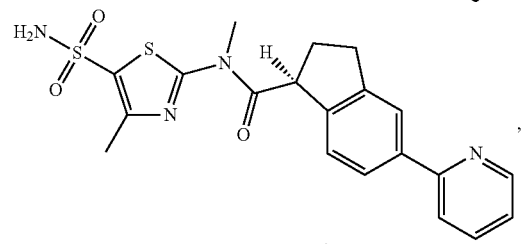
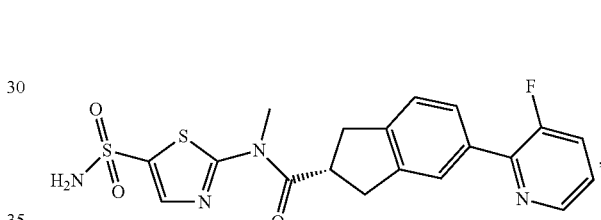
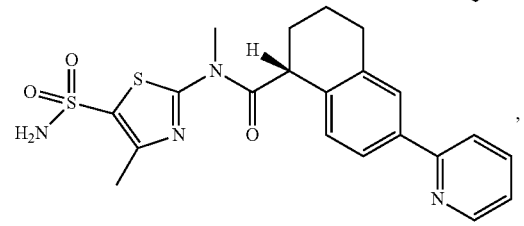
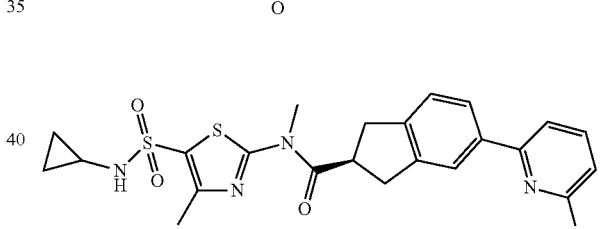
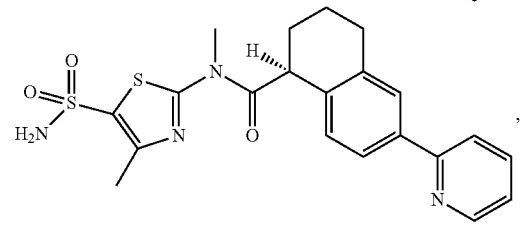
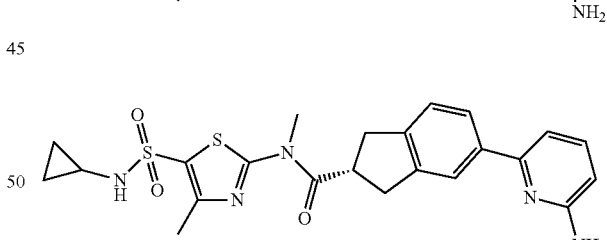
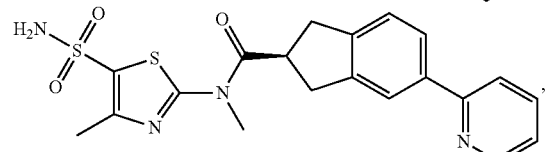
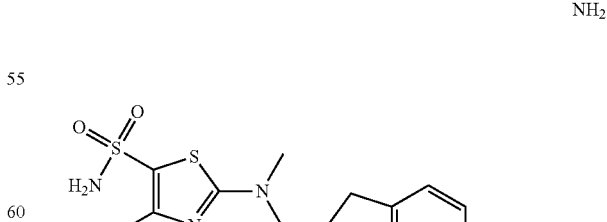
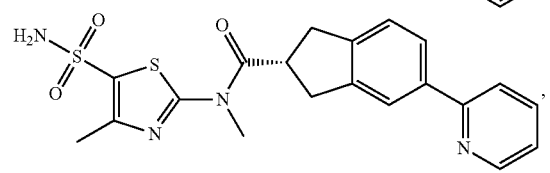
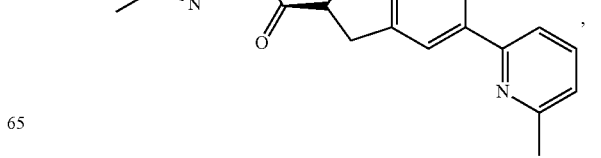

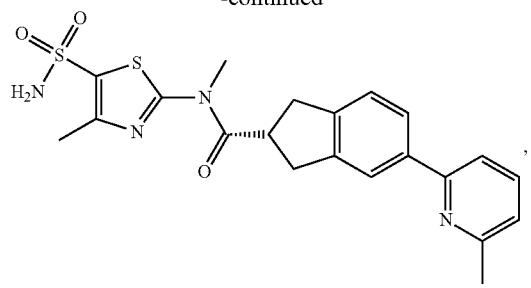
,
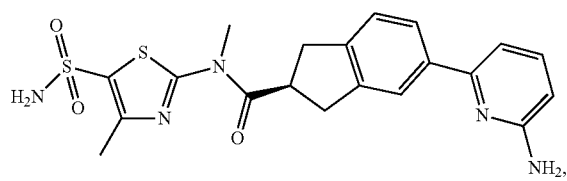
,
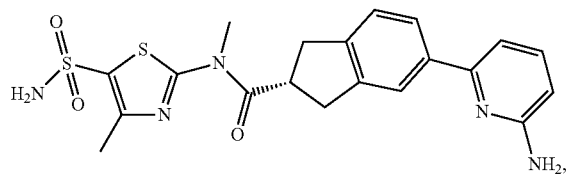
,
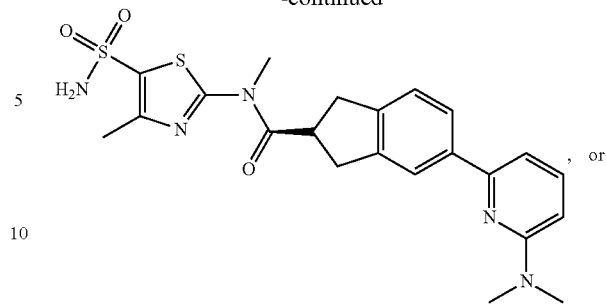
, or
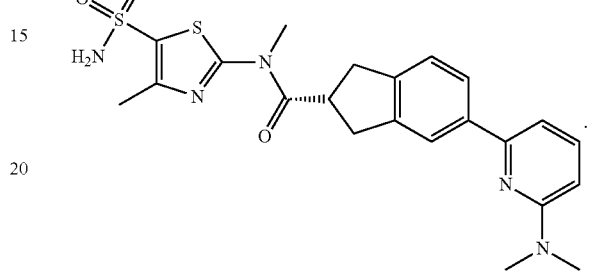
.
21. A pharmaceutical composition, comprising:
a therapeutically effective amount of the compound or the pharmaceutically acceptable salt thereof according to claim 1, and
a pharmaceutically acceptable carrier.
* * * * *